US008710097B2

(12) United States Patent
Chan et al.

(10) Patent No.: US 8,710,097 B2
(45) Date of Patent: Apr. 29, 2014

(54) FLAVONOID DIMERS AND METHODS OF MAKING AND USING SUCH

(75) Inventors: Tak-Hang Chan, Toronto (CA); Larry Ming-Cheung Chow, Hong Kong (CN)

(73) Assignees: The Hong Kong Polytechnic University, Hong Kong (CN); McGill University, Montreal, Quebec (CA)

( * ) Notice: Subject to any disclaimer, the term of this patent is extended or adjusted under 35 U.S.C. 154(b) by 716 days.

(21) Appl. No.: 12/301,504

(22) PCT Filed: May 9, 2007

(86) PCT No.: PCT/IB2007/051730
§ 371 (c)(1),
(2), (4) Date: Mar. 11, 2009

(87) PCT Pub. No.: WO2007/135592
PCT Pub. Date: Nov. 29, 2007

(65) Prior Publication Data
US 2009/0197943 A1 Aug. 6, 2009

Related U.S. Application Data

(60) Provisional application No. 60/801,390, filed on May 19, 2006, provisional application No. 60/872,989, filed on Dec. 6, 2006.

(51) Int. Cl.
*A61K 31/353* (2006.01)
*C07D 405/12* (2006.01)
*A61P 43/00* (2006.01)

(52) U.S. Cl.
USPC .......................................... 514/456; 549/403

(58) Field of Classification Search
None
See application file for complete search history.

(56) References Cited

U.S. PATENT DOCUMENTS

2007/0155695 A1  7/2007  Wirth et al.

FOREIGN PATENT DOCUMENTS

WO     WO 01/03681        1/2001
WO     WO 2005/068484 A1  7/2005

OTHER PUBLICATIONS

Boumendjel et al. in Medicinal Research Reviews, vol. 22, No. 5, 512-529, 2002.*
Sauna et al in Biochemistry 2004, 43, 2262-2271.*
Kin-Fai Chan et al., "Flavonoid Dimers as Bivalent Modulators for P-Glycoprotein-Based Multidrug Resistance: Synthetic Apigenin Homodimers Linked with Defined-Length Poly(ethylene glycol) Spacers Increase Drug Retention and Enhance Chemosensitivity in Resistant Cancer Cells," J. Med. Chem., Nov. 16, 2006, pp. 6742-6759, vol. 49, No. 23, American Chemical Society.
Iris L.K. Wong et al., "Flavonoid Dimers as Bivalent Modulators for Pentamidine and Sodium Stiboglucanate Resistance in *Leishmania*," Antimicrobial Agents and Chemotherapy, Mar. 2007 (published ahead of print on Dec. 28, 2006), pp. 930-940, vol. 51, No. 3, American Society for Microbiology.
Bargellini et al. "Sul 2-3-4'-Triossi-Flavone" Gazzetta Chimica Italiana, 1927, vol. 57, pp. 605-609, In italian—considered to the extent discussed in p. 36-37 of spec.
Basselin et al., "Pentamidine Uptake in *Leishmania donovani* and *Leishmania amazonensis* Promastigotes and Axenic Amastigotes" Biochem. J., 1996, vol. 315, pp. 631-634.
Berman, "Human Leishmaniasis: Clinical, Diagnostic, and Chemotherapeutic Developments in the Last 10 Years" Clinical Infectious Diseases, 1997, vol. 24, pp. 684-703.
Burkett et al., "An Expedient Synthesis of Monodispersed Oligo (Ethylene Glycols)" Synthesis, 2004, No. 7, pp. 1007-1010.
Cibin et al., "Synthesis of a Ditopic Cyclophane Based on the Cyclobutane Ring by Chalcone Photocycloaddition" Tetrahedron, 2003, vol. 59, pp. 3455-3459.
Chow et al., "Cloning and Functional Analysis of an Extrachromosomally Amplified Multidrug Resistance-like Gene in *Leishmania enriettii*" Molecular and Biochemical Parasitology, 1993, vol. 60, pp. 195-208.
De Wet et al., "Sequence Requirements of the ATP-Binding Site within the C-Terminal Nucleotide-Binding Domain of Mouse P-Glycoprotein: Structure-Activity Relationships for Flavonoid Binding" Biochemistry, 2001, vol. 40, 10382-10391.
Di Pietro et al., "Modulation by Flavonoids of Cell Multidrug Resistance Mediated by P-Glycoprotein and Related ABC Transporters" CMLS Cellular and Molecular Life Sciences, 2002, vol. 59, pp. 307-322.
Huang et al., "Lewis Acid Catalyzed Solid-Phase Synthesis of Flavonoids Using Selenium-Bound Resin" J. Comb. Chem., 2005, vol. 7, pp. 802-805.
Iyer et al., "Synthesis of Orthogonal end Functionalized Oligoethylene Glycols of Defined Lengths" Tetrahedron Letter, 2004, vol. 45, pp. 4285-4288.
Jesthi et al., "Antispasmodics Derived form Hydroxyflavones" Jour. Indian Chem. Soc., 1965, vol. 42, No. 2, pp. 105-108.
Jha et al., "Studies in Halochalcones and Related Compounds: Synthesis of 3':5'-Dichloro-2'-Hydroxychalcones and Their Derivatives" Tetrahedron, 1958, vol. 2, pp. 241-245.

(Continued)

*Primary Examiner* — Dennis Heyer
(74) *Attorney, Agent, or Firm* — Buchanan Ingersoll & Rooney PC

(57) ABSTRACT

Multidrug resistance (MDR) is a major problem in cancer chemotherapy. The best characterized resistance mechanism is the one mediated by the over-expression of drug efflux transporters, permeability-glycoprotein (P-gp), which pump a variety of anticancer drugs out of the cells, resulting in lowered intracellular drug accumulation. A series of flavonoid dimers are developed in this invention, which are linked together by linker groups of various lengths. These flavonoid dimers are found to be efficient P-gp modulators that increase cytotoxicity of anticancer drugs in vitro and dramatically enhance their intracellular drug accumulation. It is found that the flavonoid dimers of this invention is also useful in reducing drug resistance in treating parasitic diseases.

18 Claims, 20 Drawing Sheets

(56) References Cited

OTHER PUBLICATIONS

Kumazawa et al., "An Effective Synthesis of Isoorientin: the Regioselective Synthesis of a 6-C-Glucosylflavone" Carbohydrate Research, 2000, vol. 329, pp. 507-513.

Leonessa et al., "MDA435/LCC6 and MDA435/LCC6$^{MDR1}$: Ascites Models of Human Breast Cancer" British Journal of Cancer, 1996, vol. 73, pp. 154-161.

Lum et al., "MDR Expression in Normal Tissues, Pharmacologic Implications for Clinical Use of P-Glycoprotein Inhibitors" Hematology/Oncology Clinics of North America, 1995, vol. 9, No. 2, pp. 319-336.

Miyake et al., "Syntheses of Flavones Via the Iodine-Mediated Oxidative Cyclization of 1,3-Diphenylprop-2-en-1-ones" Bull. Chem. Soc. Jpn., 2003, vol. 76, pp. 835-836.

Ono et al., "Radioiodinated Flavones for in Vivo Imaging of β-Amyloid Plaques in the Brain" J. Med. Chem., 2005, vol. 48, pp. 7253-7260.

Pelter et al., "Oxidation Experiments with Flavonoids" Phytochemistry, 1971, vol. 10, pp. 835-850.

Pelter et al., "Induction of 2,3-Aryl Migrations in 3-Bromoflavanones" J.C.S. Chem. Comm., 1976, pp. 151-152.

Pradines et al., "Chemosensitizers in Drug Transport Mechanisms Involved in Protozoan Resistance" Current Drug Targets-Infectious Disorders, 2005, vol. 5, pp. 411-431.

Sundar et al., "Circulating T Helper 1 (TH1) Cell- and TH2 Cell-Associated Cytokines in Indian Patients with Visceral Leishmaniasis" The American Journal of Tropical Medicine and Hygiene, 1997, vol. 56, No. 5, pp. 522-525.

Tsuruo et al., "Overcoming of Vincristine Resistance in P388 Leukemia in Vivo and in Vitro through Enhanced Cytotoxicity of Vincristine and Vinblastine by Verapamil" Cancer Research, 1981, vol. 41, pp. 1967-1972.

Twentyman et al., "Resistance Modification by PSC-833, a Novel Non-Immunosuppressive Cyclosporin A" European Journal of Cancer, 1991, vol. 27, No. 12, pp. 1639-1642.

Yanagisawa et al., "Biricodar (VX-710; Incel$^{IM}$): an Effective Chemosensitizer in Neuroblastoma" British Journal of Cancer, 1999, vol. 80, No. 8, 1190-1196.

Zaveri, "Synthesis of a 3,4,5-Trimethoxybenzoyl Ester Analogue of Epigallocatechin-3-gallate (EGCG): A Potential Route to the Natural Product Green Tea Catechin, EGCG" Organic Letters, 2001, vol. 3, No. 6, pp. 843-846.

International Search Report for PCT/IB2007/051730, completed Sep. 18, 2007.

\* cited by examiner

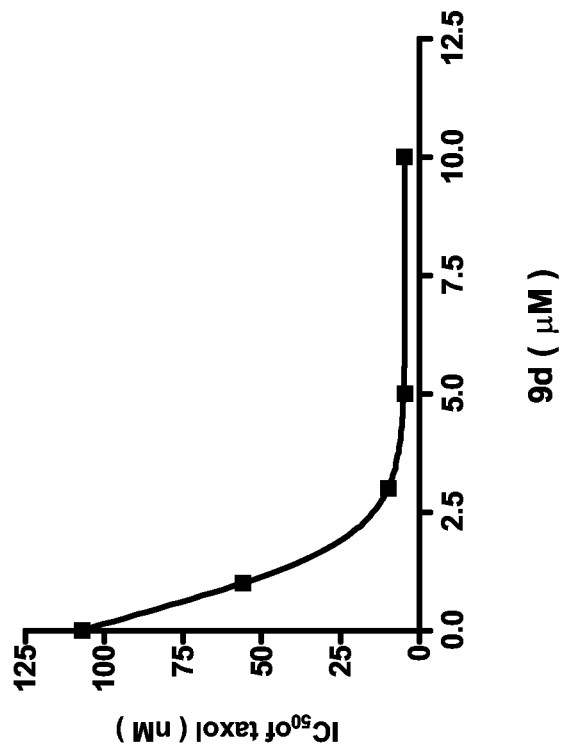
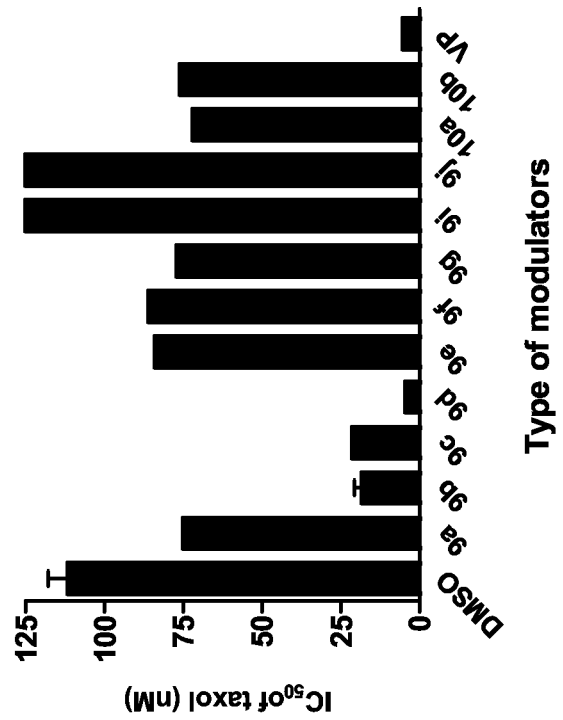
Figure 3A
Figure 3B

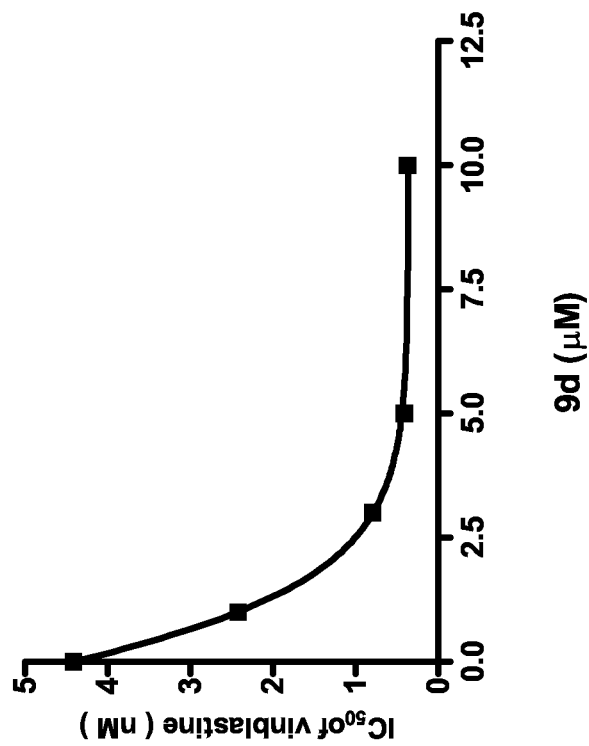
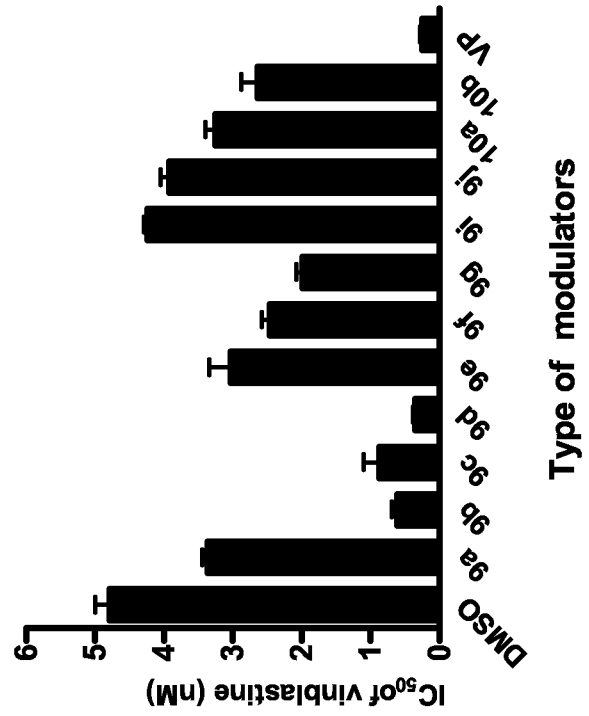

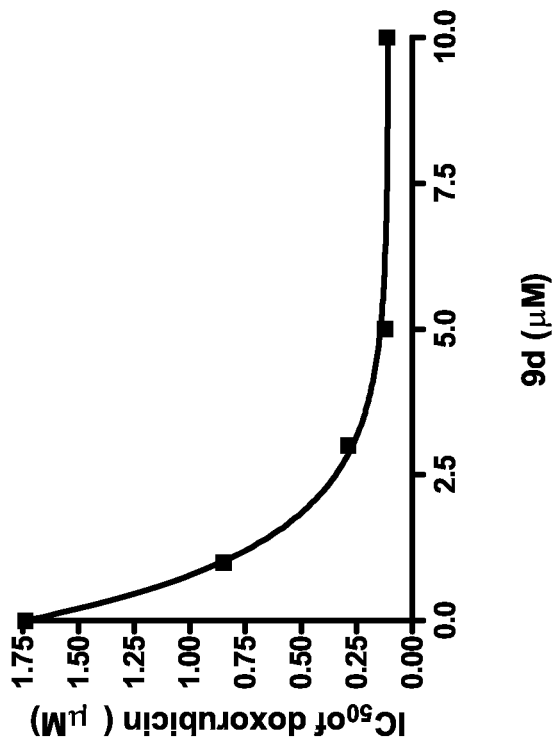
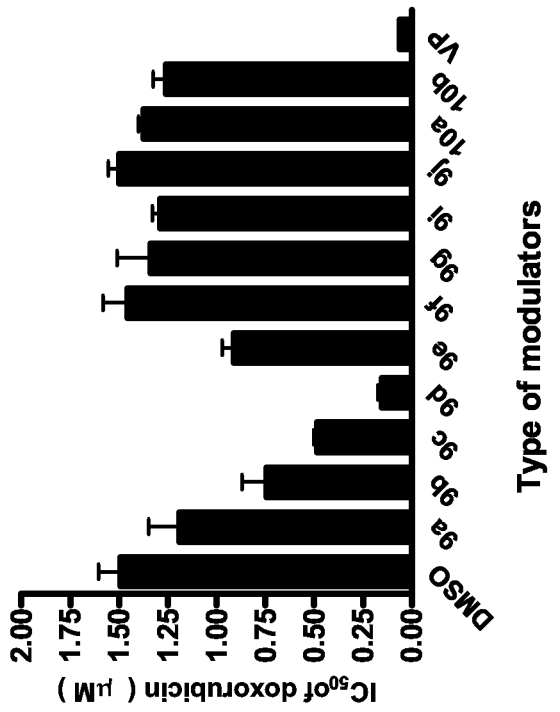
Figure 8A
Figure 8B

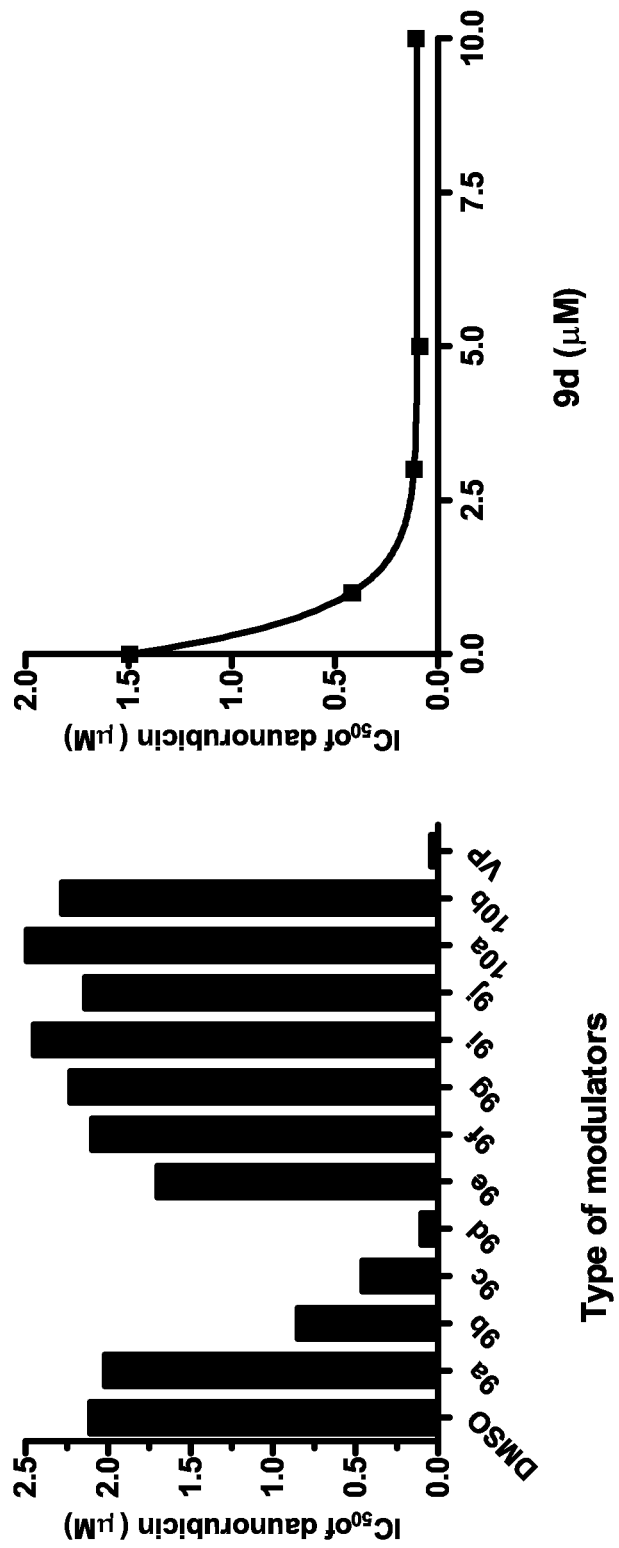

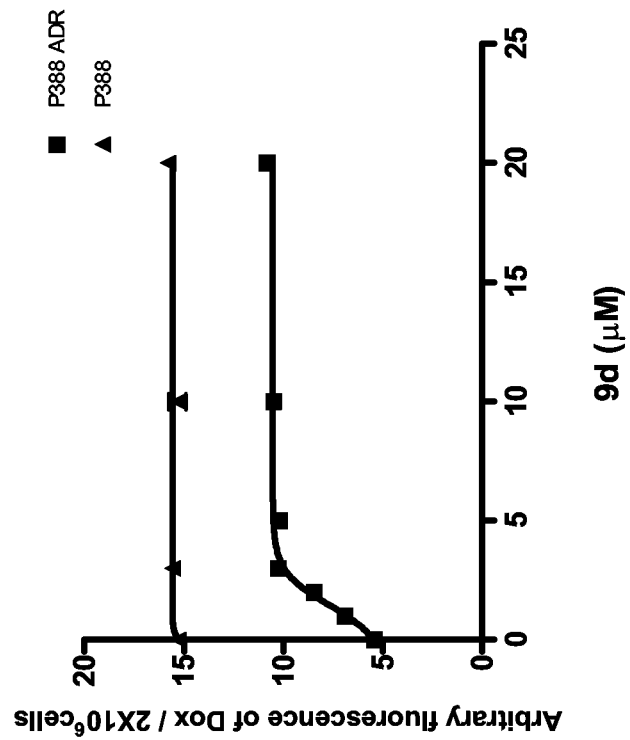
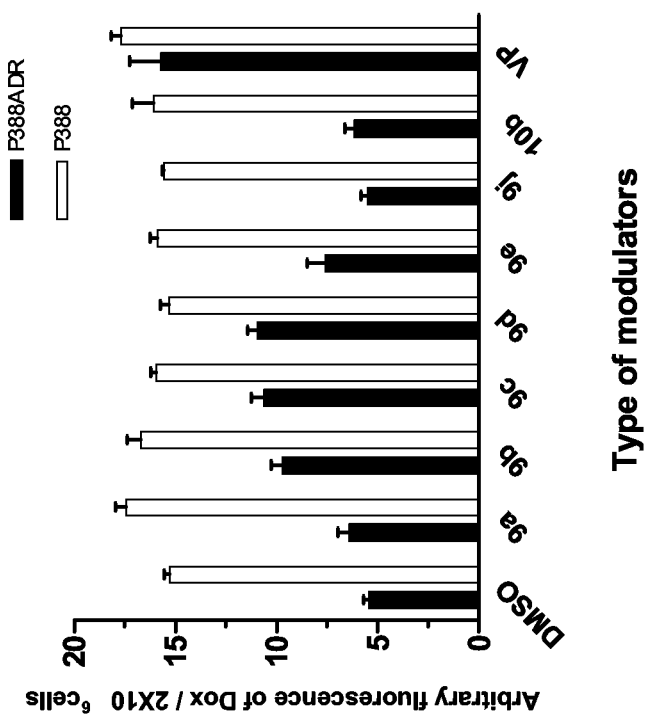

FLAVONOID DIMERS AND METHODS OF MAKING AND USING SUCH

FIELD OF THE INVENTION

This invention relates to compounds and method of reducing P-glycoprotein based multidrug resistance, and the synthesis of these compounds.

BACKGROUND OF THE INVENTION

Drug Resistance in Cancer Chemotherapy

Multidrug resistance (MDR) is a major problem in cancer chemotherapy. The best characterized resistance mechanism is the one mediated by the overexpression of drug efflux transporters, permeability-glycoprotein (P-gp), which pump a variety of anticancer drugs out of the cells, resulting in lowered intracellular drug accumulation. It is believed that the extrusion of drugs by P-gp is mediated by conformational changes. Development of reversing or modulating agent against P-gp has attracted interests from both academia and industry. Tsuruo et al (Overcoming of vincristine resistance in P388 leukemia in vivo and in vitro through enhanced cytotoxicity of vincristine and vinblastine by verapamil (*Cancer Res* 1981, 41, 1967-1972) first reported that verapamil, a calcium channel blocker, could reverse resistance by inhibiting P-gp-mediated drug efflux. Since then, there is considerable in vitro data suggesting that MDR due to P-gp can be effectively modulated by a range of compounds including dexverapamil[21], dexniguldipine[22], PSC 833 (Resistance modification by PSC-833, a novel non-immunosuppressive cyclosporin. *Eur J Cancer* 1991, 27, 1639-1642) and VX-710 (BIRICODAR (VX-710; Incel): an effective chemosensitizer in neuroblastoma. *Br J Cancer* 1999, 80, 1190-1196). Although these so called second generation MDR modulators showed some encouraging results, their uses are limited by their unpredictable pharmacokinetic interactions with the anticancer drugs (MDR expression in normal tissues. Pharmacologic implications for the clinical use of P-glycoprotein inhibitors. *Hematol Oncol Clin North Am* 1995, 9, 319-336). The third generation MDR modulators developed by structure-activity relationships and combinatorial chemistry approaches include zosuquidar LY335979, tariquidar XR9576, laniquidar R101933, the acridonecarboxamide GF120918 and the substituted diarylimidazole ONT-090, which are currently being evaluated under clinical trials.

A promising family of compounds as MDR modulators is the flavonoids because flavonoids have generally low toxicity. The flavonoids are natural occurring compounds in fruits and vegetables, which constitute a normal component of human food. They also show varying effects on MDR depending on the type of cell and the drug used. Chrysin (1), quecetin (2), kaempferol (3) and dehydrosilybin (4) (FIG. 1*a*) were reported to bind directly to the NBD2 cytosolic domain of mouse P-gp (Modulation by flavonoids of cell multidrug resistance mediated by P-glycoprotein and related ABC transporters. *CMLS, Cell. Mol. Life. Sci.* 2002, 59, 307-322.). Increased hydrophobicity through the introduction of prenyl or other alkyl groups into the flavonoid structure often produced more efficient inhibitors. 8- or 6-Prenylchrysin (5 or 6) (FIG. 1*a*) inhibited P-gp mediated drug efflux within leukemic K562/R7 cells, whereas 8-dimethylallylkaempferide (7) was a better modulator than either cyclosporine A or verapamil in the inhibition of Ltrmdr1.

Even with their low toxicity, the current generation of flavonoid modulators has limitations. The first is that their activities tend to be moderate. Secondly, they have a broad spectrum of biological activities including anti-estrogen and inhibition of other ATPases. High dosage application of flavonoids as MDR modulators is likely to lead to side effects.

Drug Resistance in Treating Parasitic Diseases

Leishmaniasis, one of the six major parasitic diseases targeted by the World Health Organization (WHO), is endemic in 88 countries around the world. Most leishmaniasis occurs in northern Africa, Asia, Latin America and the Middle East. There are 350 million people at risk of infection with 2 million cases reported annually. About a quarter of these cases are visceral leishmaniasis, which could be lethal. The primary treatment of leishmaniasis is by the administration of pentavalent antimonials (Pentostam and Glucantime). Secondary treatment includes pentamidine and amphotericin B. These treatments have many side effects and their efficacies are further impeded by the emergence of clinical resistance to some of these antileishmanials (Human leishmaniasis: clinical, diagnostic, and chemotherapeutic developments in the last 10 years. *Clin. Infect. Dis.* 1997, 24, 684-703). It has been reported that more than 50% of the visceral leishmaniasis cases in India are resistant to the antimonials (Circulating T helper 1 (Th1) cell- and Th2 cell-associated cytokines in Indian patients with visceral leishmaniasis. *Am. J. Trop. Med. Hyg.* 1997, 56, 522-5). The WHO has set the pentavalent antimonials resistance in *Leishmania* as one of its top priorities. Newer treatment like miltefosine, a hexadecylphosphocholine, has also shown tremendous promises. However due to the long half-life in blood, treatment with miltefosine can easily lead to drug resistance. Therefore there is a need to develop new drug that can treat parasitic diseases showing multi-drug resistance.

OBJECTS OF THE INVENTION

Therefore, it is an object of this invention to develop flavonoid derivatives having improved activities and/or selectivity over flavonoid to resolve at least one or more of the problems as set forth in the prior art. As a minimum, it is an object of this invention to provide the public with a useful choice.

SUMMARY OF THE INVENTION

Accordingly, this invention provides a compound of formula I:

$$\text{flavonoid-linker-flavonoid} \qquad \qquad \text{I}$$

wherein
the flavonoid is selected from the group consisting of chalcone, flavone, flavonol, flavanone, anthocyanin, and isoflavonoid; and
the linker is a group having at least one carbon atom.

Preferably, the linker is selected from the group consisting of alkylene group, group having a plurality of ethylene glycol units, group having a plurality of propylene glycol units, group having plurality of o-phenylenedioxy, m-phenylenedioxy, or p-phenylenedioxy units, or their combinations.

More preferably, the linker is a group having a plurality of ethylene glycol units, which may have 1 to 13 ethylene glycol units. Advantageously, the linker has 2 to 4 or 6 ethylene glycol units, more preferably 4 ethylene glycol units.

The flavonoid in formula I may be flavanone, and more preferably apigenin.

It is another aspect of this invention to provide a method to synthesize the compound of above formula I, wherein
the flavonoid is flavanone; and
the linker is a group having a plurality of ethylene glycol units.

p-hydroxybenzaldehyde first reacts with a compound of formula II to form a compound of formula III

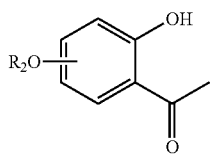

II

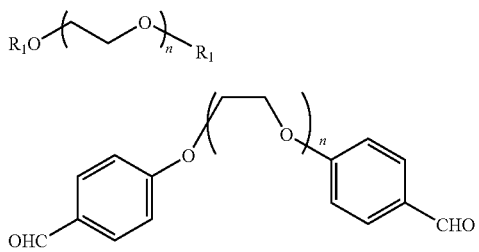

III wherein $R_1$ is selected from —H, -tosylate, and -mesylate.

Then the compound of formula III reacts with a compound of formula IV

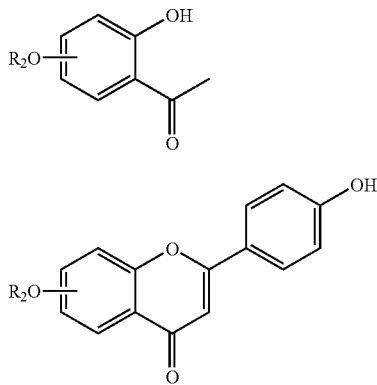

IV to form the compound of formula I, wherein $R_2$ is selected from the group consisting of —H, benzyl, and methoxymethyl.

This invention also provides an alternative method to synthesize the compound of formula I, wherein
the flavonoid is flavanone; and
the linker is a group having a plurality of ethylene glycol units.

p-hydroxybenzaldehyde first reacts with a compound of formula IV to form a compound of formula V

IV

V wherein $R_2$ is selected from the group consisting of —H, benzyl and methoxymethyl.

Then the compound of formula V reacts with a compound of formula II to form the compound of formula I

II wherein $R_1$ is selected from —H, -tosylate, and -mesylate.

It is yet another aspect of this invention to provide a method of reducing P-glycoprotein based multidrug resistance including the step of administering an effective amount of the compound of formula I:

flavonoid-linker-flavonoid    I wherein
the flavonoid is selected from the group consisting of chalcone, flavone, flavonol, flavanone, anthocyanin, and isoflavonoid; and
the linker is a group having at least one carbon atom.

It is a further aspect of this invention to provide a method of reducing resistance of a drug in a parasitic disease including the step of administering an effective amount of a compound of formula I, preferably in a concentration of 4 to 60 μM:

flavonoid-linker-flavonoid    I wherein
the flavonoid is selected from the group consisting of chalcone, flavone, flavonol, flavanone, anthocyanin, and isoflavonoid; and
the linker is a group having at least one carbon atom.

Preferably, the parasitic disease is caused by genus *Leishmania*. More preferably, the parasitic disease is caused by one of the parasites selected from the group consisting of *L. donovani, L. amazonensis, L. tarentolae, L. tropica, L. enriettii, L. mexicana,* and *L. major*.

Advantageously, the drug is selected from the group consisting of sodium stibogluconate and pentamidine, preferably in a concentration of 1 to 6.4 mg/mL.

It is another aspect of this invention to provide a medicament including any one of the flavonoid dimers mentioned above for reducing P-glycoprotein based multidrug resistance or for reducing resistance of a drug in cancer or a parasitic disease.

BRIEF DESCRIPTION OF THE DRAWINGS

Preferred embodiments of the present invention will now be explained by way of example and with reference to the accompanying drawings in which:

FIG. 3 shows the effects of apigenin monomers and dimers on taxol cytotoxicity in MDA435LCC6 MDR cells;

FIG. 4 shows the effects of apigenin monomers and dimers on vinblastine cytotoxicity in MDA435LCC6 MDR cells;

FIG. 8A shows the effects of apigenin monomers and dimers on doxorubicin cytotoxicity in P388/ADR cells, and FIG. 8B shows the concentration-dependent effect of 9d on doxorubicin cytotoxicity in P388/ADR cells, presented as $IC_{50}$ values calculated from dose-response curves of MTS cytotoxicity assays in the presence of different concentrations of 9d (0-10 μM);

FIG. 9A shows the effects of apigenin monomers and dimers on daunorubicin cytotoxicity in P388/ADR cells, and FIG. 9B Concentration-dependent effect of 9d on daunorubicin cytotoxicity in P388/ADR cells. The results are presented as $IC_{50}$ values calculated from dose-response curves of MTS cytotoxicity assays in the presence of different concentrations of 9d (0-10 μM);

FIG. 11 shows the intracellular accumulation of doxorubicin in P388/ADR and P388 cells by (A) different modulators and (B) different concentrations of 9d (0-20 μM);

DETAILED DESCRIPTION OF THE PREFERRED EMBODIMENTS

Figure 1A:
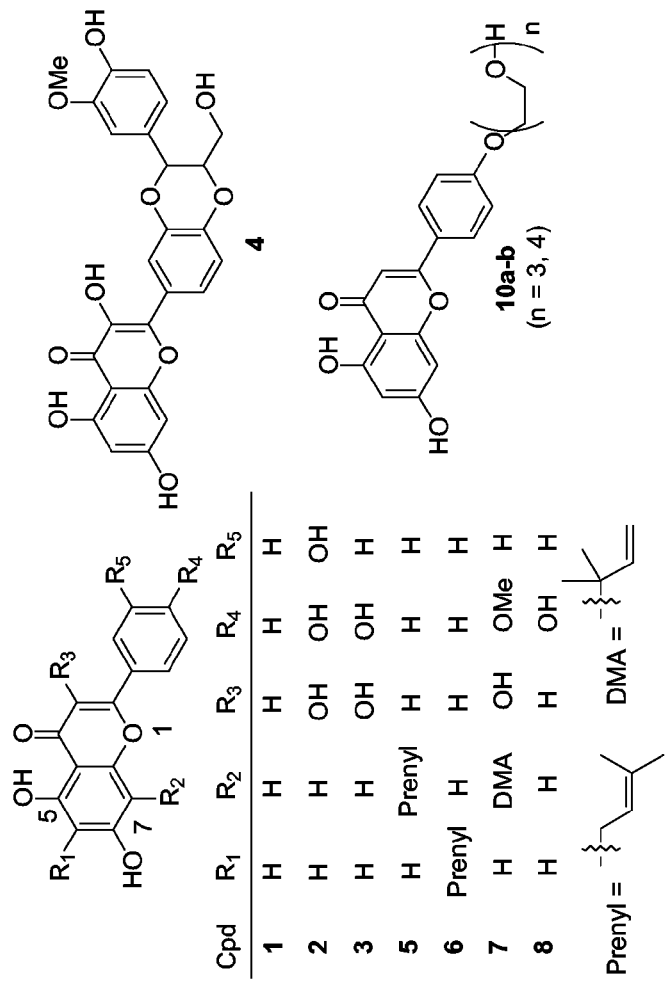
FIG. 1 shows the structures of known flavonoids (FIG. 1a), and the dimerized flavonoids of this invention (FIG. 1b)

This invention is now described by way of example with reference to the figures in the following paragraphs.

Objects, features, and aspects of the present invention are disclosed in or are obvious from the following description. It is to be understood by one of ordinary skill in the art that the present discussion is a description of exemplary embodiments only, and is not intended as limiting the broader aspects of the present invention, which broader aspects are embodied in the exemplary constructions.

The approach to improve the potency and selectivity of flavonoids of this invention is to take advantage of the pseudodimeric nature and the multiple binding sites of P-gp by using polyvalent interactions. Polyvalent interactions in biological systems are characterized by the simultaneous binding of multiple ligands on one biological entity. "Polyvalency" refers to a single molecule with one or more "ligands" that can simultaneously bind to one biological entity. Under the right conditions, polyvalent interactions are typically much stronger than the corresponding monovalent interactions due to the more favorable entropy of the second binding event. This approach aims to combine the advantages of flavonoids being a relatively safe P-gp reversing agent and the power of polyvalency in increasing the affinity of monomers.

In a broad sense of this invention, a compound of formula I is synthesized:

flavonoid-linker-flavonoid      I wherein the flavonoid is selected from the group consisting of chalcone, flavone, flavonol, flavanone, anthocyanin, and isoflavonoid; and the linker is a group having at least one carbon atom.

The term "flavonoid" refers to compounds based on a C15 skeleton with a CHROMANE ring bearing a second aromatic ring B in positions 2, 3 or 4.

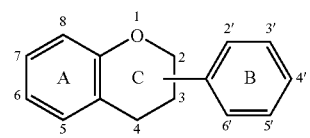

Various subgroups of flavonoids are classified according to the substitution patterns of ring C. Both the oxidation state of the heterocyclic ring and the position of ring B are important in the classification.

Examples of the 6 Major Subgroups are

1. Chalcones

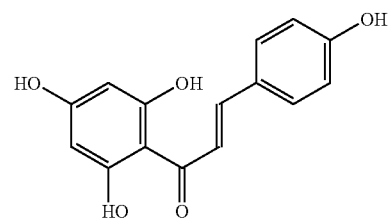 [SMILES: O=C(/C=C/c1ccc(O)cc1)c1c(O)cc(O)cc1O]

2. Flavone (generally in herbaceous families, e.g. Labiatae, Umbelliferae, Compositae).

Apigenin (*Apium graveolens, Petroselinum crispum*).

Luteolin (*Equisetum arvense*)

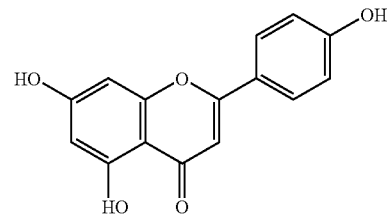 [SMILES: O=c1cc(-c2ccc(O)cc2)oc2cc(O)cc(O)c12]

3. Flavonol (generally in woody angiosperms)

Quercitol (*Ruta graveolens, Fagopyrum esculentum, Sambucus nigra*)

Kaempferol (*Sambucus nigra, Cassia senna, Equisetum arvense, Lamium album, Polygonum bistorta*).

Myricetin.

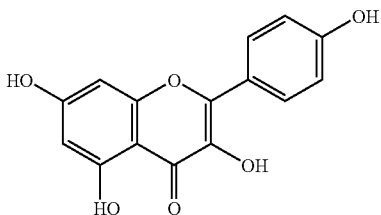 [SMILES: O=c1c(O)c(-c2ccc(O)cc2)oc2cc(O)cc(O)c12]

4. Flavanone

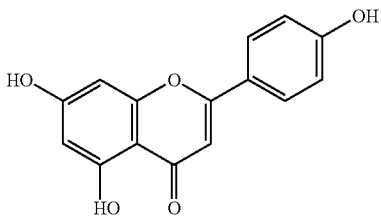 [SMILES: O=c1cc(-c2ccc(O)cc2)oc2cc(O)cc(O)c12]

5. Anthocyanins

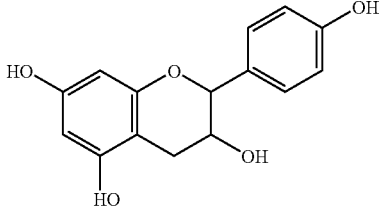 [SMILES: Oc1ccc(C2Oc3cc(O)cc(O)c3CC2O)cc1]

6. Isoflavonoids

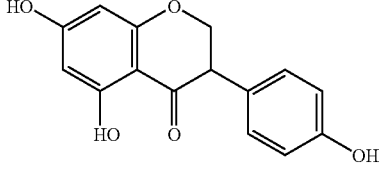 [SMILES: O=C1c2c(O)cc(O)cc2OCC1c1ccc(O)cc1]

All of the above compounds can be used as the "flavonoid" in the context of this invention. Various substitutions of the —H or —OH on the benzene ring or the 6-membered ring of the flavonoid are possible. For example, the —H or —OH may be substituted by the following groups:

halogen: fluorine, chlorine, bromine and iodine;

$C_1$-$C_{10}$ alkyl: straight-chain or branched alkyl groups having 1 to 10 carbon atoms, such as methyl, ethyl, propyl, 1-methylethyl, butyl, 1-methylpropyl, 2-methylpropyl, 1,1-dimethylethyl, pentyl, 2-methylbutyl;

$C_1$-$C_{10}$ haloalkyl: straight-chain or branched alkyl groups having 1 to 10 carbon atoms, it being possible for some or all of the hydrogen atoms in these groups to be replaced by halogen atoms as mentioned above, for example $C_1$-$C_{10}$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

$C_1$-$C_{10}$ alkoxy: straight-chain or branched alkyl groups having 1 to 10 carbon atoms as mentioned above, which are attached to the skeleton via an oxygen atom (—O—), for example $C_1$-$C_{10}$ alkoxy such as methyloxy, ethyloxy, propyloxy, 1-methylethyloxy, butyloxy, 1-methylpropyloxy, 2-methylpropyloxy, 1,1-dimethylethyloxy;

$C_2$-$C_{10}$ halo-alkoxy: straight-chain alkyl groups having 2 to 10 carbon atoms, it being possible for some or all of the hydrogen atoms in these groups to be replaced by halogen atoms as mentioned above, these groups being attached to the skeleton via an oxygen atom, for example 2-fluoroethyloxy, 2,2-difluoroethyloxy, 2,2,2-trifluoroethyloxy, 2-chloro-2-fluoroethyloxy, 2-chloro-2,2-difluoroethyloxy, 2,2-dichloro-2-fluoroethyloxy, and 2,2,2-trichloroethyloxy.

The term "partially or fully halogenated" is meant to express that in the groups characterized in this manner the hydrogen atoms may be partially or fully replaced by identical or different halogen atoms as mentioned above.

The hydrogen atoms or —OH groups on the benzene ring or the 6-membered ring of the flavonoid may be partially or fully replaced by amino groups bearing alkyl and aryl groups with different substitutions as above, nitro groups, thioether groups, sulfoxide or sulfone groups.

Furthermore, the —OH groups on the benzene ring or the 6-membered ring of the flavonoid may be protected by appropriate ester groups if desired, for example, the H of the —OH groups may be replaced by $C_1$-$C_6$ acyl having the structure —(CO)—R, wherein R is hydrogen or straight-chain or branched alkyl groups having 1 to 5 carbon atoms, such as methyl, ethyl, propyl, 1-methylethyl, butyl, 1-methylpropyl, 2-methylpropyl, 1,1-dimethylethyl, pentyl, 2-methylbutyl. The alkyl group R can be partially or fully halogenated". The term "partially or fully halogenated" is meant to express that in the groups characterized in this manner the hydrogen atoms may be partially or fully replaced by identical or different halogen atoms, for example chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl.

Various linker groups are possible to be utilized in this invention. Obvious the linker must have two ends with each end link to one of the flavonoids. The linker should have at least one carbon atom, including alkylene group (—$CH_2$-)n; groups having the general formula —O[—(—$CH_2$)$_m$—(O)]$_n$—, for example group having a plurality of ethylene glycol units —O—(—$CH_2$—$CH_2$—O)$_n$—, group having a plurality of propylene glycol units —O—($CH_2$—$CH_2$—$CH_2$—O)$_n$—; group having an o-phenylenedioxy, m-phenylenedioxy, or p-phenylenedioxy unit; or a combination of these or other groups that may link the flavonoids together by chemical bonds. Each of these groups can again be "partially or fully halogenated". It will be shown later that the linker group can have various lengths, that is, "m" and/or "n" can be any integer greater than or equal to 1.

It should be noted that the two flavonoids in formula I can be different. For example, one can be flavone, while the other one can be flavanone, and various other combinations are possible.

Further, the position of the linkage may be at various positions of the flavonoids. This is a matter of design choice during synthesis of the compounds and shall be determined by the person skilled in the art.

Suprisingly, the flavonoid dimer of this invention is found to be highly effective chemosensitizer in vitro. Some of the compounds are able to increase drug accumulation within drug resistant cells but not drug sensitive cells and enhance cytotoxicity of anticancer drugs (taxol, doxorubicin, daunomycin, vincristine and vinblastine) in drug resistant breast cancer and leukemia cells in vitro by 5-50 folds.

Figure 1B:
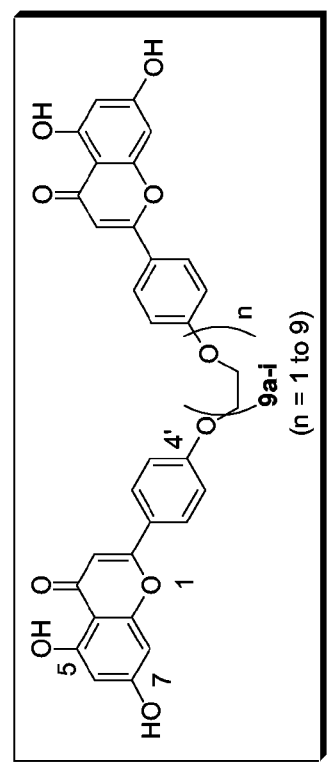

A series of flavonoid dimers with the flavonoids being apigenin (8) polyethylene glycol (PEG) chain of various lengths of general structure 9 have been synthesized (FIG. 1). Apigenin (8) is chosen as the parent monoligand because it has been reported to be a modulator of MDR in colon HCT-15 cancer cells. The C'4 position has been chosen as the point of attachment of the linker because substitution at this position has been shown to have little effect on the activity of the molecules. The potency of a series of apigenin dimers is investigated, linked with 1 to 13 ethylene glycol units, in sensitizing different MDR cancer cells. Their activities are compared with apigenin itself as well as the monomers 10a and 10b. We have also evaluated their ability to reverse drug efflux mediated by P-gp.

Synthesis of Polyethylene Glycol Linked Apigenin Dimers
Chemistry

Figure 2:
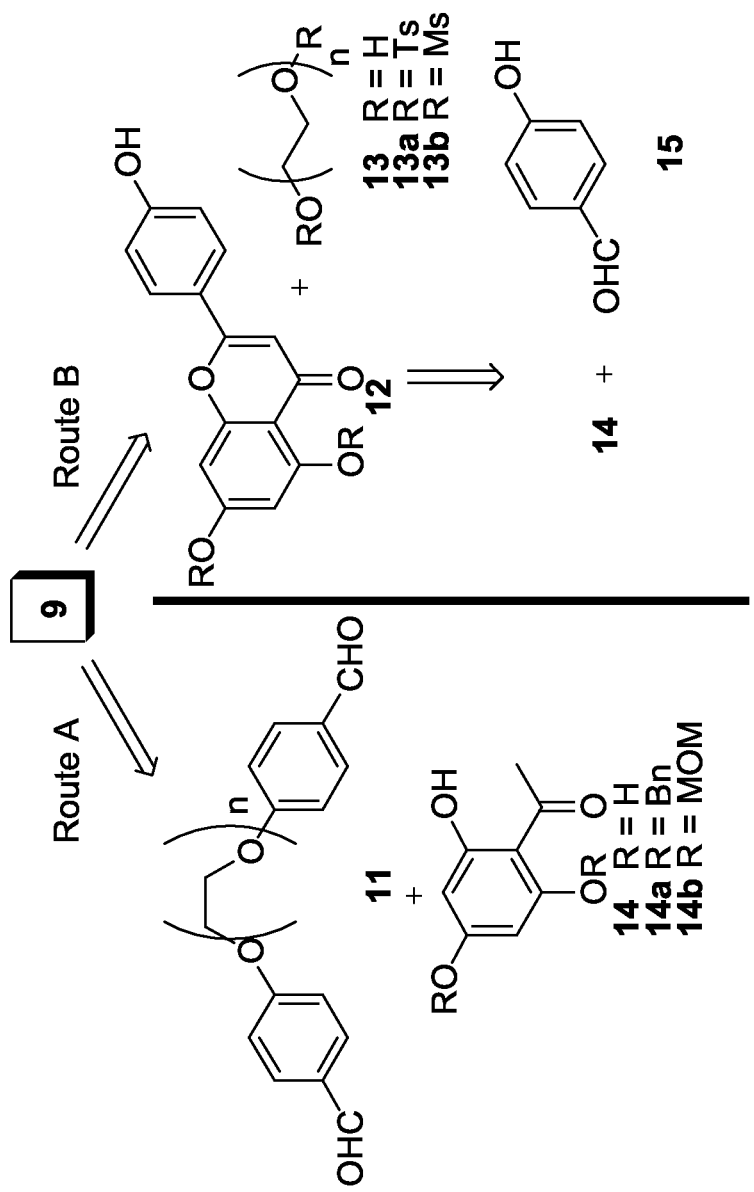
FIG. 2 shows the retrosynthetic analysis of the synthesis of apigenin dimers via two pathways.

There are two synthetic pathways, which could be exploited to achieve the synthesis of polyeythleneglycol (PEG)-linked flavonoids 9, as shown in FIG. 2. The first approach (Route A) involves the employment of a series of PEG-linked bis-aldehydes 11, which were synthesized from aldehyde 15 and corresponding ethylene glycol ditosylate 13a or dimesylate 13b according to "Synthesis of a ditopic cyclophane based on the cyclobutane ring by chalcone photocycloaddition. *Tetrahedron* 2003, 59, 3455-3459". Then aldol condensation of the bis-aldehyde 11 with trihydroxyacetophenone 14, followed by oxidative cyclization of bis-chalcone to flavone, should furnish 9. The other pathway (Route B) involved the synthesis of selectively protected flavonoid 12, which is then coupled with activated PEG chains 13a or 13b. The flavonoid 12 can in turn be derived from trihydroxyacetophenone 14 and benzaldehyde 15.

PEG chains 13 are commercially available up to n equal to six. PEGs with n larger than six are not readily available commercially and hence they were required to be synthesized. PEGs with n larger than six can be obtained by methods described in "An expedient synthesis of monodispersed oligo (ethylene glycols). *Synthesis* 2004, 7, 1007-1010". Ethylene glycol ditosylates 13a (for n=2, 3) and dimesylate 13b (for n=1, 4 to 9) were prepared from the corresponding PEG chains 13, tosyl chloride or methanesulfonyl chloride and triethylamine in dichloromethane at ice-bath temperature according to the methods described in "Synthesis of orthogonal end functionalized oligoethylene glycols of defined lengths. *Tetrahedron Lett.* 2004, 45, 4285-4288". Both compounds trihydroxyacetophenone 14 and benzaldehyde 15 are commercially available. Protected 2-hydroxyacetophenone 14a (Synthesis of a 3,4,5-trimethoxybenzoyl ester analogue of epigallocatechin-3-gallate (EGCG): A potential route to the natural product green tea catechin, EGCG. *Org. Lett.* 2001, 3, 843-846) and 14b (An effective synthesis of isoorientin: the regioselective synthesis of a 6-C-glucosylflavone. *Carbohydrate Research* 2000, 329, 507-513) can be prepared according to the methods described in the respective references. Prior to attempting the synthesis of other target compounds, flavonoid 9a (n=1) was chosen as model study to ascertain the optimal conditions for synthesis.

Synthesis of 9a (N=1) Via Route A

The synthesis of 9a was prepared according to Route A. The results are summarized in Scheme 1. p-Hydroxybenzaldehyde (15) was coupled with ethylene glycol dimesylate (13b) in the presence of potassium carbonate in 50% acetonitrile (ACN) in water at refluxing temperature to furnish bis-aldehyde 11a in high yield. Then the bis-chalcone 16 was prepared from aldol condensation of the bis-aldehyde 11a with dibenzyl-protected acetophenone 14a under basic medium. Initial attempts to synthesize bis-chalcone 16 were frustrated by low conversion, slow reaction rate and problematic isolation of the products. We attributed the difficulty to the low solubility of the aldehyde in the reaction medium. After a great deal of experimentation, it was found that by dissolving the bis-aldehyde 11a in THF and adding this to a solution of acetophenone 14a in 60% aqueous KOH solution, near quantitative conversion to the desired bis-chalcone could be achieved. The bis-chalcone 16 has a characteristic golden yellow color. The large coupling constant of the olefinic protons (J=16 Hz) indicated that the carbon-carbon double bond is in trans manner. Cyclization of bis-chalcone 16 to bis-flavonoid 17 proceeded smoothly in one pot via a cyclization-elimination route using a catalytic amount of iodine in dimethyl sulfoxide (DMSO) under thermal condition. It should be stressed that the presence of larger than catalytic quantities of iodine resulted in the cleavage of benzyl group as well as iodination of the phenyl ring. Best results were obtained when larger than 100 mg of the starting bis-chalcone were used in the reaction. Amongst the methods used for deprotection of the benzyl group in 17 are hydrogen transfer hydrogenolysis, and catalytic amount of Pd(OH)$_2$ on charcoal or Pd/C under an atmosphere of hydrogen. However these were not successful and only starting material was ever recovered. After many variations of reaction condition, flavonoid 9a was finally achieved in very low yield by employing large amount of 10% Pd/C in THF/water mixture. The use of benzyl group as protecting group thus seems problematic and the overall yield was poor. Hence the methoxymethyl (MOM) group was chosen to replace benzyl group and the whole synthetic pathway was repeated from bis-aldehyde 11a (Scheme 1).

Bis-chalcone 16a was obtained in high yield by aldol condensation of bis-aldehyde 11a with diMOM-protected acetophenone 14b using 3M KOH solution in EtOH. Cyclization of bis-chalcone 16a to flavone using catalytic amount of iodine in DMSO was a failure. On the other hand, 2,3-dichloro-5,6-dicyano-1,4-benzoquinone (DDQ) mediated oxidative cyclization under thermal condition proceeded to furnish 17a with the cleavage of one MOM group. Tedious chromatographic purification of the reaction mixture resulted in low yield of 17a. Conversion of 17a to the flavonoid 9a was achieved by acidic medium deprotection of MOM group. These results suggested that the use of MOM group for protection was superior to the benzyl group, since the MOM group can be cleaved readily under mild conditions. However, the yield of the overall conversion of 15 to 9a was still low. Re-optimization of the whole synthetic scheme was necessary.

Scheme 1.

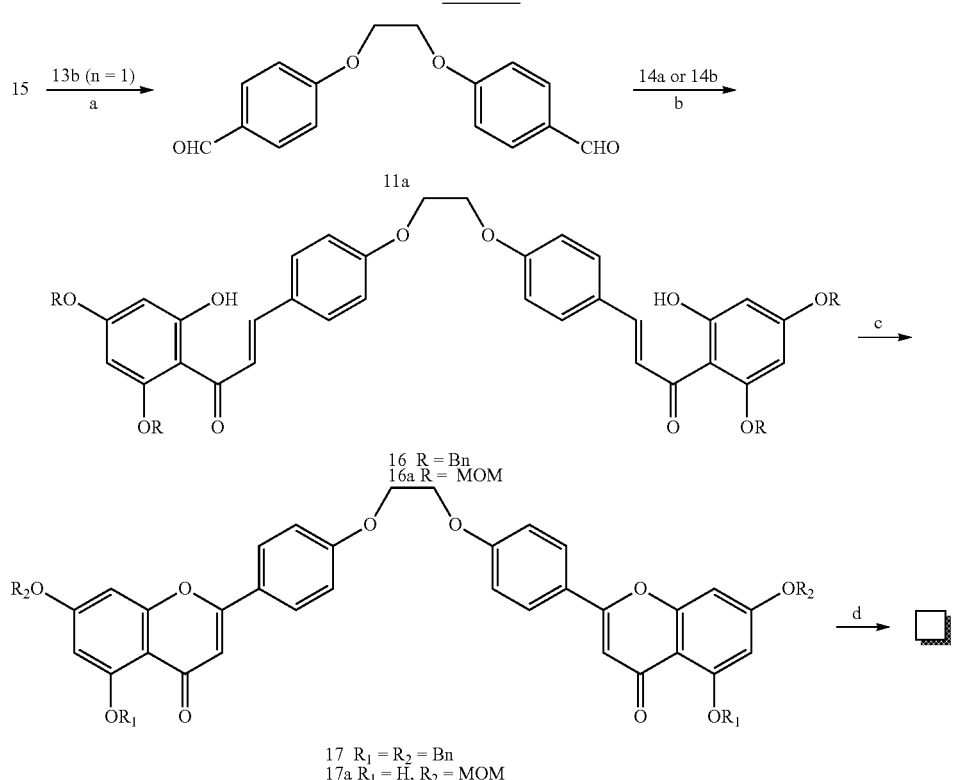

a K₂CO₃, ACN/H₂O, reflux, 14 h;
b For 16, 14a, 60% KOH, r.t., 14 h; For 16a, 14b, 3M KOH in EtOH, r.t., 14 h;
c For 17, cat. I₂, DMSO, reflux, 14 h; For 17a, DDQ, PhMe/dioxane, reflux, 14 h;
d From 17, H₂, Pd/C, THF/H₂O, r.t., 14 h; From 17a, 80% AcOH, reflux, 14 h.

Synthesis of 9a (n=1) Via Route B

The synthesis of 9a was then investigated according to Route B. The results are summarized in Scheme 2. The acetophenone 14b was condensed with p-allyloxybenzaldehyde under basic medium to yield chalcone 18 in high yield. DDQ mediated oxidative cyclization of 18 proceeded to furnish 19 with the cleavage of one MOM group. Protection of the hydroxy group in 19 with benzyl bromide using potassium carbonate in DMF gave 20 in good yield. The allyl protecting group of 20 was cleaved using catalytic amount of Pd(PPh₃)₄ and potassium carbonate in methanol to furnish 12a in high yield. The intermolecular nucleophilic substitution of dimesylate 13b (n=1) by the para-phenoxy moiety of 12a under basic conditions gave 21a. The dimeric nature of 21a was evident from the high-resolution mass spectrum. Palladium catalyzed deprotection of benzyl groups followed by acidic deprotection of MOM groups gave flavanoid 9a in high yield.

Scheme 2.

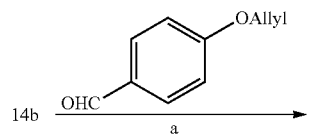

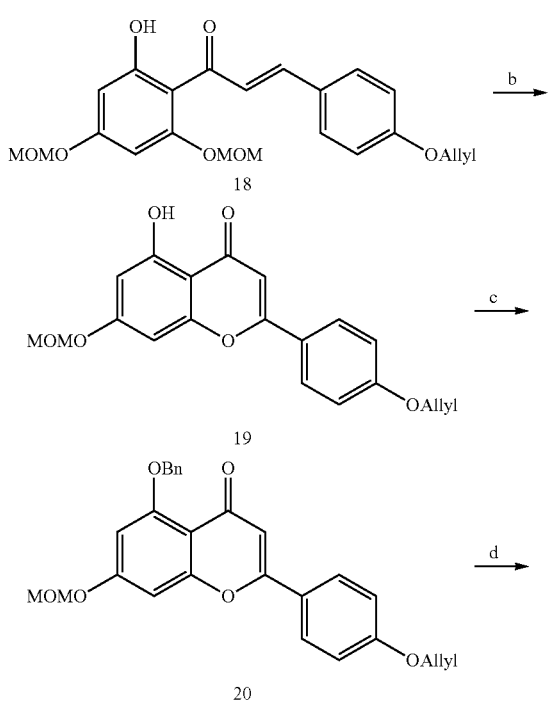

13
-continued

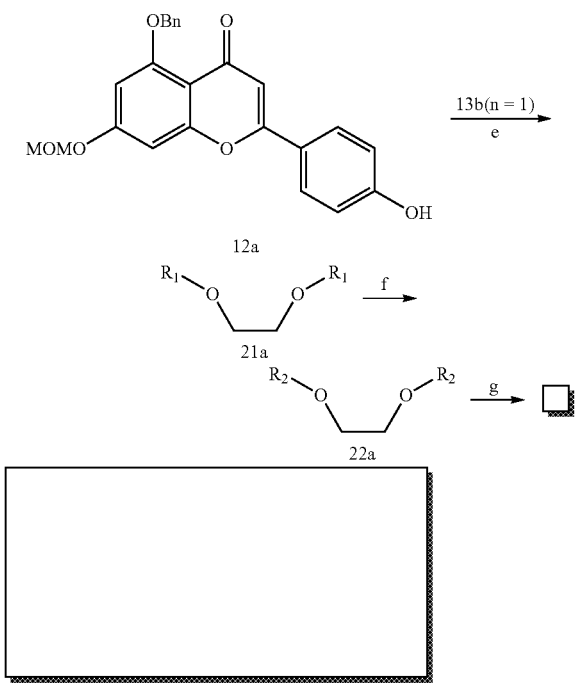

a 3M KOH in EtOH, r.t., 16 h;
b DDQ, PhMe/dioxane, reflux, 7 h;
c K$_2$CO$_3$, BnBr, DMF, reflux, 2 h;
d cat. Pd(PPh$_3$)$_4$, K$_2$CO$_3$, MeOH, reflux, 2 h;
e K$_2$CO$_3$, DMF, reflux, 2 h;
f H$_2$, Pd/C, CHCl$_3$, r.t., 12 h;
g 80% AcOH, reflux, 14 h.

14

Synthesis of Flavone Dimers 9b to 9i Via Route B

Having established the optimal conditions for the synthesis of 9a via Route B, other flavonoid dimers with different PEG chains were synthesized in similar manner. The results are summarized in Scheme 3. For the shorter chains (n=2 and 3), the PEG ditosylates (13a) were used whereas for the longer chains (n=4-9), the PEG dimesylates (13b) were used. In all cases, the flavonoid dimers 9a to 9l were prepared in reasonable overall yields, in the range of 30-50% based on 12a. In general, the flavonoid dimers with longer PEG chains (n=5 or more) were obtained as oil. For flavonoid dimers with shorter PEG chain lengths (n=4 or less), they were obtained as solid with melting point decreasing from 352° C. (n=1) to 131° C. (n=4).

Synthesis of Monovalent Flavonoids 10a and 10b

In the course of subsequent biological studies, it became evident that the monovalent flavonoids 10 were required for the purpose of control experiments. Fortuitously, in the coupling of 12a with the ditosylate 13a (n=3) or the dimesylate 13b (n=4), the mono-coupled product 23a (n=3) or 23b (n=4) were obtained as a minor side product presumably because of the hydrolysis of one of the tosylate or mesylate groups during the reaction. The monomeric nature of 23a and 23b was evident from the high-resolution mass spectra. Subsequential palladium catalyzed deprotection of the benzyl groups followed by acid deprotection of the MOM groups gave the monovalent flavonoids 10a and 10b (Scheme 3).

Scheme 3.

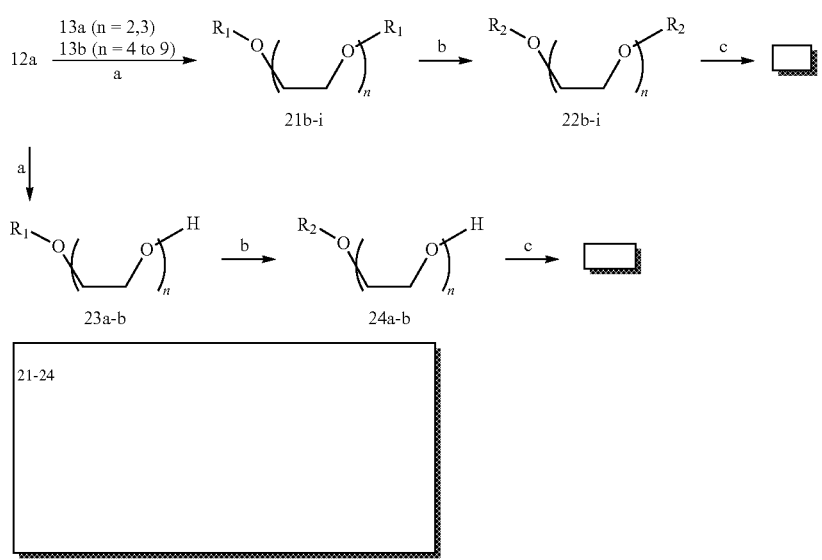

For n = 3, 4
a K$_2$CO$_3$, DMF, reflux;
b H$_2$, Pd/C, CHCl$_3$, r.t.;
c For n = 2, 3; 80% AcOH, reflux; For n = 4 to 9; 6 M HCl, THF, r.t.

Synthesis of Polyethylene Glycol Linked Apigenin Analog Dimers

Using the general approach developed via Route B, a number of apigenin analog dimers (35a-l) can be prepared starting from various substituted hydroxyacetophenones (31a-l) according to Scheme 4. Unsymmetrical apigenin dimers can also be prepared by the coupling of one of the monomer analog 34a-l with the mesylate of the monovalent apigenin 24 followed by deprotection.

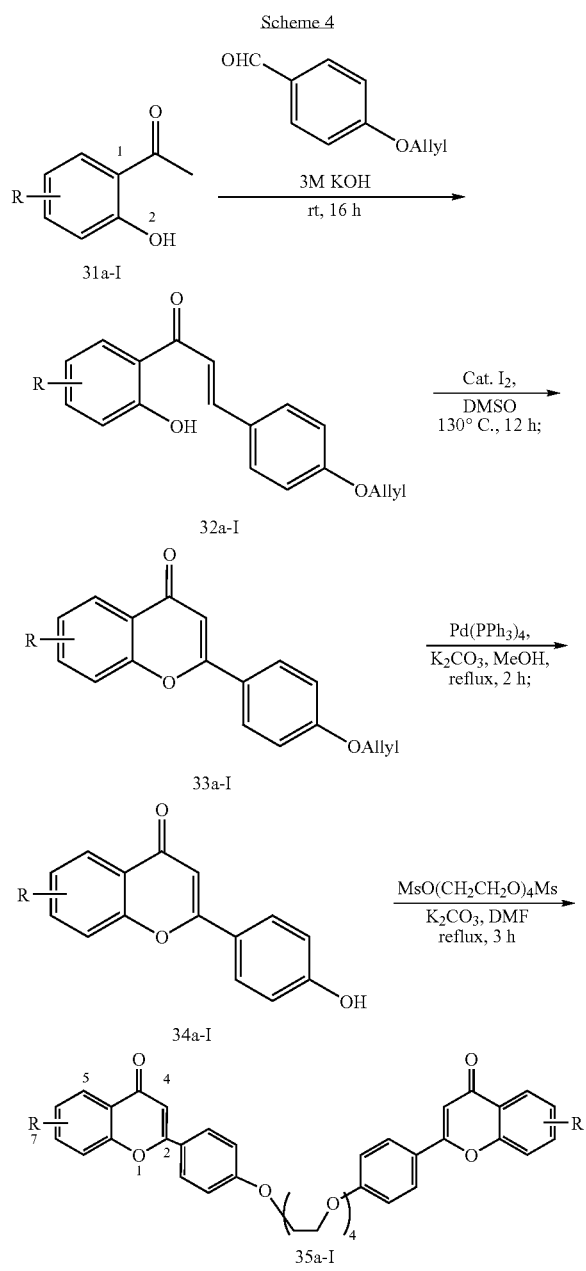

| For compounds 31 to 34: | | For compound 35 | |
|---|---|---|---|
| a R = H | g R = 4-Me | a R = H | g R = 7-Me |
| b R = 4-F | h R = 5-Me | b R = 7-F | h R = 6-Me |
| c R = 5-F | i R = 4-MeO | c R = 6-F | i R = 7-MeO |
| d R = 5-Cl | j R = 5-MeO | d R = 6-Cl | j R = 6-MeO |
| e R = 5-Br | k R = 6-MeO | e R = 6-Br | k R = 5-MeO |
| f R = 3,5-diCl | l R = 4,5-diMeO | f R = 6,8-diCl | l R = 6,7-diMeO |

A series of apigenin based flavonoid dimers have been synthesized in this invention, which were linked together by polyethylene glycol chain of various lengths via two synthetic routes. The use of MOM group for protection was found to be superior to the benzyl group, since the MOM group can be cleaved readily under mild conditions. This may be usefully applied in the synthesis of other flavonoid compounds.

Experimental Data

General. All NMR spectra were recorded on a Bruker MHz DPX400 spectrometer at 400.13 MHz for $^1$H and 100.62 MHz for $^{13}$C. All NMR measurements were carried out at room temperature and the chemical shifts are reported as parts per million (ppm) in δ unit relative to the resonance of $CDCl_3$ (7.26 ppm in the $^1$H, 77.0 ppm for the central line of the triplet in the $^{13}$C modes, respectively). Low-resolution and high-resolution mass spectra were obtained on a Micromass Q-TOF-2 by electron spray ionization (ESI) mode or on Finnigan MAT95 ST by electron ionization (EI) mode. Melting points were measured using Electrothermal IA9100 digital melting point apparatus and were uncorrected. All reagents and solvents were reagent grade and were used without further purification unless otherwise stated. The plates used for thin-layer chromatography (TLC) were E. Merck Silica Gel 60F$_{254}$ (0.25-mm thickness) and they were visualized under short (254-nm) UV light. Chromatographic purifications were carried out using MN silica gel 60 (230-400 mesh).

Trans-3-(4-allyloxyphenyl)-1-[2,4-bis(methoxymethoxy)-6-hydroxyphenyl]propenone (18): To a round-bottom flask was charged with 2-hydroxy-4,6-bis(methoxymethoxy)acetophenone 14b (4.39 g, 17.1 mmol), 4-allyloxybenzaldehyde (2.90 g, 17.9 mmol) and KOH solution (3 M solution in 96% EtOH, 30 mL). The solution turned brown immediately and was stirred at room temperature for 16 h. When TLC indicated complete consumption of acetophenone, the reaction mixture was poured into a separating funnel containing 0.5 M HCl solution (180 mL). The mixture was extracted with $CH_2Cl_2$ (40 mL×3). The combined organic layers were dried over $MgSO_4$, filtered and evaporated to give a crude brown oil, which was subjected to flash column chromatography (20% EtOAc in hexane) on silica gel (70 g) to furnish chalcone 18 (6.53 g, 95%) as yellow solid: m.p.: 70-71° C.; $^1$H NMR ($CDCl_3$) δ 3.48 (s, 3H), 3.53 (s, 3H), 4.57 (d, J=5.2 Hz, 2H), 5.18 (s, 2H), 5.28 (s, 2H), 5.31 (d, J=10.4 Hz, 1H), 5.42 (dd, J=1.2, 17.2 Hz, 1H), 6.02-6.04 (m, 1H), 6.24 (d, J=2.0 Hz, 1H), 6.31 (d, J=2.0 Hz, 1H), 6.93 (d, J=8.8 Hz, 2H), 7.54 (d, J=8.8 Hz, 2H), 7.76 (A of AB, J=15.4 Hz, 1H), 7.83 (B of AB, J=15.4 Hz, 1H), 13.9 (s, 1H); $^{13}$C NMR ($CDCl_3$) δ 56.4, 56.8, 68.8, 94.0, 94.7, 95.1, 97.5, 107.5, 115.1, 118.0, 125.0, 128.3, 130.0, 132.7, 142.6, 159.8, 160.4, 163.2, 167.2, 192.8; LRMS (ESI) m/z 401 (M$^+$+H, 100), 423 (M$^+$+Na, 22); HRMS (ESI) Calcd for $C_{22}H_{25}O_7$ (M$^+$+H) 401.1600, found 401.1604.

5-Hydroxy-7-methoxymethoxy-2-(4'-allyloxyphenyl)-4H-chromen-4-one (19): To a round-bottom flask was charged with chalcone 18 (6.53 g, 16.3 mmol), DDQ (5.56 g, 24.5 mmol) and a dry solvent of 25% dioxane in toluene (100 mL). The solution turned deep brown immediately and was stirred under nitrogen atmosphere at refluxing temperature for 7 h. When TLC indicated complete consumption of chalcone 18, the reaction mixture was cooled to room temperature and the solvents were evaporated to dryness. After addition of $CH_2Cl_2$ (150 mL), the insoluble brown solid was removed by suction filtration. The deep brown filtrate was washed with saturated $NaHCO_3$, dried over $MgSO_4$, filtered, evaporated and subjected to flash column chromatography (15% EtOAc in hexane) on silica gel (130 g) to furnish compound 19 (2.10 g, 36%) as pale yellow solid: m.p.: 100-101° C.; $^1$H NMR (CDCl$_3$) δ 3.49 (s, 3H), 4.59 (d, J=5.2 Hz, 2H), 5.22 (s, 2H), 5.32 (d, J=10.8 Hz, 1H), 5.43 (d, J=17.2 Hz, 1H), 6.00-6.09 (m, 1H), 6.44 (d, J=1.8 Hz, 1H), 6.54 (s, 1H), 6.25 (d, J=1.8 Hz, 1H), 6.99 (d, J=8.8 Hz, 2H), 7.79 (d, J=8.8 Hz, 2H), 12.74 (s, 1H); $^{13}$C NMR (CDCl$_3$) δ 56.4, 68.9, 94.2, 94.2, 100.0, 104.2, 106.1, 115.1, 118.2, 123.5, 127.9, 132.4, 157.5, 161.6, 161.9, 162.8, 163.9, 182.4; LRMS (ESI) m/z 355 (M$^+$+H, 36); HRMS (ESI) Calcd for C$_{20}$H$_{19}$O$_6$ (M$^+$+H) 355.1182, found 355.1164.

5-Benzyoxy-7-methoxymethoxy-2-(4'-allyloxyphenyl)-4H-chromen-4-one (20): To a round-bottom flask was charged with compound 19 (2.24 g, 6.3 mmol), benzyl bromide (1.70 g, 9.9 mmol), K$_2$CO$_3$ (1.80 g, 13.0 mmol) and DMF (15 mL). The reaction mixture was stirred at refluxing temperature for 2 h. When TLC indicated complete consumption of 19, the reaction mixture was poured into a separating funnel containing water (200 mL). The mixture was extracted with CH$_2$Cl$_2$ (30 mL×3). The combined organic layers were dried over MgSO$_4$, filtered and evaporated to give a brown oil, which was subjected to flash column chromatography with gradient elution (30% EtOAc in hexane to 60% EtOAc in hexane) on silica gel (50 g) to furnish compound 20 (2.01 g, 72%) as off-white solid: m.p.: 120-122° C.; $^1$H NMR (CDCl$_3$) δ 3.68 (s, 3H), 4.78 (d, J=5.2 Hz, 2H), 5.41 (s, 2H), 5.43 (s, 2H), 5.51 (d, J=10.8 Hz, 1H), 5.62 (d, J=17.2 Hz, 1H), 6.21-6.26 (m, 1H), 6.69 (d, J=2.0 Hz, 1H), 6.77 (s, 1H), 6.94 (d, J=2.0 Hz, 1H), 7.18 (d, J=8.6 Hz, 2H), 7.45 (t, J=7.6 Hz, 1H), 7.58 (dd, J=7.2, 7.6 Hz, 2H), 7.82 (d, J=7.2 Hz, 2H), 7.99 (d, J=8.6 Hz, 2H); $^{13}$C NMR (CDCl$_3$) δ 56.4, 68.9, 7.07, 94.3, 96.0, 98.7, 107.6, 110.2, 115.0, 118.1, 123.9, 126.6, 127.6, 128.5, 128.7, 132.6, 136.4, 159.4, 159.6, 160.7, 161.0, 161.2, 177.4; LRMS (ESI) m/z 445 (M$^+$+H, 100), 467 (M$^+$+Na, 15); HRMS (ESI) Calcd for C$_{27}$H$_{25}$O$_6$ (M$^+$+H) 445.1651, found 445.1641.

5-Benzyloxy-7-methoxymethoxy-2-(4'-hydroxyphenyl)-4H-chromen-4-one (12a): To a round-bottom flask was charged with compound 20 (2.01 g, 4.5 mmol), catalytic amount of Pd(PPh$_3$)$_4$ (0.1 g), K$_2$CO$_3$ (2.50 g, 18.1 mmol) and MeOH (80 mL). The reaction mixture was stirred at refluxing temperature for 2 h. When TLC indicated complete consumption of 20, the reaction mixture was poured into a beaker containing water (200 mL). The solution was acidified to pH 4 using 1 M HCl solution and numerous off-white solid was formed, which was collected by suction filtration. The collected solid was dissolved in 50% EtOAc in MeOH and the insoluble dark charcoal was removed by filtration. The brown filtrate was evaporated under reduced pressure and compound 12a (1.42 g, 78%) slowly precipitated out as white solid: m.p.: 202-204° C.; $^1$H NMR (d$_6$-DMSO) δ 3.59 (s, 3H), 5.40 (s, 2H), 5.51 (s, 2H), 6.77 (s, 1H), 6.85 (d, J=1.8 Hz, 1H), 7.07 (d, J=1.8 Hz, 1H), 7.09 (d, J=8.8 Hz, 2H), 7.49 (t, J=7.6 Hz, 1H), 7.58 (dd, J=7.2, 7.6 Hz, 2H), 7.79 (d, J=7.2 Hz, 2H), 8.06 (d, J=8.8 Hz, 2H), 10.41 (s, 1H); $^{13}$C NMR (d$_6$-DMSO) δ 56.5, 70.3, 94.4, 96.2, 99.1, 106.6, 109.6, 116.3, 121.7, 127.3, 127.9, 128.3, 128.7, 137.3, 159.2, 159.4, 160.7, 161.0, 161.2, 176.1; LRMS (ESI) m/z 405 (M$^+$+H, 100), 427 (M$^+$+Na, 19); HRMS (ESI) Calcd for C$_{24}$H$_{21}$O$_6$ (M$^+$+H) 405.1338, found 405.1336.

General procedure for the synthesis of flavonoid diners 21a-i from 12a: To a round-bottom flask was charged with compound 12a (1.6 equiv), dimesylate 13b (for n=1, 4 to 9) or ditosylate 13a (n=2, 3) (1 equiv.), K$_2$CO$_3$ (8 equiv) and DMF. The reaction mixture was stirred at refluxing temperature for 2 to 3 h. During heating, the reaction mixture turned slowly from pale brown to milky in color. When TLC indicated complete consumption of 12a, the reaction mixture was poured into a separating funnel containing water (200 mL). The mixture was extracted with CH$_2$Cl$_2$ (20 mL×3). If the mixture could not be separated into two layers, 1M HCl (20 mL) was added. The combined organic layers were dried over MgSO$_4$, filtered and evaporated to give a crude reaction mixture. Purification of the flavonoid dimer was performed by crystallization or flash column chromatography as indicated below.

1,4-Bis[4'-((5-benzyloxy-7-methoxymethoxy)-4H-chromen-4-on-2-yl)phenyl]-1,4-dioxabutane (21a): This compound was prepared from 12a (230 mg, 0.57 mmol), ethylene glycol dimesylate (75 mg, 0.34 mmol), K$_2$CO$_3$ (380 mg) and DMF (8 mL) as the general procedure for the synthesis of flavonoid dimers described above. After crystallization from EtOAc, the titled compound (150 mg, 63%) was obtained as white solid: m.p.: 173-175° C.; $^1$H NMR (CDCl$_3$) δ 3.50 (s, 6H), 4.40 (s, 4H), 5.23 (s, 4H), 5.25 (s, 4H), 6.51 (d, J=1.6 Hz, 2H), 6.57 (s, 2H), 6.77 (d, J=1.6 Hz, 2H), 7.04 (d, J=8.8 Hz, 4H), 7.30 (t, J=7.2 Hz, 2H), 7.39 (dd, J=7.2, 7.6 Hz, 4H), 7.63 (d, J=7.6 Hz, 4H), 7.83 (d, J=8.8 Hz, 4H); $^{13}$C NMR (CDCl$_3$) δ 56.4, 66.5, 70.7, 94.3, 96.0, 98.8, 107.7, 110.2, 114.9, 124.3, 126.6, 127.6, 127.7, 128.5, 136.4, 159.4, 159.6, 160.6, 160.9, 161.3, 177.4; LRMS (ESI) m/z 835 (M$^+$+H, 100), 857 (M$^+$+Na, 68); HRMS (ESI) Calcd for C$_{50}$H$_{42}$O$_{12}$Na (M$^+$+Na) 857.2574, found 857.2571.

1,7-Bis[4'-((5-benzyloxy-7-methoxymethoxy)-4H-chromen-4-on-2-yl)phenyl]-1,4,7-trioxaheptane (21b): This compound was prepared from 12a (200 mg, 0.50 mmol), diethylene glycol ditosylate (130 mg, 0.31 mmol), K$_2$CO$_3$ (360 mg) and DMF (8 mL) as the general procedure for the synthesis of flavonoid dimers described above. After crystallization from EtOAc, the titled compound (88 mg, 40%) was obtained as white solid: m.p.: 110-111° C.; $^1$H NMR (CDCl$_3$) δ 3.48 (s, 6H), 3.96 (t, J=4.6 Hz, 4H), 4.22 (t, J=4.6 Hz, 4H), 5.26 (s, 8H), 6.47 (d, J=1.8 Hz, 2H), 6.58 (s, 2H), 6.73 (d, J=1.8 Hz, 2H), 6.99 (d, J=8.6 Hz, 4H), 7.30 (t, J=7.6 Hz, 2H), 7.40 (dd, J=7.2, 7.6 Hz, 4H), 7.62 (d, J=7.2 Hz, 4H), 7.78 (d, J=8.6 Hz, 4H); $^{13}$C NMR (CDCl$_3$) δ 56.4, 67.6, 69.8, 70.7, 94.3, 95.9, 98.7, 107.5, 110.1, 114.9, 123.9, 126.6, 127.6, 128.5, 136.4, 159.4, 159.5, 160.7, 161.1, 161.3, 177.4; LRMS (ESI) m/z 879 (M$^+$+H, 7); HRMS (ESI) Calcd for C$_{52}$H$_{47}$O$_{13}$ (M$^+$+H) 879.3017, found 879.3032.

1,10-Bis[4'-((5-benzyloxy-7-methoxymethoxy)-4H-chromen-4-on-2-yl)phenyl]-1,4,7,10-tetraoxadecane (21c) and 9-[4'-((5-benzyloxy-7-methoxymethoxy)-4H-chromen-4-on-2-yl)phenyl]-3,6,9,-trioxanonan-1-ol (23a): These compounds were prepared from 12a (200 mg, 0.50 mmol), triethylene glycol ditosylate (140 mg, 0.33 mmol), K$_2$CO$_3$ (380 mg) and DMF (8 mL) as the general procedure for the synthesis of flavonoid dimers described above. After crystallization from EtOAc, compound 21c (96 mg, 42%) was obtained as white solid: m.p.: 78-80° C.; $^1$H NMR (CDCl$_3$) δ 3.48 (s, 6H), 3.77 (s, 4), 3.89 (t, J=4.8 Hz, 4H), 4.17 (t, J=4.8 Hz, 4H), 5.20 (s, 8H), 6.46 (d, J=1.6 Hz, 2H), 6.56 (s, 2H), 6.72 (d, J=1.6 Hz, 2H), 6.97 (d, J=8.6 Hz, 4H), 7.30 (t, J=7.2 Hz, 2H), 7.39 (t, J=7.2 Hz, 4H), 7.62 (d, J=7.2 Hz, 4H), 7.76 (d, J=8.6 Hz, 4H); $^{13}$C NMR (CDCl$_3$) δ 56.4, 67.5, 69.6, 70.6, 70.9, 94.3, 95.9, 98.7, 107.4, 110.1, 114.9, 123.8, 126.6, 127.5, 128.5, 136.4, 159.4, 159.5, 160.7, 161.2, 161.2, 177.3; LRMS (ESI) m/z 923 (M$^+$+H, 18), 946 (M$^+$+Na, 50); HRMS (ESI) Calcd for C$_{54}$H$_{50}$O$_{14}$Na (M$^+$+Na) 945.3098, found 945.3103. Then the mother liquid was further evaporated and subjected to flash column chromatography with gradient elution (20% to 50% acetone in CH$_2$Cl$_2$) on silica gel (20 g) to furnish compound 23a (56 mg, 21%) as pale yellow oil: $^1$H NMR (CDCl$_3$) δ 2.64 (br, 1H), 3.47 (s, 3H), 3.60 (t, J=4.2 Hz, 2H), 3.67-3.73 (m, 6H), 3.86 (t, J=4.7 Hz, 2H), 4.16 (t, J=4.7

Hz, 2H), 5.20 (s, 2H), 5.22 (s, 2H), 6.48 (d, J=2.0 Hz, 1H), 6.57 (s, 1H), 6.73 (d, J=2.0 Hz, 1H), 6.97 (d, J=8.8 Hz, 2H), 7.28 (t, J=7.4 Hz, 1H), 7.37 (dd, J=7.4, 7.8 Hz, 2H), 7.61 (d, J=7.8 Hz, 2H), 7.77 (d, J=8.8 Hz, 2H); $^{13}$C NMR (CDCl$_3$) δ 56.3, 61.6, 67.4, 69.4, 70.2, 70.6, 70.7, 72.4, 94.2, 95.9, 98.6, 107.4, 110.0, 114.8, 123.8, 126.5, 127.5, 127.5, 128.4, 136.3, 159.3, 159.5, 160.7, 161.1, 161.2, 177.3.

1,13-Bis[4'-((5-benzyloxy-7-methoxymethoxy)-4H-chromen-4-on-2-yl)phenyl]-1,4,7,10,13-pentaoxamidecane (21d) and 12-[4'-((5-benzyloxy-7-methoxymethoxy)-4H-chromen-4-on-2-yl)phenyl]-3,6,9,12-tetraoxadodecan-1-ol (23b): These compounds was prepared from 12a (1.33 g, 3.3 mmol), tetraethylene glycol dimesylate (0.72 g, 2.1 mmol), K$_2$CO$_3$ (2.27 g) and DMF (30 mL) as the general procedure for the synthesis of flavonoid dimers described above. After flash column chromatography (2% MeOH in CH$_2$Cl$_2$) on silica gel (40 g), the titled compound 21d (0.93 g, 58%) was obtained as white foam: $^1$H NMR (CDCl$_3$) δ 3.44 (s, 6H), 3.67 (t, J=1.6 Hz, 4H), 3.69 (t, J=1.6 Hz, 4H), 3.83 (t, J=4.4 Hz, 4H), 4.09 (t, J=4.0 Hz, 4H), 5.15 (s, 8H), 6.42 (d, J=1.8 Hz, 2H), 6.49 (s, 2H), 6.67 (d, J=1.8 Hz, 2H), 6.92 (d, J=8.8 Hz, 4H), 7.25 (t, J=7.2 Hz, 2H), 7.36 (dd, J=7.2, 7.6 Hz, 4H), 7.60 (d, J=7.6 Hz, 4H), 7.71 (d, J=8.8 Hz, 4H); $^{13}$C NMR (CDCl$_3$) δ 56.4, 67.5, 69.5, 70.6, 70.6, 70.8, 94.3, 95.9, 98.6, 107.4, 110.0, 114.8, 123.7, 126.6, 127.5, 127.5, 128.5, 136.5, 159.3, 159.5, 160.6, 161.2, 177.2; LRMS (ESI) m/z 967 (M$^+$+H, 18), 989 (M$^+$+H, 100); HRMS (ESI) Calcd for C$_{56}$H$_{55}$O$_{15}$ (M$^+$+H) 967.3541, found 967.3568. The titled compound 23b (0.27 g, 14%) was obtained as pale yellow oil: $^1$H NMR (CDCl$_3$) δ 3.00 (br, 1H), 3.44 (s, 3H), 3.56 (t, J=4.2 Hz, 2H), 3.62-3.69 (m, 10H), 3.82 (t, J=4.5 Hz, 2H), 4.13 (t, J=4.5 Hz, 2H), 5.17 (s, 2H), 5.18 (s, 2H), 6.44 (d, J=1.8 Hz, 1H), 6.53 (s, 1H), 6.70 (d, J=1.8 Hz, 1H), 6.94 (d, J=8.8 Hz, 2H), 7.25 (t, J=7.4 Hz, 1H), 7.35 (dd, J=7.4, 7.6 Hz, 2H), 7.59 (d, J=7.6 Hz, 2H), 7.74 (d, J=8.8 Hz, 2H); $^{13}$C NMR (CDCl$_3$) δ 56.2, 61.4, 67.3, 69.3, 70.0, 70.3, 70.4, 70.4, 70.6, 72.4, 94.1, 95.8, 98.5, 107.2, 109.9, 114.7, 123.6, 126.4, 127.4, 128.3, 136.2, 159.2, 159.3, 160.6, 161.0, 161.1, 177.2.

1,16-Bis[4'-((5-benzyloxy-7-methoxymethoxy)-4H-chromen-4-on-2-yl)phenyl]-1,4,7,10,13,16-hexaoxahexadecane (21e): This compound was prepared from 12a (300 mg, 0.74 mmol), pentaethylene glycol dimesylate (170 mg, 0.43 mmol), K$_2$CO$_3$ (480 mg) and DMF (10 mL) as the general procedure for the synthesis of flavonoid dimers described above. After flash column chromatography (2% MeOH in CH$_2$Cl$_2$) on silica gel (15 g), the titled compound (160 mg, 43%) was obtained as white foam: $^1$H NMR (CDCl$_3$) δ 3.44 (s, 6H), 3.63-3.68 (m, 12H), 3.81 (t, J=4.2 Hz, 4H), 4.09 (t, J=4.2 Hz, 4H), 5.15 (s, 8H), 6.42 (d, J=1.6 Hz, 2H), 6.49 (s, 2H), 6.67 (d, J=1.6 Hz, 2H), 6.93 (d, J=8.6 Hz, 4H), 7.26 (t, J=6.8 Hz, 2H), 7.36 (dd, J=6.8, 7.4 Hz, 4H), 7.59 (d, J=7.4 Hz, 4H), 7.71 (d, J=8.6 Hz, 4H); $^{13}$C NMR (CDCl$_3$) δ 56.4, 67.5, 69.5, 70.5, 70.8, 94.3, 95.9, 98.6, 107.4, 110.0, 114.8, 123.7, 126.6, 127.5, 127.5, 128.5, 128.6, 136.4, 159.3, 159.5, 160.6, 161.2, 177.3; LRMS (ESI) m/z 1011 (M$^+$+H, 4), 1033 (M$^+$+Na, 26); HRMS (ESI) Calcd for C$_{58}$H$_{59}$O$_{16}$ (M$^+$+H) 1011.3803, found 1011.3793.

1,19-Bis[4'-((5-benzyloxy-7-methoxymethoxy)-4H-chromen-4-on-2-yl)phenyl]-1,4,7,10,13,16,19-heptaoxanonadecane (21f): This compound was prepared from 12a (230 mg, 0.57 mmol), hexaethylene glycol dimesylate (160 mg, 0.37 mmol), K$_2$CO$_3$ (400 mg) and DMF (10 mL) as the general procedure for the synthesis of flavonoid dimers described above. After flash column chromatography (2% MeOH in CH$_2$Cl$_2$) on silica gel (15 g), the titled compound (160 mg, 53%) was obtained as white foam: $^1$H NMR (CDCl$_3$) δ 3.47 (s, 6H), 3.64-3.71 (m, 16H), 3.85 (t, J=4.4 Hz, 4H), 4.15 (t, J=4.4 Hz, 4H), 5.19 (s, 4H), 5.21 (s, 4H), 6.47 (d, J=2.0 Hz, 2H), 6.54 (s, 2H), 6.72 (d, J=2.0 Hz, 2H), 6.97 (d, J=8.8 Hz, 4H), 7.27 (t, J=7.2 Hz, 2H), 7.38 (dd, J=7.2, 7.6 Hz, 4H), 7.61 (d, J=7.6 Hz, 4H), 7.76 (d, J=8.8 Hz, 4H); $^{13}$C NMR (CDCl$_3$) δ 56.4, 67.5, 69.5, 70.5, 70.6, 70.6, 70.8, 94.3, 95.9, 98.7, 107.5, 110.1, 114.9, 123.8, 126.6, 127.5, 128.5, 136.4, 159.4, 159.5, 160.6, 161.2, 177.3; LRMS (ESI) m/z 1055 (M$^+$+H, 11), 1077 (M$^+$+Na, 47); HRMS (ESI) Calcd for C$_{60}$H$_{62}$O$_{17}$Na (M$^+$+Na) 1077.3885, found 1077.3883.

1,22-Bis[4'-((5-benzyloxy-7-methoxymethoxy)-4H-chromen-4-on-2-yl)phenyl]-1,4,7,10,13,16,19,22-octaoxadocosane (21g): This compound was prepared from 12a (220 mg, 0.54 mmol), heptaethylene glycol dimesylate (160 mg, 0.33 mmol), K$_2$CO$_3$ (370 mg) and DMF (10 mL) as the general procedure for the synthesis of flavonoid dimers described above. After flash column chromatography (4% MeOH in CH$_2$Cl$_2$) on silica gel (15 g), the titled compound (160 mg, 54%) was obtained as white foam: $^1$H NMR (CDCl$_3$) δ 3.44 (s, 6H), 3.61-3.69 (m, 20H), 3.82 (t, J=4.2 Hz, 4H), 4.12 (t, J=4.2 Hz, 4H), 5.17 (s, 4H), 5.18 (s, 4H), 6.44 (d, J=1.6 Hz, 2H), 6.51 (s, 2H), 6.69 (d, J=1.6 Hz, 2H), 6.94 (d, J=8.6 Hz, 4H), 7.25 (t, J=6.8 Hz, 2H), 7.36 (dd, J=6.8, 7.0 Hz, 4H), 7.60 (d, J=7.0 Hz, 4H), 7.34 (d, J=8.6 Hz, 4H); $^{13}$C NMR (CDCl$_3$) δ 56.4, 67.5, 69.5, 70.5, 70.5, 70.8, 94.3, 95.9, 98.6, 107.4, 110.1, 114.8, 123.7, 126.6, 127.5, 128.5, 128.7, 136.4, 159.3, 159.5, 160.6, 161.2, 177.3; LRMS (ESI) m/z 1099 (M$^+$+H, 7), 1121 (M$^+$+Na, 31); HRMS (ESI) Calcd for C$_{62}$H$_{66}$O$_{18}$Na (M+Na) 1121.4147, found 1121.4132.

1,25-Bis[4'-((5-benzyloxy-7-methoxymethoxy)-4H-chromen-4-on-2-yl)phenyl]-1,4,7,10,13,16,19,22,25-nonaoxapentacosane (21h): This compound was prepared from 12a (250 mg, 0.62 mmol), octaethylene glycol dimesylate (200 mg, 0.38 mmol), K$_2$CO$_3$ (420 mg) and DMF (10 mL) as the general procedure for the synthesis of flavonoid dimers described above. After flash column chromatography (4% MeOH in CH$_2$Cl$_2$) on silica gel (15 g), the titled compound (170 mg, 48%) was obtained as white foam: $^1$H NMR (CDCl$_3$) δ 3.43 (s, 6H), 3.59-3.67 (m, 24 H), 3.80 (t, J=4.8 Hz, 4H), 4.10 (t, J=4.8 Hz, 4H), 5.15 (s, 4H), 5.16 (s, 4H), 6.43 (d, J=2.0 Hz, 2H), 6.50 (s, 2H), 6.68 (d, J=2.0 Hz, 2H), 6.92 (d, J=9.2 Hz, 4H), 7.25 (t, J=7.6 Hz, 2H), 7.34 (dd, J=7.6, 7.2 Hz, 4H), 7.59 (d, J=7.2 Hz, 4H), 7.72 (d, J=9.2 Hz, 4H); $^{13}$C NMR (CDCl$_3$) δ 56.4, 67.5, 69.4, 70.5, 70.5, 70.8, 94.3, 95.9, 98.6, 107.4, 110.1, 114.8, 123.7, 126.5, 127.5, 128.5, 136.4, 159.3, 159.5, 160.6, 161.2, 161.2, 177.2; LRMS (ESI) m/z 1144 (M$^+$+H, 3), 1166 (M$^+$+Na, 21); HRMS (ESI) Calcd for C$_{64}$H$_{70}$O$_{19}$Na (M$^+$+Na) 1165.4409, found 1165.4424.

1,28-Bis[4'-((5-benzyloxy-7-methoxymethoxy)-4H-chromen-4-on-2-yl)phenyl]-1,4,7,10,13,16,19,22,25,28-decaoxaoctacosane (21i): This compound was prepared from 12a (240 mg, 0.59 mmol), nonaethylene glycol dimesylate (210 mg, 0.37 mmol), K$_2$CO$_3$ (410 mg) and DMF (10 mL) as the general procedure for the synthesis of flavonoid dimers described above. After flash column chromatography (4% MeOH in CH$_2$Cl$_2$) on silica gel (15 g), the titled compound (180 mg, 51%) was obtained as white foam: $^1$H NMR (CDCl$_3$) δ 3.42 (s, 6H), 3.58-3.66 (m, 28H), 3.80 (t, J=4.6 Hz, 4H), 4.10 (t, J=4.6 Hz, 4H), 5.14 (s, 4H), 5.15 (s, 4H), 6.42 (d, J=2.0 Hz, 2H), 6.48 (s, 2H), 6.67 (d, J=2.0 Hz, 2H), 6.91 (d, J=8.8 Hz, 4H), 7.23 (t, J=7.6 Hz, 2H), 7.33 (t, J=7.6 Hz, 4H), 7.59 (d, J=7.6 Hz, 4H), 7.71 (d, J=8.8 Hz, 4H); $^{13}$C NMR (CDCl$_3$) δ 56.3, 67.5, 69.4, 70.5, 70.5, 70.8, 94.2, 95.9, 98.6, 107.4, 110.1, 114.8, 123.7, 126.5, 127.5, 128.5, 136.4, 159.3, 159.5, 160.6, 161.2, 161.2, 177.2; LRMS (ESI) m/z 1188 (M$^+$+H, 3), 1210 (M$^+$+Na, 23); HRMS (ESI) Calcd for C$_{66}$H$_{75}$O$_{20}$ (M$^+$+H) 1187.4852, found 1187.4825.

General procedure for the hydrogenolysis of compounds 21a-i and 23a-b: To a round-bottom flask was charged with compound 21 or 23, catalytic amount of 10% Pd on activated charcoal and chloroform. The reaction mixture was stirred vigorously under hydrogen atmosphere at balloon pressure and room temperature for 12 h. When TLC indicated complete consumption of the starting material, the charcoal was removed by suction filtration. The pale yellow filtrate was purified by passing through a short pad of silica gel to furnish the deprotected products.

1,4-Bis[4'-((5-hydroxy-7-methoxymethoxy)-4H-chromen-4-on-2-yl)phenyl]-1,4-dioxabutane (22a): This compound was prepared from 21a (64 mg, 0.08 mmol), 10% Pd on charcoal (15 mg) and chloroform (10 mL) as the general procedure for the hydrogenolysis described above. The titled compound (43 mg, 86%) was obtained as white solid: m.p.: 206-207° C.; $^1$H NMR (CDCl$_3$) δ 3.51 (s, 6H), 4.44 (s, 4H), 5.24 (s, 4H), 6.47 (d, J=2.0 Hz, 2H), 6.59 (s, 2H), 6.66 (d, J=2.0 Hz, 2H), 7.07 (d, J=8.8 Hz, 4H), 7.86 (d, J=8.8 Hz, 4H), 12.73 (s, 2H); $^{13}$C NMR (CDCl$_3$) δ 56.4, 66.5, 94.2, 94.3, 100.1, 104.5, 106.2, 115.1, 124.0, 128.1, 157.5, 161.5, 162.0, 162.9, 163.9, 182.5; LRMS (ESI) m/z 655 (M$^+$+H, 14), 677 (M++Na, 8); HRMS (ESI) Calcd for C$_{36}$H$_{31}$O$_{12}$ (M$^+$+H) 655.1816, found 655.1845.

1,7-Bis[4'-((5-hydroxy-7-methoxymethoxy)-4H-chromen-4-on-2-yl)phenyl]-1,4,7-trioxaheptane (22b): This compound was prepared from 21b (88 mg, 0.10 mmol), 10% Pd on charcoal (18 mg) and chloroform (10 mL) as the general procedure for the hydrogenolysis described above. The titled compound (60 mg, 86%) was obtained as white solid: m.p.: 171-172° C.; $^1$H NMR (CDCl$_3$) δ 3.50 (s, 6H), 3.98 (t, J=4.4 Hz, 4H), 4.24 (t, J=4.4 Hz, 4H), 5.23 (s, 4H), 6.44 (d, J=1.6 Hz, 2H), 6.55 (s, 2H), 6.62 (d, J=1.6 Hz, 2H), 7.00 (d, J=9.0 Hz, 4H), 7.79 (d, J=9.0 Hz, 4H), 12.63 (s, 2H); $^{13}$C NMR (d$_6$-DMSO) δ 56.5, 68.0, 69.3, 94.3, 94.9, 99.8, 104.1, 105.6, 115.5, 123.0, 128.8, 157.4, 161.5, 162.1, 162.9, 164.1, 182.4; LRMS (ESI) m/z 699 (M$^+$+H, 5), 721 (M++Na, 3); HRMS (ESI) Calcd for C$_{38}$H$_{35}$O$_{13}$ (M$^+$+H) 699.2078, found 699.2079.

1,10-Bis[4'-((5-hydroxy-7-methoxymethoxy)-4H-chromen-4-on-2-yl)phenyl]-1,4,7,10-tetraoxadecane (22c): This compound was prepared from 21c (96 mg, 0.10 mmol), 10% Pd on charcoal (15 mg) and chloroform (10 mL) as the general procedure for the hydrogenolysis described above. The titled compound (62 mg, 80%) was obtained as pale yellow solid: m.p.: 159-160° C.; $^1$H NMR (CDCl$_3$) δ 3.39 (s, 6H), 3.62 (d, J=4.0 Hz, 4H), 3.76 (t, J=4.6 Hz, 4H), 4.17 (t, J=4.6 Hz, 4H), 5.28 (s, 4H), 6.37 (d, J=2.0 Hz, 2H), 6.76 (d, J=2.0 Hz, 2H), 6.87 (s, 2H), 7.06 (d, J=8.8 Hz, 4H), 7.96 (d, J=8.8 Hz, 4H), 12.85 (s, 2H); $^{13}$C NMR (d$_6$-DMSO) δ 56.3, 67.8, 69.0, 70.3, 94.2, 94.7, 99.6, 103.9, 105.4, 115.2, 122.8, 128.6, 157.2, 161.4, 161.9, 162.7, 163.8, 182.2; LRMS (ESI) m/z 743 (M$^+$+H, 9); HRMS (ESI) Calcd for C$_{40}$H$_{39}$O$_{14}$ (M$^+$+H) 743.2340, found 743.2343.

1,13-Bis[4'-((5-hydroxy-7-methoxymethoxy)-4H-chromen-4-on-2-yl)phenyl]-1,4,7,10,13-pentaoxamidecane (22d): This compound was prepared from 21d (930 mg, 0.96 mmol), 10% Pd on charcoal (88 mg) and chloroform (20 mL) as the general procedure for the hydrogenolysis described above. The titled compound (710 mg, 94%) was obtained as white foam: $^1$H NMR (CDCl$_3$) δ 3.39 (s, 6H), 3.55-3.59 (m, 8H), 3.76 (t, J=4.6 Hz, 4H), 4.13 (d, J=4.6 Hz, 4H), 5.28 (s, 4H), 6.37 (d, J=2.0 Hz, 2H), 6.75 (d, J=2.0 Hz, 2H), 6.85 (s, 2H), 7.04 (d, J=8.8 Hz, 4H), 7.95 (d, J=8.8 Hz, 4H), 12.84 (s, 2H); $^{13}$C NMR (d$_6$-DMSO) δ 56.3, 56.3, 67.8, 69.0, 70.2, 94.2, 94.7, 99.6, 103.9, 105.4, 115.2, 122.8, 128.6, 157.1, 161.4, 161.9, 162.7, 163.8, 182.2; LRMS (ESI) m/z 787 (M$^+$+H, 57), 809 (M$^+$+Na, 60); HRMS (ESI) Calcd for C$_{42}$H$_{43}$O$_{15}$ (M$^+$+H) 787.2602, found 787.2591.

1,16-Bis[4'-((5-hydroxy-7-methoxymethoxy)-4H-chromen-4-on-2-yl)phenyl]-1,4,7,10,13,16-hexaoxahexadecane (22e): This compound was prepared from 21e (75 mg, 0.07 mmol), 10% Pd on charcoal (12 mg) and chloroform (10 mL) as the general procedure for the hydrogenolysis described above. The titled compound (52 mg, 84%) was obtained as white foam: $^1$H NMR (CDCl$_3$) δ 3.48 (s, 6H), 3.66-3.73 (m, 12H), 3.87 (t, J=4.6 Hz, 4H), 4.17 (t, J=4.6 Hz, 4H), 5.22 (s, 4H), 6.42 (d, J=2.0 Hz, 2H), 6.52 (s, 2H), 6.61 (d, J=2.0 Hz, 2H), 6.97 (d, J=9.0 Hz, 4H), 7.77 (d, J=9.0 Hz, 4H), 12.72 (s, 2H); $^{13}$C NMR (CDCl$_3$) δ 56.4, 67.0, 67.6, 69.5, 70.6, 70.8, 94.1, 94.2, 100.0, 104.2, 106.1, 115.0, 123.4, 127.9, 157.4, 161.7, 161.9, 162.8, 163.9, 182.4; LRMS (ESI) m/z 831 (M$^+$+H, 35), 853 (M$^+$+Na, 100); HRMS (ESI) Calcd for C$_{44}$H$_{46}$O$_{16}$Na (M$^+$+Na) 853.2684, found 853.2677.

1,19-Bis[4'-((5-hydroxy-7-methoxymethoxy)-4H-chromen-4-on-2-yl)phenyl]-1,4,7,10,13,16,19-heptaoxanonadecane (22f): This compound was prepared from 21f (76 mg, 0.07 mmol), 10% Pd on charcoal (19 mg) and chloroform (10 mL) as the general procedure for the hydrogenolysis described above. The titled compound (52 mg, 83%) was obtained as white foam: $^1$H NMR (CDCl$_3$) δ 3.47 (s, 6H), 3.64-3.72 (m, 16H), 3.85 (t, J=4.6 Hz, 4H), 4.15 (t, J=4.6 Hz, 4H), 5.20 (s, 4H), 6.40 (d, J=2.0 Hz, 2H), 6.49 (s, 2H), 6.58 (d, J=2.0 Hz, 2H), 6.95 (d, J=8.8 Hz, 4H), 7.74 (d, J=8.8 Hz, 4H), 12.70 (s, 2H); $^{13}$C NMR (CDCl$_3$) δ 56.3, 66.9, 67.5, 69.4, 70.4, 70.5, 70.7, 94.1, 94.1, 99.9, 104.1, 106.0, 114.9, 123.3, 127.8, 157.3, 161.7, 161.8, 162.7, 163.8, 182.3; LRMS (ESI) m/z 875 (M$^+$+H, 28), 897 (M$^+$+Na, 100); HRMS (ESI) Calcd for C$_{46}$H$_{50}$O$_{17}$Na (M$^+$+Na) 897.2946, found 897.2936.

1,22-Bis[4'-((5-hydroxy-7-methoxymethoxy)-4H-chromen-4-on-2-yl)phenyl]-1,4,7,10,13,16,19,22-octaoxadocosane (22g): This compound was prepared from 21g (102 mg, 0.09 mmol), 10% Pd on charcoal (21 mg) and chloroform (10 mL) as the general procedure for the hydrogenolysis described above. The titled compound (78 mg, 91%) was obtained as white foam: $^1$H NMR (CDCl$_3$) δ 3.45 (s, 6H), 3.61-3.70 (m, 20H), 3.84 (t, J=4.6 Hz, 4H), 4.12 (t, J=4.6 Hz, 4H), 5.18 (s, 4H), 6.38 (d, J=2.0 Hz, 2H), 6.47 (s, 2H), 6.56 (d, J=2.0 Hz, 2H), 6.93 (d, J=9.0 Hz, 4H), 7.72 (d, J=9.0 Hz, 4H), 12.70 (s, 2H); $^{13}$C NMR (CDCl$_3$) δ 56.3, 67.6, 69.4, 70.5, 70.5, 70.8, 94.1, 94.2, 99.9, 104.1, 106.0, 114.9, 123.3, 127.9, 157.4, 161.8, 161.8, 162.8, 163.9, 182.3; LRMS (ESI) m/z 919 (M$^+$+H, 5), 941 (M$^+$+Na, 100); HRMS (ESI) Calcd for C$_{48}$H$_{54}$O$_{18}$Na (M$^+$+Na) 941.3208, found 941.3188.

1,25-Bis[4'-((5-hydroxy-7-methoxymethoxy)-4H-chromen-4-on-2-yl)phenyl]-1,4,7,10,13,16,19,22,25-nonaoxapentacosane (22h): This compound was prepared from 21h (89 mg, 0.08 mmol), 10% Pd on charcoal (16 mg) and chloroform (10 mL) as the general procedure for the hydrogenolysis described above. The titled compound (62 mg, 83%) was obtained as white foam: $^1$H NMR (CDCl$_3$) δ 3.50 (s, 6H), 3.68-3.75 (m, 24H), 3.87 (t, J=4.6 Hz, 4H), 4.18 (t, J=4.6 Hz, 4H), 5.23 (s, 4H), 6.44 (d, J=2.0 Hz, 2H), 6.54 (s, 2H), 6.62 (d, J=2.0 Hz, 2H), 6.98 (d, J=8.8 Hz, 4H), 7.78 (d, J=8.8 Hz, 4H), 12.72 (s, 2H); $^{13}$C NMR (CDCl$_3$) δ 56.4, 56.4, 67.6, 69.5, 70.2, 70.3, 70.4, 70.7, 94.2, 94.3, 100.0, 104.3, 106.1, 115.0, 123.5, 128.0, 157.4, 161.7, 161.9, 162.9, 163.9, 182.4; LRMS (ESI) m/z 963 (M$^+$+H, 50), 985 (M$^+$+Na, 100); HRMS (ESI) Calcd for C$_{50}$H$_{59}$O$_{19}$ (M$^+$+H) 963.3651, found 963.3637.

1,28-Bis[4'-((5-hydroxy-7-methoxymethoxy)-4H-chromen-4-on-2-yl)phenyl]-1,4,7,10,13,16,19,22,25,28-decaoxaoctacosane (22i): This compound was prepared from flavone 21i (120 mg, 0.10 mmol), 10% Pd on charcoal (28 mg) and chloroform (10 mL) as the general procedure for the hydrogenation of bis-flavones described above. The titled compound (92 mg, 90%) was obtained as white foam: $^1$H NMR (CDCl$_3$) δ 3.39 (s, 6H), 3.53-3.63 (m, 28H), 3.77 (t, J=4.6 Hz, 4H), 4.04 (t, J=4.6 Hz, 4H), 5.11 (s, 4H), 6.28 (d, J=1.8 Hz, 2H), 6.37 (s, 2H), 6.47 (d, J=1.8 Hz, 2H), 6.84 (d, J=8.8 Hz, 4H), 7.62 (d, J=8.8 Hz, 4H), 12.63 (s, 2H); $^{13}$C NMR (CDCl$_3$) δ 56.0, 57.2, 69.1, 70.1, 70.2, 70.4, 93.8, 93.8, 99.5, 103.6, 105.6, 114.6, 122.8, 127.5, 156.9, 161.4, 161.5, 162.4, 163.5, 181.9; LRMS (ESI) m/z 1007 (M$^+$+H, 10), 1029 (M$^+$+Na, 58); HRMS (ESI) Calcd for C$_{52}$H$_{62}$O$_{20}$Na (M$^+$+Na) 1029.3732, found 1029.3696.

9-[4'-((5-hydroxy-7-methoxymethoxy)-4H-chromen-4-on-2-yl)phenyl]-3,6,9,-trioxanonan-1-ol (24a): This compound was prepared from 23a (48 mg, 0.09 mmol), 10% Pd on charcoal (8 mg) and chloroform (10 mL) as the general procedure for the hydrogenolysis described above. The titled compound (32 mg, 80%) was obtained as pale yellow solid: m.p.: 57-59° C.; $^1$H NMR (CDCl$_3$) δ 3.49 (s, 3H), 3.62 (t, J=4.2 Hz, 2H), 3.70-3.75 (m, 6H), 3.89 (t, J=4.7 Hz, 2H), 4.20 (t, J=4.7 Hz, 2H), 5.23 (s, 2H), 6.45 (d, J=2.0 Hz, 1H), 6.56 (s, 1H), 6.64 (d, J=2.0 Hz, 1H), 7.00 (d, J=8.8 Hz, 2H), 7.81 (d, J=8.8 Hz, 2H); $^{13}$C NMR (CDCl$_3$) δ 56.2, 61.5, 67.4, 69.3, 70.1, 70.7, 72.3, 94.0, 94.1, 99.9, 104.1, 106.0, 114.8, 123.4, 127.8, 157.3, 161.6, 161.8, 162.3, 163.9, 182.3; LRMS (EI) m/z 446 (M$^+$, 100); HRMS (EI) Calcd for C$_{23}$H$_{26}$O$_9$ (M$^+$) 446.1577, found 446.1570.

12-[4'-((5-hydroxy-7-methoxymethoxy)-4H-chromen-4-on-2-yl)phenyl]-3,6,9,12-tetraoxadodecan-1-ol (24b): This compound was prepared from 23b (150 mg, 0.26 mmol), 10% Pd on charcoal (22 mg) and chloroform (20 mL) as the general procedure for the hydrogenolysis described above. The titled compound (122 mg, 96%) was obtained as pale yellow oil: $^1$H NMR (CDCl$_3$) δ 3.44 (s, 3H), 3.56 (t, J=4.2 Hz, 2H), 3.62-3.69 (m, 10H), 3.82 (t, J=4.5 Hz, 2H), 4.13 (t, J=4.5 Hz, 2H), 5.18 (s, 2H), 6.44 (d, J=1.8 Hz, 1H), 6.53 (s, 1H), 6.70 (d, J=1.8 Hz, 1H), 6.94 (d, J=8.8 Hz, 2H), 7.74 (d, J=8.8 Hz, 2H); $^{13}$C NMR (CDCl$_3$) δ 56.2, 61.4, 67.3, 69.3, 70.0, 70.3, 70.4, 70.4, 70.6, 72.4, 94.1, 95.8, 98.5, 107.2, 109.9, 114.7, 123.6, 126.4, 127.4, 128.3, 136.2, 159.2, 159.3, 160.6, 161.0, 161.1, 177.2; LRMS (EI) m/z 490 (M$^+$, 100); HRMS (EI) Calcd for C$_{25}$H$_{30}$O$_{10}$ (M$^+$) 490.1839, found 490.1828.

General procedure for the deprotection of MOM group of 22a-i: Method A: To a round-bottom flask was charged with compound 22 and 75% AcOH. The reaction mixture was stirred at refluxing temperature for 14 h. When TLC indicated complete consumption of 22, the reaction mixture was cooled to 0° C. and ice water was added. The off-white solid that was formed was collected by suction filtration. Method B: To a round-bottom flask was charged with compound 22, 6M HCl solution and THF. The reaction mixture was stirred at room temperature for 15 minutes. When TLC indicated complete consumption of 22, the reaction mixture was poured into a separating funnel containing water. The mixture was extracted with EtOAc (20 mL×3). The combined organic layers were dried over MgSO$_4$, filtered and evaporated to give a crude mixture. Purification of the crude mixture by passing through a short pad of silica gel furnished the desired product.

1,4-Bis[4'-((5,7-dihydroxy)-4H-chromen-4-on-2-yl)phenyl]-1,4-dioxabutane (9a): This compound was prepared from compound 22a (43 mg, 0.07 mmol) and 75% acetic acid (20 mL) as Method A described above. The titled compound (26 mg, 70%) was obtained as pale green solid: m.p.: 352-355° C.; $^1$H NMR (d$_6$-DMSO) δ 4.46 (s, 4H), 6.19 (d, J=1.6 Hz, 2H), 6.50 (d, J=1.6 Hz, 2H), 6.88 (d, J=8.4 Hz, 4H), 8.04 (d, J=8.4 Hz, 4H), 10.85 (s, 2H), 12.90 (s, 2H); $^{13}$C NMR (CDCl$_3$) δ 67.0, 94.5, 99.3, 104.1, 104.2, 115.5, 123.4, 128.8, 157.8, 161.7, 161.9, 163.6, 164.7, 182.2; LRMS (EI) m/z 566 (M$^+$, 11); HRMS (ESI) Calcd for C$_{32}$H$_{23}$O$_{10}$ (M$^+$+H) 567.1291, found 567.1268.

1,7-Bis[4'-((5,7-dihydroxy)-4H-chromen-4-on-2-yl)phenyl]-1,4,7-trioxaheptane (9b): This compound was prepared from compound 22b (57 mg, 0.08 mmol) and 75% acetic acid (25 mL) as Method A described above. The titled compound (42 mg, 84%) was obtained as off-white solid: m.p.: 268-270° C.; $^1$H NMR (d$_6$-DMSO) δ 3.85 (s, 4H), 4.22 (s, 4H), 6.16 (d, J=1.8 Hz, 2H), 6.46 (d, J=1.8 Hz, 2H), 6.84 (s, 2H), 7.09 (d, J=8.8 Hz, 4H), 7.98 (d, J=8.8 Hz, 4H), 10.82 (s, 2H), 12.98 (s, 2H); $^{13}$C NMR (d$_6$-DMSO) δ 68.0, 69.3, 94.4, 99.3, 103.9, 104.2, 115.4, 123.3, 128.7, 157.7, 161.9, 161.9, 163.6, 164.6, 182.2; LRMS m/z 611 (M$^+$+H, 8), 633 (M$^+$+Na, 3); HRMS Calcd for C$_{34}$H$_{27}$O$_{11}$ (M$^+$+H) 611.1553, found 611.1542.

1,10-Bis[4'-((5,7-dihydroxy)-4H-chromen-4-on-2-yl)phenyl]-1,4,7,10-tetraoxadecane (9c): This compound was prepared from compound 22c (62 mg, 0.08 mmol) and 75% acetic acid (25 mL) as Method A described above. The titled compound (43 mg, 79%) was obtained as pale yellow solid: m.p.: 143-145° C.; $^1$H NMR (d$_6$-DMSO) δ 3.81 (s, 4H), 3.95 (s, 4H), 4.36 (s, 4H), 6.35 (d, J=1.0 Hz, 2H), 6.64 (d, J=1.0 Hz, 2H), 7.01 (s, 2H), 7.27 (d, J=8.8 Hz, 4H), 8.16 (d, J=8.8 Hz, 4H), 11.00 (s, 2H), 13.08 (s, 2H); $^{13}$C NMR (d$_6$-DMSO) δ 67.8, 69.0, 70.2, 94.2, 99.1, 103.7, 104.0, 115.2, 123.0, 128.5, 157.5, 161.7, 161.8, 163.4, 164.4, 182.0; LRMS (ESI) m/z 655 (M$^+$+H, 15); HRMS (ESI) Calcd for C$_{36}$H$_{31}$O$_{12}$ (M$^+$+H) 655.1816, found 655.1816.

1,13-Bis[4'-((5,7-dihydroxy)-4H-chromen-4-on-2-yl)phenyl]-1,4,7,10,13-pentaoxamidecane (9d): This compound was prepared from compound 22d (720 mg, 0.92 mmol), 6M HCl solution (70 mL) and THF (50 mL) as Method B described above. The titled compound (620 mg, 97%) was obtained as pale yellow solid: m.p.: 131-133° C.; $^1$H NMR (d$_6$-DMSO) δ 3.54-3.58 (m, 8H), 3.75 (t, J=4.4 Hz, 4H), 4.15 (t, J=4.4 Hz, 4H), 6.16 (d, J=2.0 Hz, 2H), 6.45 (d, J=2.0 Hz, 2H), 6.81 (s, 2H), 7.07 (d, J=8.8 Hz, 4H), 7.96 (d, J=8.8 Hz, 4H), 10.81 (s, 2H), 12.88 (s, 2H); $^{13}$C NMR (d$_6$-DMSO) δ 68.0, 69.2, 70.3, 70.4, 94.4, 99.3, 103.9, 104.2, 115.4, 123.2, 128.7, 157.7, 161.8, 161.9, 163.6, 164.6, 182.2; LRMS (ESI) m/z 699 (M$^+$+H, 33), 721 (M$^+$+Na, 58); HRMS (ESI) Calcd for C$_{38}$H$_{35}$O$_{13}$Na (M++Na) 721.1897, found 721.1896.

1,16-Bis[4'-((5,7-dihydroxy)-4H-chromen-4-on-2-yl)phenyl]-1,4,7,10,13,16-hexaoxahexadecane (9e): This compound was prepared from compound 22e (48 mg, 0.06 mmol), 6M HCl solution (20 mL) and THF (20 mL) as Method B described above. The titled compound (37 mg, 86%) was obtained as pale yellow foam; $^1$H NMR (d$_6$-acetone) δ 3.59-3.65 (m, 12H), 3.83 (t, J=4.6 Hz, 4H), 4.20 (t, J=4.6 Hz, 4H), 6.22 (d, J=2.0 Hz, 2H), 6.51 (d, J=2.0 Hz, 2H), 6.63 (s, 2H), 7.09 (d, J=8.8 Hz, 4H), 7.95 (d, J=8.8 Hz, 4H), 12.90 (s, 2H); $^{13}$C NMR (d$_6$-acetone) δ 67.8, 69.2, 70.4, 70.5, 93.8, 98.8, 103.6, 104.4, 115.0, 123.4, 128.1, 157.8, 162.0, 164.0, 164.6, 182.2; LRMS (ESI) m/z 743 (M$^+$+H, 34), 765 (M$^+$+Na, 100); HRMS (ESI) Calcd for C$_{40}$H$_{38}$O$_{14}$Na (M$^+$+Na) 765.2159, found 765.2164.

1,19-Bis[4'-((5,7-dihydroxy)-4H-chromen-4-on-2-yl)phenyl]-1,4,7,10,13,16,19-heptaoxanonadecane (9f): This compound was prepared from compound 22f (45 mg, 0.05 mmol), 6M HCl solution (20 mL) and THF (20 mL) as Method B described above. The titled compound (36 mg, 89%) was obtained as pale yellow foam: $^1$H NMR (d$_6$-acetone) δ 3.56-3.65 (m, 16H), 3.81 (t, J=4.6 Hz, 4H), 4.17 (t, J=4.6 Hz, 4H), 6.22 (d, J=2.0 Hz, 2H), 6.48 (d, J=2.0 Hz, 2H), 6.57 (s, 2H), 7.02 (d, J=8.8 Hz, 4H), 7.88 (d, J=8.8 Hz, 4H), 12.88 (s, 2H); $^{13}$C NMR (d$_6$-acetone) δ 67.7, 69.2, 70.3, 70.3, 70.5, 93.9, 98.8, 103.5, 104.4, 114.9, 123.3, 128.0, 157.6, 162.0, 162.3, 163.6, 163.9, 182.0; LRMS (ESI) m/z 809 (M$^+$+Na, 15); HRMS (ESI) Calcd for $C_{42}H_{43}O_{15}$ (M$^+$+H) 787.2602, found 787.2614.

1,22-Bis[4'-((5,7-dihydroxy)-4H-chromen-4-on-2-yl)phenyl]-1,4,7,10,13,16,19,22-octaoxadocosane (9g): This compound was prepared from compound 22g (65 mg, 0.07 mmol), 6M HCl solution (20 mL) and THF (20 mL) as Method B described above. The titled compound (58 mg, 99%) was obtained as pale yellow foam: $^1$H NMR (d$_6$-acetone) δ 3.54-3.65 (m, 20H), 3.81 (t, J=4.6 Hz, 4H), 4.18 (t, J=4.6 Hz, 4H), 6.23 (d, J=2.0 Hz, 2H), 6.49 (d, J=2.0 Hz, 2H), 6.59 (s, 2H), 7.04 (d, J=9.0 Hz, 4H), 7.90 (d, J=9.0 Hz, 4H), 12.90 (s, 2H); $^{13}$C NMR (d$_6$-acetone) δ 67.7, 69.2, 70.3, 70.3, 70.5, 93.9, 98.8, 103.6, 104.4, 114.9, 123.3, 128.0, 157.8, 162.0, 162.0, 163.6, 163.9, 182.0; LRMS (ESI) m/z 853 (M$^+$+Na, 36); HRMS (ESI) Calcd for $C_{44}H_{47}O_{16}$ (M$^+$+H) 831.2864, found 831.2889.

1,25-Bis[4'-((5,7-dihydroxy)-4H-chromen-4-on-2-yl)phenyl]-1,4,7,10,13,16,19,22,25-nonaoxapentacosane (9h): This compound was prepared from compound 22h (50 mg, 0.05 mmol), 6M HCl solution (20 mL) and THF (20 mL) as Method B described above. The titled compound (42 mg, 92%) was obtained as pale yellow foam: $^1$H NMR (d$_6$-acetone) δ 3.53-3.65 (m, 24H), 3.83 (t, J=4.6 Hz, 4H), 4.19 (t, J=4.6 Hz, 4H), 6.23 (d, J=2.0 Hz, 2H), 6.51 (d, J=2.0 Hz, 2H), 6.62 (s, 2H), 7.07 (d, J=9.0 Hz, 4H), 7.94 (d, J=9.0 Hz, 4H), 12.88 (s, 2H); $^{13}$C NMR (d$_6$-acetone) δ 67.8, 69.2, 70.3, 70.3, 70.5, 93.9, 98.8, 103.6, 104.4, 115.0, 123.3, 128.0, 157.6, 162.0, 162.3, 163.7, 163.9, 182.0; LRMS (ESI) m/z 875 (M$^+$+H, 3), 897 (M$^+$+Na, 100); HRMS (ESI) Calcd for $C_{46}H_{51}O_{17}$ (M$^+$+H) 875.3126, found 875.3145.

1,28-Bis[4'-((5,7-dihydroxy)-4H-chromen-4-on-2-yl)phenyl]-1,4,7,10,13,16,19,22,25,28-decaoxaoctacosane (9i): This compound was prepared from compound 22i (78 mg, 0.08 mmol), 6M HCl solution (20 mL) and THF (20 mL) as Method B described above. The titled compound (69 mg, 97%) was obtained as pale yellow oil: $^1$H NMR (d$_6$-acetone) δ 3.53-3.64 (m, 28H), 3.80 (t, J=4.6 Hz, 4H), 4.15 (t, J=4.6 Hz, 4H), 6.23 (d, J=2.0 Hz, 2H), 6.48 (d, J=2.0 Hz, 2H), 6.57 (s, 2H), 7.02 (d, J=8.8 Hz, 4H), 7.88 (d, J=8.8 Hz, 4H), 12.94 (s, 2H); $^{13}$C NMR (d$_6$-acetone) δ 67.7, 69.2, 70.3, 70.3, 70.5, 93.9, 98.9, 103.5, 104.4, 114.9, 123.2, 128.0, 157.7, 162.0, 162.3, 163.6, 164.0, 182.0; LRMS (ESI) m/z 919 (M$^+$+H, 4), 941 (M$^+$+Na, 100); HRMS (ESI) Calcd for $C_{48}H_{55}O_{18}$ (M$^+$+H) 919.3388, found 919.3399.

9-[4'-((5,7-dihydroxy)-4H-chromen-4-on-2-yl)phenyl]-3,6,9,-trioxanonan-1-ol (10a): This compound was prepared from compound 24a (28 mg, 0.06 mmol), 6M HCl solution (10 mL) and THF (10 mL) as Method B described above. The titled compound (19 mg, 75%) was obtained as pale yellow solid: m.p.: 135-137° C.; $^1$H NMR (d$_6$-DMSO) δ 3.40 (t, J=4.8 Hz, 2H), 3.45-3.59 (m, 6H), 3.75 (t, J=4.4 Hz, 2H), 4.18 (t, J=4.4 Hz, 2H), 4.57 (t, J=5.2 Hz, 1H), 6.18 (d, J=2.0 Hz, 1H), 6.48 (d, J=2.0 Hz, 1H), 6.86 (s, 1H), 7.10 (d, J=8.8 Hz, 2H), 8.00 (d, J=8.8 Hz, 2H), 10.85 (br, 1H), 12.91 (s, 1H); $^{13}$C NMR (d$_6$-DMSO) δ 60.6, 68.0, 69.2, 70.2, 70.4, 72.8, 94.4, 99.3, 103.9, 104.2, 115.4, 123.2, 128.7, 157.7, 161.8, 162.0, 163.7, 164.6, 182.2; LRMS (EI) m/z 402 (M$^+$, 100); HRMS (EI) Calcd for $C_{21}H_{22}O_8$ (M$^+$) 402.1315, found 402.1297.

12-[4'-((5,7-dihydroxy)-4H-chromen-4-on-2-yl)phenyl]-3,6,9,12-tetraoxadodecan-1-ol (10b): This compound was prepared from compound 24b (80 mg, 0.16 mmol), 6M HCl solution (10 mL) and THF (10 mL) as Method B described above. The titled compound (65 mg, 89%) was obtained as pale yellow oil: $^1$H NMR (CDCl$_3$) δ 3.61 (t, J=4.1 Hz, 2H), 3.68-3.75 (m, 10H), 3.84 (t, J=4.4 Hz, 2H), 4.05 (t, J=4.4 Hz, 2H), 6.21 (d, J=2.0 Hz, 1H), 6.28 (d, J=2.0 Hz, 1H), 6.35 (s, 1H), 6.74 (d, J=8.8 Hz, 2H), 7.52 (d, J=8.8 Hz, 2H); $^{13}$C NMR (CDCl$_3$) δ 61.4, 67.2, 69.4, 69.8, 70.4, 70.4, 70.4, 72.2, 94.2, 99.4, 103.1, 104.4, 114.4, 122.7, 127.3, 157.3, 161.2, 161.5, 163.3, 181.9; LRMS (EI) m/z 446 (M$^+$, 97); HRMS (EI) Calcd for $C_{23}H_{26}O_9$ (M$^+$) 446.1577, found 446.1574.

Compound 9j (n=10) was prepared via route A: To a stirred solution of the bis-mesylate 13b (n=10) (1 mmol) in acetonitrile (5 mL/mmol) was added solid potassium carbonate (6 mmol) and 4-hydroxybenzaldehyde (2.2 mmol) and the resulting reaction mixture was heated at 80° C. for 16 hours. After this time the reaction was filtered and the solid was washed with dichloromethane. The dichloromethane/acetonitrile mother liquor was evaporated under reduced pressure and the bis-aldehydes 11j (n=10) was obtained as a colourless oil following purification by flash column chromatography (EtOAc) (61%). $^1$H NMR (CDCl$_3$, 400 MHz): 3.6-3.75 (m, 32H), 3.87 (m, 4H), 4.20 (m, 4H), 7.01 (d, J=8.5 Hz, 4H), 7.81 (d, J=8.5 Hz, 4H), 9.87 (s, 2H); $^{13}$C NMR (CDCl$_3$, 100 MHz): 67.68, 69.40, 70.47, 70.52, 70.81, 114.83, 130.0, 131.92, 163.82, 190.82; ES-MS calcd for $C_{34}H_{51}O_{13}$ (MH$^+$) 667.3330 found 667.3345.

To a stirred solution of bis-aldehyde 11j (n=10) (1 mmol) and 2,4-dibenzyloxy-5-hydroxyacetophenone (2.1 mmol) in THF (0.25 mL/mmol) was added a solution of 60% (w/v) KOH (0.25 mL/mmol). The resulting solution was stirred at room temperature for 16 hours. After this time, the reaction mixture was poured into water and washed repeatedly with ethyl acetate until the organic layer remained colourless (typically three times). The combined organic layers were dried (MgSO4), filtered and evaporated under reduced pressure to afford the chalcone 16j (n=10) as a yellow oil following extraction into EtOAc and concentration in vacuo (>95% yield). It was used immediately in the next step without any purification. $^1$H NMR (CDCl$_3$, 400 MHz): 3.60-3.75 (m, 36H), 3.78 (m, 4H), 4.13 (m, 4H), 5.06 (s, 4H), 5.10 (s, 4H), 6.16 (d, J=2 Hz, 2H), 6.21 (d, J=2 Hz, 2H), 6.70 (d, J=8.5 Hz, 4H), 6.99 (d, J=8.5 Hz, 4H), 7.27-7.5 (m, 20H), 7.68 (d, J=16 Hz, 2H), 7.77 (d, J=16 Hz, 2H), 14.76 (s, 2H).

To a stirred solution of chalcone 16j in DMSO (minimum volume) at 150° C. was added a small amount of iodine (typically one crystal). The resulting reaction mixture was stirred at a constant temperature for a further 16 hours or until the reaction was found to be complete using $^1$H NMR spectroscopic analysis of small aliquots. After completion of the reaction, the mixture was poured into water (10 mL/mL of DMSO used) and the resulting yellow suspension was washed with ethyl acetate. Washing was continued until the organic layer remained clear (typically 3-4 times). The combined organic layers were then washed with 5% sodium thiosulfate solution, water and then dried (MgSO4), filtered and evaporated under reduced pressure to afford the flavonoid dimers 17j (n=10) as a light orange/brown oil following purification by flash column chromatography (gradient 1:5 to 1:3 acetone/DCM) (16%). $^1$H NMR (CDCl$_3$, 400 MHz): 3.6-3.75 (m, 32H), 3.87 (m, 4H), 4.19 (m, 4H), 5.10 (s, 4H), 5.20 (s, 4H), 6.44 (d, J=2 Hz, 2H), 6.58 (s, 2H), 6.62 (d, J=2 Hz, 2H), 7.01 (d, J=8.5 Hz, 4H), 7.27-7.40 (m, 16H), 7.61 (d, J=8.5 Hz, 4H), 7.79 (d, J=8.5 Hz, 4H).

Water was added dropwise to a flask containing a solution of the protected bis-flavonoid 17j in THF until the mixture just began to turn cloudy. At this point, THF was added dropwise until all material was soluble. 10% palladium on carbon (typically 1 equivalent by weight) was added and the resulting black suspension was degassed and charged with hydrogen gas. The resulting reaction mixture was stirred rapidly at room temperature until analysis by $^1$H NMR spectroscopy revealed complete removal of benzyl protecting groups. Upon completion of the reaction, the solvent was removed in vacuo to afford compound 9j (n=10) as an orange/brown oil. $^1$H NMR (d6-Acetone, 400 MHz): 3.54-3.64 (m, 32H), 3.88 (m, 4H), 4.26 (m, 4H), 6.27 (d, J=2 Hz, 2H), 6.56 (d, J=2 Hz, 2H), 6.67 (s, 2H), 7.14 (d, J=8 Hz, 4H), 8.02 (d, J=8 Hz, 4H), 13.01 (s, 2H).

Compound 9k (n=13 average) was prepared using the same procedures as described for 9j but with the dimesylate 13b (n=13 average) prepared from 13 (n=13 average) available commercially. Compound 11k (n=13 av) was obtained as a colourless oil following purification by flash column chromatography (EtOAc) (61%). $^1$H NMR (CDCl$_3$, 400 MHz) δ 3.6-3.75 (m, ~44H), 3.88 (m, 4H), 4.22 (m, 4H), 7.00 (d, J=8.5 Hz, 4H), 7.81 (d, J=8.5 Hz, 4H), 9.88 (s, 2H). Compound 16k (n=13 av) was obtained as a yellow oil following extraction into EtOAc and concentration in vacuo (>95% yield). It was used immediately in the next step without any purification. $^1$H NMR (CDCl$_3$, 400 MHz): 3.60-3.75 (m, ~44H), 3.80 (m, 4H), 4.14 (m, 4H), 5.07 (s, 4H), 5.10 (s, 4H), 6.18 (d, J=2 Hz, 2H), 6.23 (d, J=2 Hz, 2H), 6.73 (d, J=8.5 Hz, 4H), 7.03 (d, J=8.5 Hz, 4H), 7.27-7.5 (m, 20H), 7.69 (d, J=16 Hz, 2H), 7.77 (d, J=16 Hz, 2H), 14.76 (s, 2H). Compound 17k (n=13 av) was isolated as a light orange/brown oil following purification by flash column chromatography (gradient 1:5 to 1:3 acetone/DCM) (28%). $^1$H NMR (CDCl$_3$, 400 MHz): 3.6-3.75 (m, ~44H), 3.89 (m, 4H), 4.20 (m, 4H), 5.13 (s, 4H), 5.23 (s, 4H), 6.47 (bs 2H), 6.56 (bs, 2H), 6.62 (bs, 2H), 7.00 (m, 4H), 7.27-7.40 (m, 16H), 7.61 (m 4H), 7.78 (m, 4H). Compound 9k (n=13 av) was obtained as an orange/brown oil. $^1$H NMR (d6-Acetone, 400 MHz): 3.54-3.64 (m, ~44H), 3.87 (m, 4H), 4.26 (m, 4H), 6.27 (br, 2H), 6.55 (br, 2H), 6.70 (br, 2H), 7.1 (m, 4H), 8.0 (m, 4H).

Synthesis of Polyethylene Glycol Linked Apigenin Analog Dimers

General procedure for the synthesis of chalcone 32a-l: To a round-bottom flask was charged with 2'-hydroxyacetophenone 31 (1.0 equiv.), 4-allyloxybenzaldehyde (1.0 equiv.) and excess potassium hydroxide solution (3M solution in 96% EtOH). The mixture was stirred at room temperature for 16 h. When TLC indicated complete consumption of 2'-hydroxyacetophenone, the reaction mixture was acidified to pH 5 with 1 M HCl solution at ice-bath temperature. The mixture was continuously extracted with CH$_2$Cl$_2$ (30 mL×3). The combined organic layers were dried over MgSO$_4$, filtered and evaporated under reduced pressure to give a crude mixture, which was washed with 5% ethyl acetate in hexane to furnish desired chalcone.

General procedure for the synthesis of flavone 33a-l: To a well-stirred solution of chalcone 32 in dimethyl sulfoxide at 50° C., was added catalytic amount of iodine (4 mol %) once. The reaction mixture was then stirred at 130° C. for 12 h. During heating, the reaction mixture turned slowly from pale brown to dark brown in color. When TLC indicated complete consumption of chalcone 32, the reaction mixture was poured into a separating funnel containing water (200 mL). The mixture was extracted with CH$_2$Cl$_2$ (30 mL×3). If the mixture could not be separated into two layers, 1M HCl (20 mL) was added. The combined organic layers were washed with 0.5% sodium thiosulfate solution, dried over MgSO$_4$, filtered and evaporated to give a crude reaction mixture, which was subjected to crystallization to afford desired flavone 33.

General procedure for the synthesis of 34a-l by the deprotection of allyl group of flavone 33a-l: To a round-bottom flask charged with flavone 33 (1 equiv.), K$_2$CO$_3$ (6 equiv.) and MeOH at refluxing temperature, was added catalytic amount of Pd(PPh$_3$)$_4$ (2 mol %) once. The reaction mixture was stirred at refluxing temperature for 2 h. When TLC indicated complete consumption of 33, the reaction mixture was poured into a beaker containing water (200 mL). The solution was acidified to pH 4 using 1 M HCl solution and numerous off-white solid was formed, which was collected by suction filtration. The collected solid was dissolved in acetone and the insoluble dark charcoal was removed by filtration. The brown filtrate obtained was evaporated under reduced pressure to furnish titled compound 34. Some of these flavones have been previously reported in the literature [Cpd 33a—Huang, X.; Tang, E.; Xu, W.-M.; Cao, J. *J. Comb. Chem.* 2005, 7, 802-805. Cpd 34a—Miyake, H.; Takizawa, E.; Sasaki, M.; *Bull. Chem. Soc. Jpn.,* 2003, 76, 835-836. Cpd 34d—Jesthi, P. K.; Sabat, B. K.; Rout, M. K. *J. Indian Chem. Soc.* 1965, 42, 105-108. Cpd 34e—Ono, M.; Yoshida, N.; Ishibashi, K.; Haratake, M.; Arano, Y.; Mori, H.; Nakayama, M. *J. Med. Chem.,* 2005, 48, 7253-7260. Cpd 34f—Jha, B. C.; Amin, G. C. *Tetrahedron* 1958, 2, 241-245. Cpd 34i—Pelter, A.; Bradshaw, J.; Warren, R. *Phytochemistry* 1971, 10, 835-850. Cpd 34i—Pelter, A.; Ward, R. S.; Balasubramanian, M. *Chem. Comm.* 1976, 4, 151-152. Cpd 34j and Cpd 34k—Prendergast, Patrick T. Use of flavones, coumarins and related compounds to treat infections. PCT Int. Appl. (2001), 70 pp. Cpd 34l—Bargellini, G.; Grippa, A. *Gazzetta Chimica Italiana* 1927, 57, 605-609.].

General procedure for the synthesis of flavone diners 35a-l: To a round-bottom flask was charged with flavone 34 (1.6 equiv.), tetraethylene glycol dimesylate (1.0 equiv.), K$_2$CO$_3$ (4 equiv.) and DMF. The reaction mixture was stirred at refluxing temperature for 2 to 3 h. During heating, the reaction mixture turned slowly from deep brown to milky in color. When TLC indicated complete consumption of flavone 34, the reaction mixture was poured into a separating funnel containing water (200 mL). The mixture was continuously extracted with CH$_2$Cl$_2$ (20 mL×3). If the mixture could not be separated into two layers, 1M HCl (20 mL) was added. The combined organic layers were dried over MgSO$_4$, filtered and evaporated to give a crude reaction mixture. Purification of the flavone dimer 35 was performed by crystallization from acetone or flash column chromatography on silica gel (20% acetone in CH$_2$Cl$_2$ as eluent) as indicated below.

1,13-Bis[4'-(4H-chromen-4-on-2-yl)phenyl]-1,4,7,10,13-pentaoxamidecane (35a) After flash column chromatography on silica gel, the titled compound (0.98 g, 37%) was obtained as pale yellow solid: $^1$H NMR (CDCl$_3$) 3.63-3.67 (m, 8H), 3.79 (t, J=4.8 Hz, 4H), 4.06 (t, J=4.4 Hz, 4H), 6.57 (s, 2H), 6.87 (d, J=8.8 Hz, 4H), 7.25 (dd, J=7.6, 7.6 Hz, 2H), 7.37 (d, J=8.0 Hz, 2H), 7.53 (ddd, J=1.2, 7.6, 7.6 Hz, 2H), 7.68 (d, J=8.8 Hz, 4H), 8.06 (dd, J=0.8, 7.6 Hz, 2H); $^{13}$C NMR (CDCl$_3$) δ 67.3, 69.2, 70.4, 70.5, 105.6, 114.6, 117.6, 123.5, 123.5, 124.7, 125.1, 127.5, 133.3, 155.7, 161.3, 162.8, 177.9.

1,13-Bis[4'-(7-fluoro-4H-chromen-4-on-2-yl)phenyl]-1,4,7,10,13-pentaoxamidecane (35b) After flash column chromatography on silica gel, the titled compound (0.15 g, 54%) was obtained as pale yellow solid: $^1$H NMR (CDCl$_3$) 3.68-3.74 (m, 8H), 3.87 (t, J=4.8 Hz, 4H), 4.16 (t, J=4.4 Hz, 4H), 6.65 (s, 2H), 6.98 (d, J=8.8 Hz, 4H), 7.08 (t, J=7.6 Hz, 2H), 7.16 (d, J=8.0 Hz, 2H), 7.77 (d, J=8.8 Hz, 4H), 8.17 (dd, J=6.4, 8.8 Hz, 2H); $^{13}$C NMR (CDCl$_3$) δ 67.6, 69.5, 70.6, 70.8, 104.5, 104.7, 106.0, 113.6, 113.8, 115.0, 120.6, 123.6, 127.9, 156.9, 157.1, 161.7, 163.5, 164.2, 166.8, 177.3.

1,13-Bis[4'-(6-fluoro-4H-chromen-4-on-2-yl)phenyl]-1,4,7,10,13-pentaoxamidecane (35c) After flash column chromatography on silica gel, the titled compound (0.13 g, 55%) was obtained as white solid: m.p.: 147-149° C.; $^1$H NMR (CDCl$_3$) 3.66-3.75 (m, 8H), 3.88 (t, J=4.4 Hz, 4H), 4.17 (t, J=4.8 Hz, 4H), 6.68 (s, 2H), 6.98 (d, J=8.8 Hz, 4H), 7.36 (dt, J=0.4, 6.0 Hz, 2H), 7.49 (dd, J=4.0, 8.8 Hz, 2H), 7.80 (d, J=8.0 Hz, 6H); $^{13}$C NMR (CDCl$_3$) δ 67.6, 69.5, 70.6, 70.8, 105.3, 110.4, 110.6, 115.0, 120.0, 121.5, 121.8, 123.7, 124.9, 127.9, 152.2, 158.2, 160.7, 161.7, 163.5, 177.4.

1,13-Bis[4'-(6-chloro-4H-chromen-4-on-2-yl)phenyl]-1,4,7,10,13-pentaoxamidecane (35d) After crystallization from acetone, the titled compound (48 mg, 31%) was obtained as yellow solid: m.p.: 180-182° C.; $^1$H NMR (CDCl$_3$) 3.70-3.76 (m, 8H), 3.90 (t, J=4.8 Hz, 4H), 4.18 (t, J=4.8 Hz, 4H), 6.70 (s, 2H), 7.00 (d, J=8.8 Hz, 4H), 7.47 (d, J=8.8 Hz, 2H), 7.60 (dd, J=2.8, 8.8 Hz, 2H), 7.81 (d, J=8.8 Hz, 4H) 8.14 (d, J=2.4 Hz, 2H); $^{13}$C NMR (CDCl$_3$) δ 67.6, 69.5, 70.7, 70.8, 105.9, 115.0, 119.6, 123.6, 124.8, 125.1, 127.9, 131.0, 133.7, 154.4, 161.8, 163.5, 177.0; LRMS (ESI) m/z 703 (M$^+$+H, 10), 725 (M$^+$+Na, 37); HRMS (ESI) Calcd for C$_{38}$H$_{33}$O$_9$Cl$_2$ (M$^+$+H) 703.1502, found 703.1505.

1,13-Bis[4'-(6-bromo-4H-chromen-4-on-2-yl)phenyl]-1,4,7,10,13-pentaoxamidecane (35e) After flash column chromatography on silica gel, the titled compound (43 mg, 34%) was obtained as yellow solid: m.p.: 184-186° C.; $^1$H NMR (CDCl$_3$) 3.69-3.75 (m, 8H), 3.88 (t, J=4.8 Hz, 4H), 4.17 (t, J=4.8 Hz, 4H), 6.68 (s, 2H), 6.98 (d, J=8.8 Hz, 4H), 7.38 (d, J=9.2 Hz, 2H), 7.71 (dd, J=2.4, 8.8 Hz, 2H), 7.78 (d, J=8.8 Hz, 4H) 8.27 (d, J=2.0 Hz, 2H); $^{13}$C NMR (CDCl$_3$) δ 67.6, 69.5, 70.6, 70.8, 106.0, 115.0, 119.8, 123.6, 125.1, 127.9, 128.2, 136.5, 154.8, 161.8, 163.5, 176.9; LRMS (ESI) m/z 793 (M$^+$+H, 8), 815 (M$^+$+Na, 20); HRMS (ESI) Calcd for C$_{38}$H$_{33}$O$_9$Br$_2$ (M$^+$+H) 791.0491, found 791.0506.

1,13-Bis[4'-(6,8-dichloro-4H-chromen-4-on-2-yl)phenyl]-1,4,7,10,13-pentaoxamidecane (35f) After flash column chromatography on silica gel, the titled compound (45 mg, 28%) was obtained as white solid: m.p.: 147-148° C.; $^1$H NMR (CDCl$_3$) 3.70-3.76 (m, 8H), 3.90 (t, J=4.8 Hz, 4H), 4.18 (t, J=4.4 Hz, 4H), 6.71 (s, 2H), 7.00 (d, J=8.8 Hz, 4H), 7.67 (d, J=2.4 Hz, 2H), 7.85 (d, J=8.8 Hz, 2H), 8.03 (d, J=2.8 Hz, 2H); $^{13}$C NMR (CDCl$_3$) δ 67.7, 69.5, 70.7, 70.8, 105.6, 115.1, 123.1, 123.8, 124.2, 125.6, 128.1, 130.7, 133.5, 150.2, 162.0, 163.3, 176.2; LRMS (ESI) m/z 773 (M$^+$+H, 29), 795 (M$^+$+Na, 100); HRMS (ESI) Calcd for C$_{38}$H$_{31}$O$_9$Cl$_4$ (M$^+$+H) 771.0722, found 771.0730.

1,13-Bis[4'-(7-methyl-4H-chromen-4-on-2-yl)phenyl]-1,4,7,10,13-pentaoxamidecane (35g) After flash column chromatography on silica gel, the titled compound (0.12 g, 33%) was obtained as white solid: m.p.: 128-129° C.; $^1$H NMR (CDCl$_3$) 2.45 (s, 6H), 3.68-3.75 (m, 8H), 3.87 (t, J=4.4 Hz, 4H), 4.16 (t, J=4.4 Hz, 4H), 6.66 (s, 2H), 6.98 (d, J=8.8 Hz, 4H), 7.16 (d, J=8.0 Hz, 2H), 7.28 (s, 2H), 7.79 (d, J=8.4 Hz, 4H), 8.03 (d, J=8.0 Hz, 2H); $^{13}$C NMR (CDCl$_3$) δ 21.8, 67.6, 69.5, 70.7, 70.8, 105.9, 114.9, 117.7, 121.5, 124.1, 125.2, 126.5, 127.8, 144.9, 156.2, 161.5, 163.0, 178.3; LRMS (ESI) m/z 663 (M$^+$+H, 97), 685 (M$^+$+Na, 100); HRMS (ESI) Calcd for C$_{40}$H$_{39}$O$_9$ (M$^+$+H) 663.2594, found 663.2588.

1,13-Bis[4'-(6-methyl-4H-chromen-4-on-2-yl)phenyl]-1,4,7,10,13-pentaoxamidecane (35h) After flash column chromatography on silica gel, the titled compound (47 mg, 36%) was obtained as white solid: m.p.: 139-140° C.; $^1$H NMR (CDCl$_3$) 2.42 (s, 6H), 3.69-3.75 (m, 8H), 3.88 (t, J=4.4 Hz, 4H), 4.16 (t, J=4.4 Hz, 4H), 6.69 (s, 2H), 6.98 (d, J=8.4 Hz, 4H), 7.38 (d, J=8.4 Hz, 2H), 7.44 (dd, J=1.6, 8.4 Hz, 2H), 7.80 (d, J=8.4 Hz, 4H), 7.94 (s, 2H); $^{13}$C NMR (CDCl$_3$) δ 20.9, 67.6, 69.5, 70.6, 70.8, 105.9, 114.9, 117.6, 123.4, 124.1, 124.9, 127.8, 134.8, 135.0, 154.3, 161.5, 163.1, 178.4; LRMS (ESI) m/z 663 (M$^+$+H, 79), 685 (M$^+$+Na, 100); HRMS (ESI) Calcd for C$_{40}$H$_{39}$O$_9$ (M$^+$+H) 663.2594, found 663.2586.

1,13-Bis[4'-(7-methoxy-4H-chromen-4-on-2-yl)phenyl]-1,4,7,10,13-pentaoxamidecane (35i) After flash column chromatography on silica gel, the titled compound (95 mg, 33%) was obtained as pale yellow solid: m.p.: 128-130° C.; $^1$H NMR (CDCl$_3$) 3.69-3.75 (m, 8H), 3.88 (t, J=4.4 Hz, 4H), 3.90 (s, 6H), 4.17 (t, J=4.4 Hz, 4H), 6.65 (s, 2H), 6.89 (d, J=2.0 Hz, 2H), 6.93 (dd, J=2.0, 8.4 Hz, 2H), 6.99 (d, J=8.8 Hz, 4H), 7.79 (d, J=8.4 Hz, 4H), 8.07 (d, J=8.8 Hz, 2H); $^{13}$C NMR (CDCl$_3$) δ 55.8, 67.6, 69.5, 70.7, 70.8, 100.3, 105.9, 114.2, 114.9, 117.6, 124.1, 126.9, 127.7, 157.8, 161.4, 162.9, 164.0, 177.8; LRMS (ESI) m/z 695 (M$^+$+H, 63), 717 (M$^+$+Na, 100); HRMS (ESI) Calcd for C$_{40}$H$_{39}$O$_{11}$ (M$^+$+H) 695.2492, found 695.2495.

1,13-Bis[4'-(6-methoxy-4H-chromen-4-on-2-yl)phenyl]-1,4,7,10,13-pentaoxamidecane (35j) After crystallization from acetone, the titled compound (0.17 g, 45%) was obtained as white solid: m.p.: 129-130° C.; $^1$H NMR (CDCl$_3$) 3.70-3.74 (m, 8H), 3.87 (s, 6H), 3.88 (t, J=4.4 Hz, 4H), 4.16 (t, J=4.4 Hz, 4H) 6.70 (s, 2H), 6.98 (d, J=8.8 Hz, 4H), 7.24 (dd, J=2.8, 8.8 Hz, 2H), 7.43 (d, J=9.2 Hz, 2H), 7.53 (d, J=2.8 Hz, 2H), 7.80 (d, J=8.8 Hz, 4H); $^{13}$C NMR (CDCl$_3$) δ 55.9, 67.6, 69.5, 70.7, 70.8, 104.7, 105.3, 114.9, 119.3, 123.5, 124.3, 127.8, 150.9, 156.8, 161.5, 163.1, 178.1; LRMS (ESI) m/z 695 (M$^+$+H, 47), 717 (M$^+$+Na, 100); HRMS (ESI) Calcd for C$_{40}$H$_{39}$O$_{11}$ (M$^+$+H) 695.2492, found 695.2493.

1,13-Bis[4'-(5-methoxy-4H-chromen-4-on-2-yl)phenyl]-1,4,7,10,13-pentaoxamidecane (35k) After flash column chromatography on silica gel, the titled compound (0.11 g, 39%) was obtained as white solid: m.p.: 60-61° C.; $^1$H NMR (CDCl$_3$) 3.68-3.72 (m, 8H), 3.86 (t, J=4.8 Hz, 4H), 3.95 (s, 6H), 4.14 (t, J=4.4 Hz, 4H), 6.61 (s, 2H), 6.77 (d, J=8.0 Hz, 2H), 6.96 (d, J=8.8 Hz, 4H), 7.05 (d, J=8.4 Hz, 2H), 7.51 (dd, J=8.0, 8.0 Hz, 2H), 7.77 (d, J=8.8 Hz, 2H); $^{13}$C NMR (CDCl$_3$) δ 56.4, 67.5, 69.5, 70.6, 70.8, 106.3, 107.5, 110.0, 114.8, 123.6, 127.6, 133.5, 158.1, 159.6, 161.0, 161.3, 178.2.

1,13-Bis[4'-(6,7-dimethoxy-4H-chromen-4-on-2-yl)phenyl]-1,4,7,10,13-pentaoxamidecane (35l) After crystallization from acetone, the titled compound (0.11 g, 39%) was obtained as white solid: m.p.: 71-72° C.; $^1$H NMR (CDCl$_3$) 3.67-3.71 (m, 8H), 3.85 (t, J=4.8 Hz, 4H), 3.89 (s, 6H), 3.95 (s, 6H), 4.12 (t, J=4.4 Hz, 4H), 6.60 (s, 2H), 6.85 (s, 2H), 6.92 (d, J=8.8 Hz, 4H), 7.40 (s, 2H), 7.71 (d, J=8.8 Hz, 4H); $^{13}$C NMR (CDCl$_3$) δ 56.1, 56.3, 67.5, 69.4, 70.6, 70.7, 99.5, 104.0, 105.3, 114.8, 116.9, 124.0, 127.5, 147.3, 151.9, 154.1, 161.2, 162.5, 177.3; LRMS (ESI) m/z 755 (M$^+$+H, 48), 777 (M$^+$+Na, 100); HRMS (ESI) Calcd for C$_{42}$H$_{42}$O$_{13}$Na (M$^+$+Na) 777.2523, found 777.2512.

Potency of Polyethylene Glycol Linked Apigenin Dimers

The potency of a series of apigenin dimers 9a-9k, linked with 1 to 13 ethylene glycol units, are evaluated in sensitizing different MDR cancer cells. Their activities are compared with apigenin itself as well as the monomers 10a and 10b. Their abilities to reverse drug efflux mediated by P-gp have also been evaluated.

Recent evidence has shown that some P-gp and MRP transporters are involved in drug resistance in the protozoan parasite *Leishmania* (Chemosensitizers in drug transport mechanisms involved in protozoan resistance. *Curr. Drug Targets Infect. Disord.* 2005, 5, 411-31). Resistance to pentavalent antimonials sodium stibogluconate (SSG) in *L. tarentolae* is due to a MRP member (LtPGPA). It has been reported that pentamidine resistance may be due to the exclusion of pentamidine from its target, mitochondria (Pentamidine uptake in *Leishmania donovani* and *Leishmania amazonensis* promastigotes and axenic amastigotes. *Biochem. J.* 1996, 315 (Pt 2), 631-4). As some flavonoids have been considered in the modulation of P-gp-type MDR in cancers and have been able to inhibit a variety of ATP-binding proteins such as plasma membrane ATPase, cyclic AMP-dependent protein kinase and protein kinase C, it is considered in this invention that the flavonoid dimers of this invention would increase the efficacy of apigenin in binding to NBD, thereby inactivating P-gp, thereby modulating MDR activity in *Leishmania* cells that are resistant to pentamidine and SSG.

Materials and Methods

Materials. DMSO, Verapamil, Doxorubicin, Daunorubicin, Vincristine, Vinblastine, paclitaxel (taxol) and Mitoxantrone were purchased from Sigma-Aldrich. Dulbecco's Modified Eagle's Medium (DMEM), RPMI 1640 Medium, Trypsin-EDTA and Penicillin/Streptomycin were from Gibco BRL. Fetal bovine serum (FBS) was from HyClone Laboratories. MTS, Phenazine methosulfate (PMS) and Pgp-Glo™ Assay System with P-glycoprotein were purchased from Promega. Human breast cancer cell lines MDA435/LCC6 and MDA435/LCC6 MDR were kindly provided by Dr. Robert Clarke (Georgetown University, Washington, D.C.). Murine leukemia cell lines P388 and P388/ADR were obtained from the National Cancer Institute (Maryland, USA).

Drug Resistance in Cancer Chemotherapy

Cell Culture.

MDA435/LCC6 and P388 (both parent and MDR subtype) were maintained in DMEM and RPMI 1640 culture medium supplemented with 10% FBS, respectively. RPMI 1640 media also contained 100 units/ml penicillin and 100 μg/ml streptomycin. Cells were cultured at 37° C. in a humidified atmosphere with 5% $CO_2$. A solution of 0.05% trypsin-EDTA was used to detach the MDA435/LCC6 (both wild type and MDR subtype) cells.

Cell proliferation assay. MDA435/LCC6 and P388 (both parent and MDR subtype) cells were seeded at 2000 and 5000 cells per well, respectively, in 96-well plates. Varying concentrations of anticancer drugs (Doxorubicin, Daunorubicin, Vincristine, Vinblastine, taxol, Mitoxantrone) with or without the flavonoid dimers were added in a final volume of 200 μl and cells were grown for 4 and 3 days for MDA435/LCC6 and P388 (both parent and MDR subtype) cells, respectively. For MDA435/LCC6 (both parent and MDR subtype), the corresponding drugs were added after cell attachment (24 hr incubation). To measure cell proliferation, the cell Titer 960 Aqueous Assay (Promega) was used according to the manufacturer's instructions. Briefly, MTS (2 mg/ml) and PMS (0.92 mg/ml) were mixed in a ratio of 20:1. 30 μl MTS/PMS mixture was added into each well and incubated for 2 hours at 37° C. Optical absorbance at 490 nm was then recorded using an ELISA microtiter plate reader (Bio-Rad). Each experiment was done at least in triplicate and repeated twice. Cytotoxicity of the anticancer drugs was expressed as the fraction of the cells survived relative to the untreated DMSO (0.05%) solvent controls. $IC_{50}$ or $IC_{60}$ of the anticancer drugs was expressed as the concentration of the drugs inhibiting cell growth by 50% or 60%, respectively.

Doxorubicin accumulation. 2.5 ml ($10^5$ cells/ml) MDA435/LCC6 (both parent and MDR subtype) cells were seeded in each well of 6-well plates. At confluence, culture medium was removed. 2 ml of fresh DMEM with modulators was added and cells were incubated for 30 min at 37° C. Doxorubicin (final concentration of 20 μM) was then added and incubated for 2 h at 37° C. The cells were then harvested by trypsinization.

For P388 (both parent and MDR subtype) cells, 1 ml ($10^5$ cells) confluent cells were aliquot into Eppendorf tube and pre-incubated with flavone dimers for 30 min at 37° C. Doxorubicin (final concentration of 10 μM) was then added and incubated for 2 h at 37° C. at a final concentration of 10 μM. The cell pellets were washed 3 times with cold PBS by using an Eppendorf micro-centrifuge and lysed with 0.3N HCL in 50% ethanol, and sonicated for 30s. After centrifugation at 10000 rpm/min for 3 min, the supernatant was saved. The fluorescence of doxorubicin was measured using a spectrofluorometer ($\lambda_{excite}$=470 nm, $\lambda_{emit}$=585 nm).

ATPase Assay. P-gp ATPase activity was measured using Pgp-Glo™ Assay System with human P-gp membrane by following the manufacturer's instruction. The assay relies on the ATP dependence of the light-generating reaction of firefly luciferase. Briefly, 25 μg P-gp membrane was incubated at 37° C. with $Na_3VO_4$ (100 μM), solvent control (0.1% DMSO), 9d (100 μM), verapamil (100 μM) or verapamil (100 μM) plus 9d (100 μM). The ATPase reaction was initiated by the adding 5 mM MgATP and followed by incubation for 40 min at 37° C. The reaction was stopped, and the remaining unmetabolized ATP was detected as a luciferase-generated luminescence signal by addition of ATP Detection Reagent. Following a 20 minute room temperature signal-stabilization period, luminescence was read on a BMG Fluostar plate luminometer. P-gp ATPase activity was presented as drop in luminescence of samples compared to that treated with $Na_3VO_4$.

Results

Apigenin dimers 9a to 9k alone have no anticancer activity to the tested MDR cell lines at a concentration below 5 μM, as well as at 10 μM for the monomers 10a and 10b. Therefore 5 μM apigenin dimers and 10 μM monomers were chosen to evaluate their chemosensitizing effect in the following assays.

Effect of Flavonoid Dimers on Reversing Taxol Resistance in MDA435/LCC6 MDR Cells MDA435/LCC6 is an estrogen-independent human breast cancer cell line. Its MDR subtype (MDA435/LCC6 MDR) was generated by transducing a retroviral vector directing the constitutive expression of the human MDR1 cDNA, producing a cell line with a classical MDR1 resistance pattern (MDA435/LCC6 and MDA435/LCC6MDR1: ascites models of human breast cancer. *Br J Cancer* 1996, 73, 154-161). The ability of the apigenin dimers of this invention to reverse taxol resistance in MDA435/LCC6 MDR cells were tested. Taxol is one of the first-line drugs of choice for treating breast cancer and it has been shown that taxol resistance is mediated by P-gp. Verapamil at 5 μM was used as a positive control. Apigenin monomers 10a and 10b at 10 μM were used as the negative controls. As shown in FIG. 3A, different dimers potentiated the toxicity of taxol by different extent. Compound 9d with spacer length of 4 PEGs exhibited the most dramatic reversal activity by reducing the $IC_{50}$ of taxol by about 26 relative folds (RF) from 115 nM to 4.4 nM. Its potency was comparable to verapamil ($IC_{50}$=5.2 nM). Compounds 9b and 9c with spacer length of 2 and 3 PEGs also significantly reversed taxol resistance by reducing the $IC_{50}$ by 5.8 and 5.4 RF to 19.9 nM and 21.5 nM, respectively. However, dimers with spacers shorter than 2 PEGs (9a) or longer than 5 PEGs (9e, 9f, 9h, 9j, 9k) showed little or no reversing effect at 5 μM. Apigenin monomers with 3 and 4 PEG (10a and 10b) were used as the negative controls in these experiments to determine whether the anticancer resistance reversal activity is due solely to the dimeric nature of the synthetic modulators, which were found to have little reversing effect even when used at double the concentration (10 μM) as that of the dimers 9c and 9d (5 μM) with the same number of ethylene glycol units. These results suggest that the modulating activity of 9d, 9c and 9b is due to their bivalent structures, and not due to the simple increase in the number of apigenin moieties present.

The reversal of taxol resistance by 9d in MDA435/LCC6 MDR cells was also concentration-dependent (FIG. 3B). A concentration of 1 µM 9d was able to reduce $IC_{50}$ about 1.9 RF. Increasing the concentration of 9d further increases the reversing activity with 5 µM reaching the plateau.

Effect of Apigenin Dimers on Reversing Resistance to Other Anticancer Drugs in MDA435/LCC6 MDR Cells.

Figure 5:
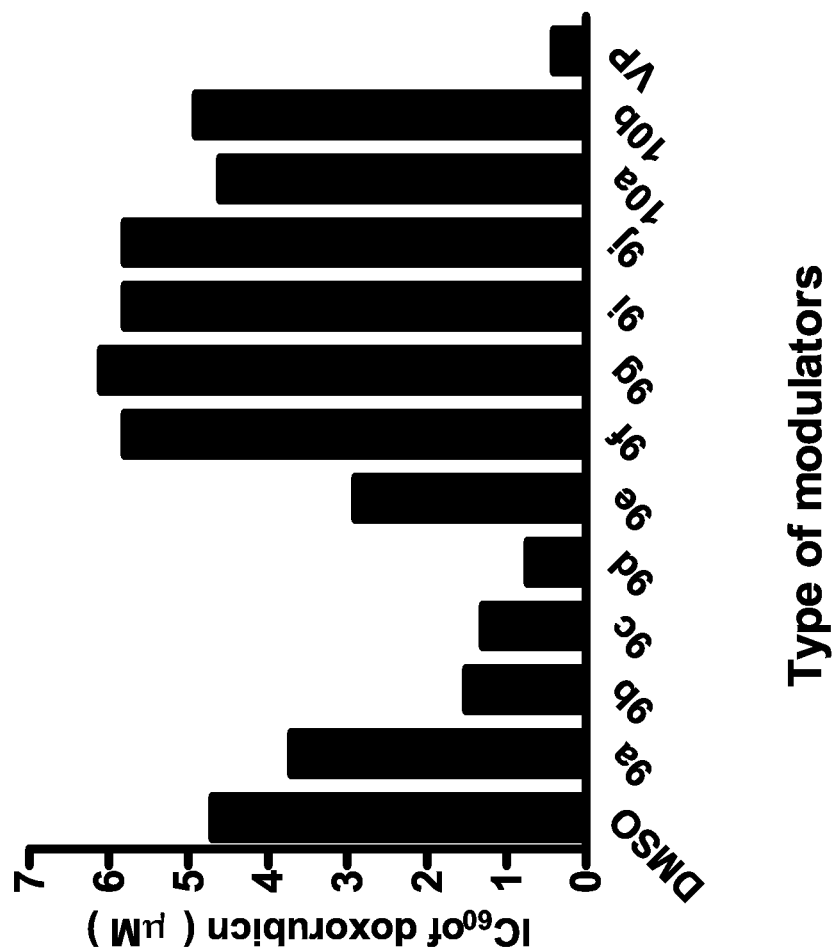
FIG. 5 shows the effects of apigenin monomers and dimers on doxorubicin cytotoxicity in MDA435LCC6 MDR cells.

Similar trend of chemosensitizing effect by different apigenin dimers in vinblastine resistance was observed (FIG. 4A). FIG. 4A shows that 9d exhibited the greatest efficacy in potentiating the cytotoxicity of vinblastine, reducing the $IC_{50}$ values by about 13 RF, from 4.8 nM to 0.36 nM. The potency of 9d was similar to that of verapamil ($IC_{50}$=0.25 nM). Compounds 9b and 9c have lower but still very high activity in reducing the $IC_{50}$ by 7.9 RF and 5.5 RF to 0.61 nM and 0.87 nM, respectively, comparing with 9d. Other dimers with shorter (9a) or longer spacers (9e, 9f, 9h, 9j, 9k) have little or no activity. Monomers 10a and 10b, at double the concentration used (10 µM), were also ineffective. Compound 9d also exhibited a dose dependent effect in potentiating vinblastine cytotoxicity (FIG. 4B). Similarly, 9d is more effective than others in potentiating doxorubicin cytotoxicity, reducing the $IC_{60}$ by about 6 RF from 4.7 µM to 0.73 µM (FIG. 5). Compounds 9c ($IC_{60}$=1.3 µM) and 9b ($IC_{60}$=1.3 µM) also showed high efficacy in reducing the $IC_{60}$ by about 3.6 and 3.1 RF, respectively. Apigenin dimers with shorter (9a) or longer PEGs (9e, 9f, 9h, 9j, 9k) gave very little or no doxorubicin sensitization. Monomers (10a and 10b) were ineffective reversers as well.

Compound 1d can Reverse MDR of MDA435/LCC6 MDR to Almost Parental Level

Figure 6A:
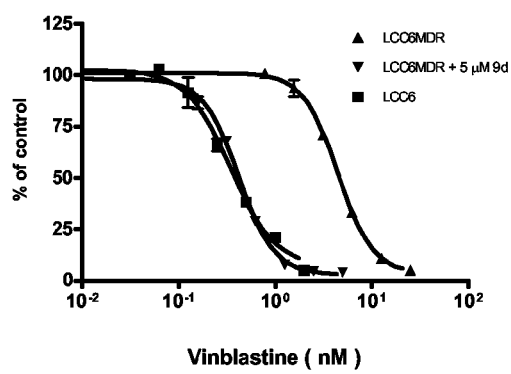
FIG. 6 shows the proliferation of MDA435LCC6 MDR and MDA435LCC6 cells in the presence of anticancer drugs (A) vinblastine, (B) taxol, (C) doxorubicin, (D) vincristine, (E) daunorubicin, and (F) mitoxantrone with or without 5 μM 9d.
Figure 6B:
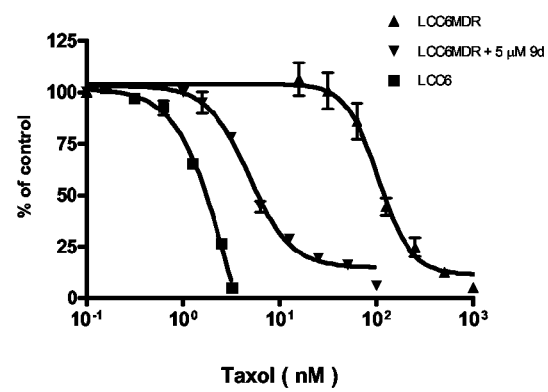
Figure 6C:
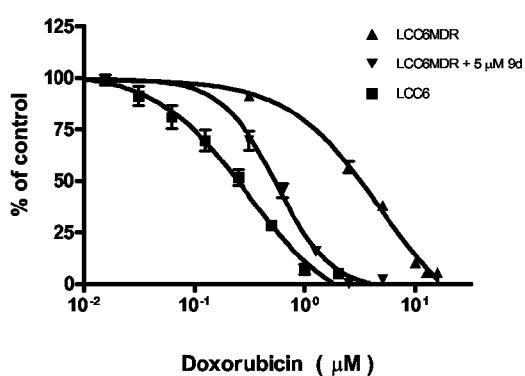
Figure 6D:
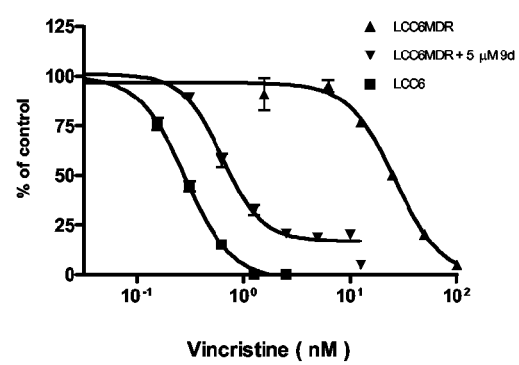
Figure 6E:
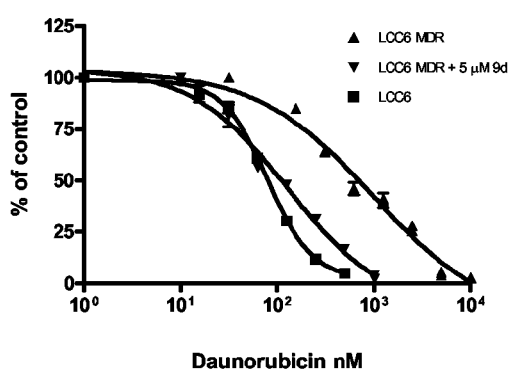
Figure 6F:
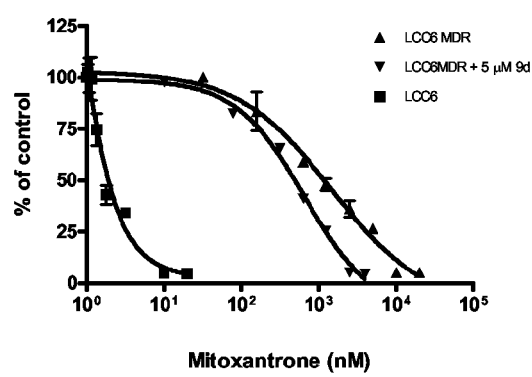

Since compound 9d consistently showed the highest modulating activity against taxol, vinblastine and doxorubicin, we therefore focused on investigating whether 9d can reverse the resistance of MDA435/LCC6 MDR back to that of the parental level (MDA435/LCC6). FIG. 6A to 6E indicated that 5 µM of 9d can reverse resistance of MDA435/LCC6 MDR to vinblastine, taxol, doxorubicin, vincristine, daunorubicin to a level close to the parental (MDA435/LCC6) level. No effect was observed in mitoxantrone (FIG. 6F). The reversing ability, as determined by the relative fold changes in the $IC_{50}$ of drugs with or without 9d, is summarized in Table 1. It ranges from 7.6 to 41 RF. The reversing activity for vinblastine and taxol are particularly impressive as the $IC_{50}$ can be lowered to almost the same level as in the sensitive counterparts.

Effect of Apigenin Dimers on Cellular Accumulation of Doxorubicin in MDA435/LCC6 and MDA435/LCC6 MDR Cells In order to understand whether the modulating activity for various anticancer drugs by different dimers is due to their different ability to modulate P-gp mediated drug efflux, their effects on the accumulation of doxorubicin in both MDA435/LCC6 sensitive and resistant cells were investigated. Doxorubicin was a fluorescent drug substrate of P-gp and was used in this experiment to monitor the P-gp mediated drug efflux. Accumulation of doxorubicin in these cells was determined in the presence or absence of apigenin dimers (10 µM) and monomer (20 µM). Verapamil was used as a positive control.

Figure 7B:
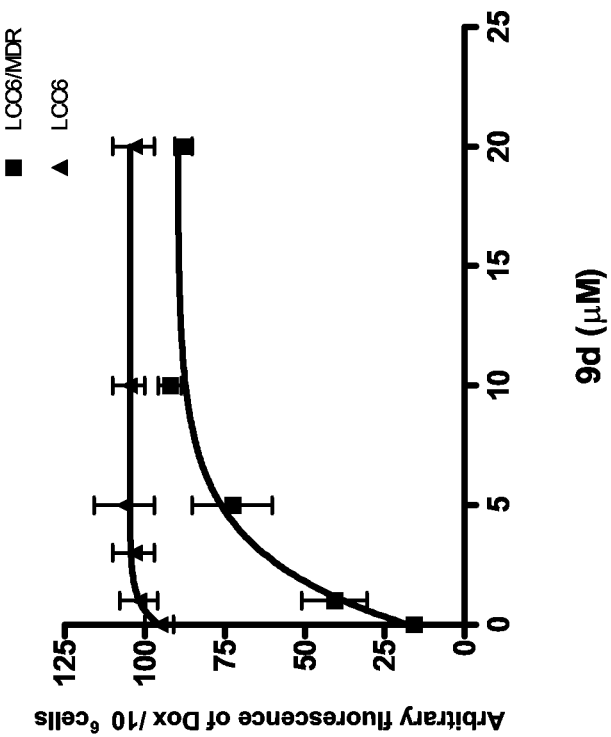
FIG. 7 shows the intracellular accumulation of doxorubicin in MDA435LCC6 MDR and MDA435LCC6 cells treated with (A) different modulators and (B) different concentrations of 9d (0-20 μM)
Figure 7A:
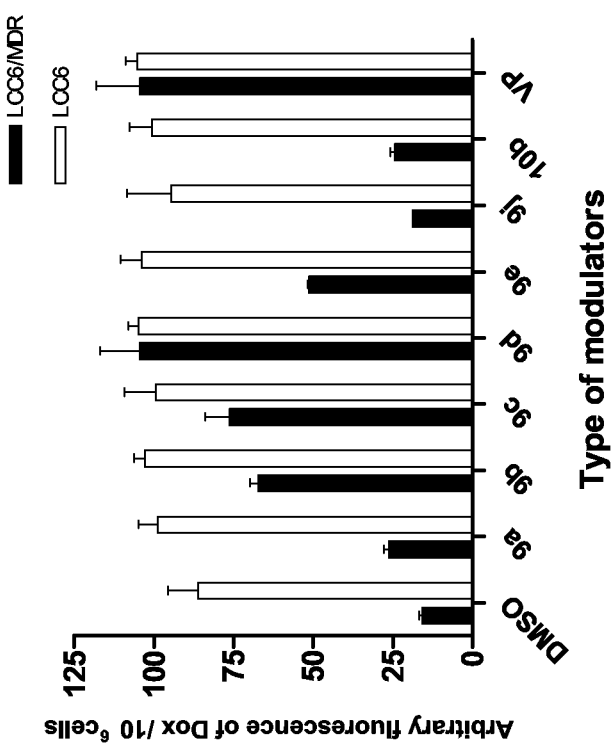

The results are shown in FIG. 7A. Accumulation of doxorubicin in LCC6, with basal level of P-gp expression, is unaffected by treatment either with solvent control (DMSO) or various apigenin monomers, dimers or verapamil. For LCC6 MDR cells, the accumulation level of doxorubicin, when treated with DMSO control, was found to be at around 20% of that of LCC6. This is due to the P-gp mediated doxorubicin efflux found in LCC6 MDR cells. Such low level of accumulation, however, was completely reversed by co-treatment with 9d. At 10 µM, 9d enhanced doxorubicin accumulation of LCC6 MDR cells by 5.8 folds. The accumulation of doxorubicin is now almost the same (97%) as that of the 9d-treated LCC6 cells. This potency is comparable to that of verapamil (6.2 folds). Compounds 9c and 9d, which also have drug resistance reversing activity on taxol, vinblastine and doxorubicin in LCC6 MDR, also enhanced doxorubicin accumulation by 4.5 and 4 folds of control, respectively. In general, modulators' reversal potency of doxorubicin accumulation is closely paralleled by their potencies in reversing doxorubicin resistance in LCC6 MDR.

TABLE 1

Effects of 9d on the cytotoxicity of chemotherapeutic drugs in MDR cells.
The $IC_{50}$ value was determined for each cell line after exposure to a series of drug concentration with/without 5 µM 9d, as described in the Material and Methods.
RF represents fold-change in drug sensitivity. VP = Verapamil.

| | | Cell lines | | | | | |
| --- | --- | --- | --- | --- | --- | --- | --- |
| | | LCC6 MDR | | LCC6 | P388/ADR | | P388 |
| Agent | Treatment | $IC_{50}$ (nM) | $RF^a$ | $IC_{50}$ (nM) | $IC_{50}$ (nM) | RF | $IC_{50}$ (nM) |
| Vinblastine | Drug | 4.4 | 1 | 0.34 | 95 | 1 | 4.1 |
| | Drug + 9d | 0.42 | 10 | | 4.3 | 22 | |
| | Drug + VP | 0.29 | 15 | | N.D. | | |
| Taxol | Drug | 105 | 1 | 2.9 | 1636 | 1 | 22 |
| | Drug + 9d | 4.8 | 22 | | 30 | 55 | |
| | Drug + VP | 5.2 | 20 | | N.D. | | |
| Doxorubicin | Drug | 4690 | 1 | 300 | 1738 | 1 | 22 |
| | Drug + 9d | 550 | 9 | | 123 | 14 | |
| | Drug + VP | 300 | 16 | | N.D. | | |
| Vincristine | Drug | 26 | 1 | 0.29 | 299 | 1 | 2.2 |
| | Drug + 9d | 0.63 | 41 | | 4.5 | 66 | |
| | Drug + VP | N.D. | | | N.D. | | |
| Daunorubicin | Drug | 977 | 1 | 79 | 2111 | 1 | 25 |
| | Drug + 9d | 129 | 7.6 | | 106 | 20 | |
| | Drug + VP | $N.D.^b$ | | | 40 | 53 | |

TABLE 1-continued

Effects of 9d on the cytotoxicity of chemotherapeutic drugs in MDR cells.
The IC$_{50}$ value was determined for each cell line after exposure to a series of
drug concentration with/without 5 µM 9d, as described in the Material and Methods.
RF represents fold-change in drug sensitivity. VP = Verapamil.

| | | Cell lines | | | | | |
|---|---|---|---|---|---|---|---|
| | | LCC6 MDR | | LCC6 | P388/ADR | | P388 |
| Agent | Treatment | IC$_{50}$ (nM) | RF[a] | IC$_{50}$ (nM) | IC$_{50}$ (nM) | RF | IC$_{50}$ (nM) |
| Mitoxantrone | Drug | 1442 | 1 | 0.35 | 395 | 1 | 4.3 |
| | Drug + 9d | 646 | 2.2 | | 194 | 2 | |
| | Drug + VP | N.D. | | | N.D. | | |

[a]R.F. Relative fold = Ratio of (IC$_{50}$ without modulator) to (IC$_{50}$ with modulator). This is used as an indicator of the strength of the reversing activity of the modulator.
[b]N.D. Not done.

The dose-dependent effect of 9d on the accumulation of doxorubicin in P-gp positive and negative cells is then investigated, and is shown in FIG. 7B. It was found that 9d significantly increased doxorubicin accumulation in MDA435/LCC6 MDR cells in a dose-dependent manner, but not in sensitive MDA435/LCC6 cells. The intracellular doxorubicin concentration was gradually increased from 17% to 88% of the LCC6 when the concentration of 9d was increased from 0 to 10 µM.

Effect of Apigenin Dimers on Reversing the Anticancer Toxicity in P388/ADR Cells The above data shows that apigenin dimers, particularly 9d, are promising in reversing drug resistance in the human breast cancer cells. If these apigenin dimers can modulate MDR by inhibiting the P-gp efflux, they should be able to modulate other MDR cancers as well. To prove this, another well-characterized cancer MDR system P388/ADR-murine leukemia cell line which is resistant to ADR (adriamycin, brand name of doxorubicin) is tested. P388/ADR has been widely used as a standard for preclinical evaluation of MDR modulators.

Consistent with the previous observations, the apigenin dimers with different spacer lengths exhibited different modulatory activity in P388/ADR cells (FIGS. 8A and 9A). Again, 9d is the most potent modulator, reducing the doxorubicin and daunorubicin IC$_{50}$ by about 10 and 21 RF from 1.5 µM and 2.1 µM to 0.15 µM and 0.10 µM, respectively (FIGS. 8A and 9A). Compound 9d also showed a dose-dependent effect on reversing the resistance towards doxorubicin (FIG. 8B) and daunorubicin (FIG. 9B), with the saturating concentration at about 5 µM. Modest inhibition was noted with 9c and 9b with shorter spacer lengths, reducing the IC$_{50}$ of doxorubicin to about 3 and 2 RF and IC$_{50}$ of daunorubicin to about 4.6 and 2.5 RF, respectively. Modulators with spacers longer than 9d or shorter than 9b have little or no effect on potentiating the doxorubicin and daunorubicin cytotoxicity in P388/ADR cells. Both monomers 10a and 10b gave little modulatory activity, even when added in double the concentration used for 9c and 9d. Nevertheless, unlike MDA435/LCC6 MDR cells, the reversing activity of 9d was not as good as verapamil, which almost completely reversed the doxorubicin and daunorubicin resistance in P388/ADR cells (IC$_{50}$=0.06 µM and 0.04 µM, respectively). The above results suggest that apigenin dimers are inhibiting the P-gp in both LCC6 MDR and P388/ADR cells. The correlation between drug resistance reversing activity and the spacer length of apigenin dimers are almost identical in these two cell lines.

Compound 9d can Reverse Drug Resistance of P388/ADR Cells to Almost the Level of the Sensitive Parent Cell Line P388

Compound 9d also potentiated the action of other P-gp substrates on P388/ADR cells including doxorubicin, daunorubicin, taxol, vincristine and vinblastine to different extent (FIG. 10A to 10E). In case of taxol, vincristine and vinblastine, 5 µM of 9d completely reverse the resistance of P388/ADR to almost the sensitive level (FIGS. 10C, 10D and 10E), indicating complete inhibition of efflux of the anticancer drugs by 9d. There was no effect on mitoxantrone resistance. This suggests P388/ADR harbors an additional MDR mechanism for mitoxantrone that is insensitive to 9d. The reversing ability, as determined by the relative fold changes in IC$_{50}$ is summarized in Table 1. It varies from 14 to 66 RF.

Figure 10A:
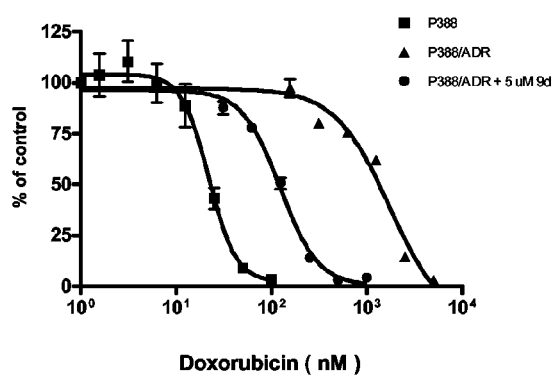
FIG. 10 shows the proliferation of P388/ADR and P388 cells in the presence of anticancer drugs (A) vinblastine, (B) taxol, (C) doxorubicin, (D) vincristine, (E) daunorubicin and (F) mitoxantrone with or without 5 μM 9d.
Figure 10B:
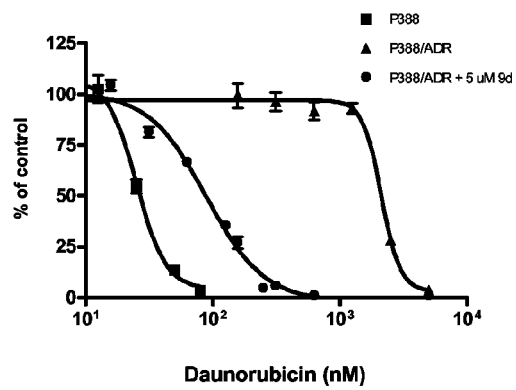
Figure 10C:
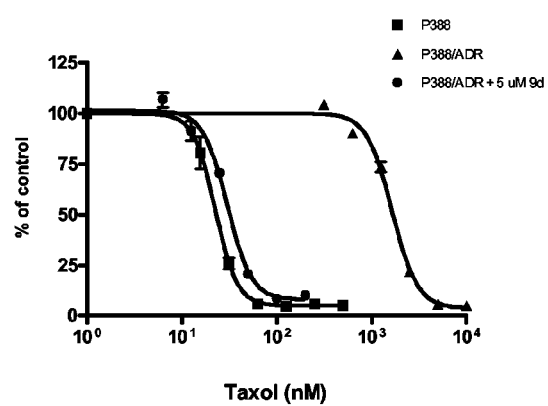
Figure 10D:
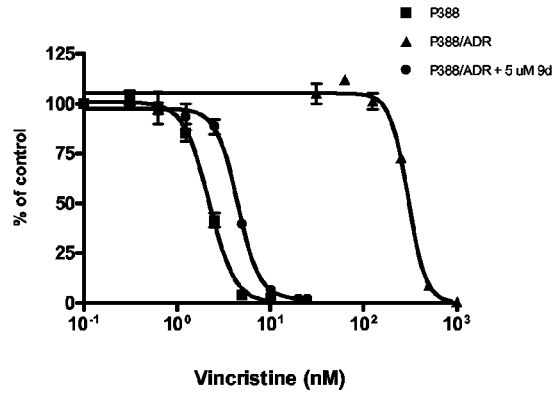
Figure 10E:
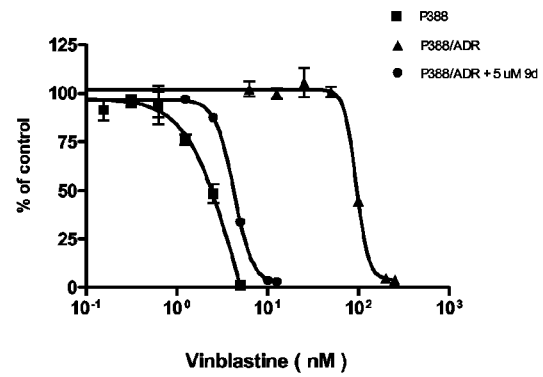
Figure 10F:
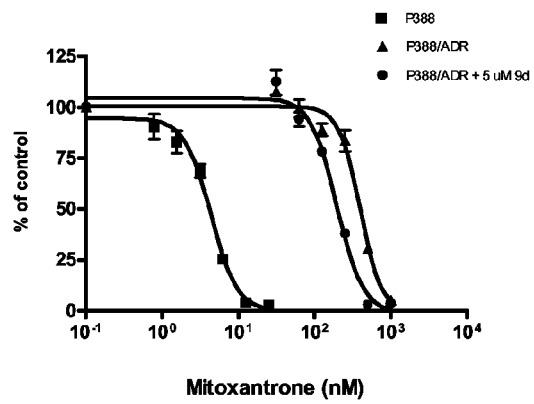

Effect of Apigenin Dimer on Cellular Accumulation of Doxorubicin in P388 and P388/ADR Cells The abilities of apigenin dimers to affect the doxorubicin accumulation in both P388 and P388/ADR cells were examined. In the DMSO treated control, accumulation of doxorubicin in P388/ADR cells was about 33% of P388 cells, indicating efflux of doxorubicin (FIG. 11A). Addition of different apigenin dimers inhibited P-gp efflux of doxorubicin in the MDR cells to different extent. Consistent with the previous results, 9d showed the highest potency causing an increase of the doxorubicin accumulation to about 2 folds of that of the control. Compounds 9b and 9c also gave comparable activity to 9d. On the other hand, the monomer 10b (with double concentration of the dimers) or other apigenin dimers with longer (9e, 9k) or shorter (9a) spacers gave little or no activity at all. The correlation between drug resistance reversing activity in P388/ADR and spacer lengths of apigenin dimers is similar to what we observed in LCC6 MDR cells. By contrast, the doxorubicin accumulation in the parent sensitive P388 cells was almost unaffected by any apigenin dimers, monomers or verapamil. When the cells were pre-incubated with various concentrations of 9d for 30 min, 9d significantly increases doxorubicin accumulation in P388/ADR cells in a dose-dependent manner, but not in sensitive P388 cells (FIG. 11B). Although 9d exhibited the best activity, it cannot restore cellular doxorubicin level in resistant P388/ADR cells to that in sensitive cells, whereas verapamil can (FIG. 11A). This suggests that 9d does not completely inhibit the P-gp efflux of doxorubicin in P388/ADR. This is consistent with its cytotoxicity modulating effect not as high as verapamil (FIG. 10A).

Effects of 9d on P-gp ATPase Activity

Figure 12:
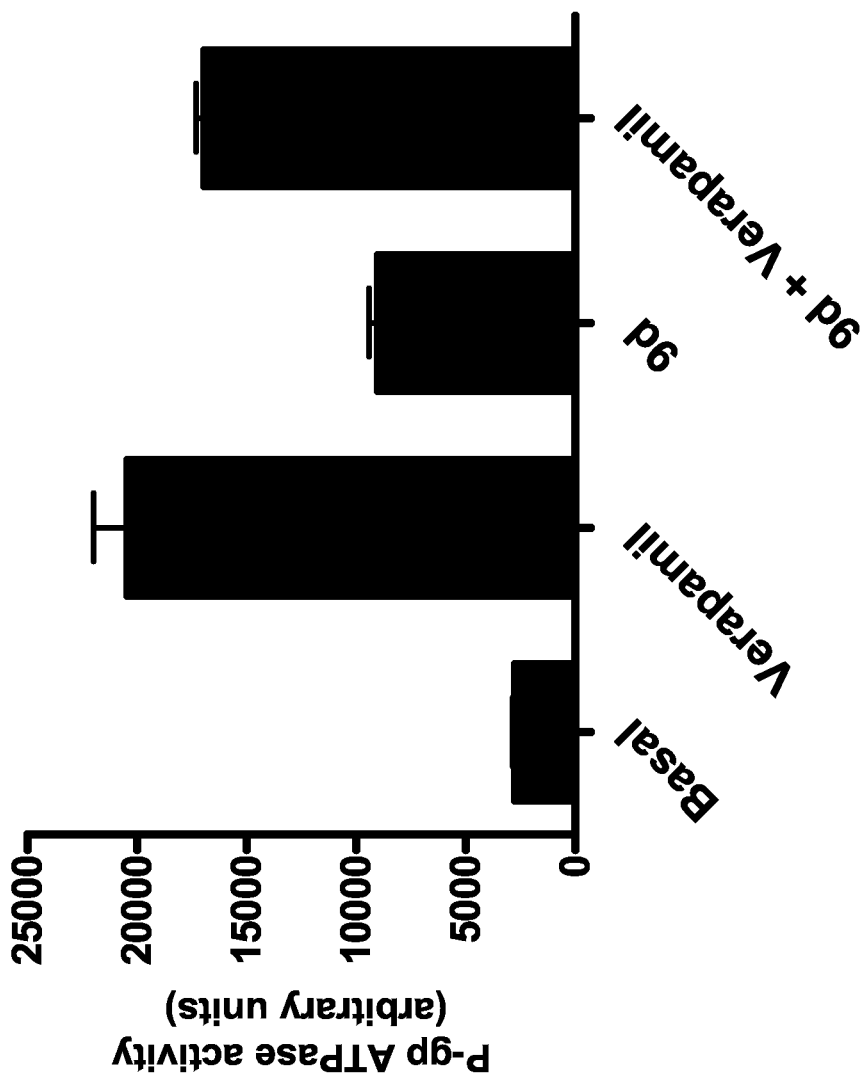
FIG. 12 shows the effects of 9d on P-gp ATPase activity.

To further investigate the interaction between 9d and P-gp, the effect of 9d (100 µM) on both P-gp ATPase activity and verapamil-induced ATPase activity has been examined. Interestingly, 9d (100 µM) can increase P-gp ATPase activity over the basal level by 3.3 fold (P<0.0001) (FIG. 12). As expected, verapamil (a well known P-gp ATPase stimulator by binding to the substrate binding site) can increase P-gp ATPase activity over the basal level by 7.4 fold (P<0.0001). Such verapamil-induced P-gp ATPase activity was lowered from 7.4 fold to 6.1 fold when 9d was also present (P<0.0001). This result suggested that 9d, like verapamil, can stimulate P-gp ATPase activity and it probably works by binding to the same site of P-gp as verapamil does. Both verapamil and 9d (100 μM) had no significant effects on non-P-gp ATPase activity (data not shown).

Biological Activities of the Polyethylene Glycol (n=4) Linked Apigenin Analog Dimers:

Since compound 9d showed good reversal activity on MDR cells, the biological activities of various apigenin analogs dimers with the same polyethyleneglycol (n=4) linker have also been examined. The $IC_{50}$ of taxol to LCC6MDR in the presence of various synthetic flavonoid analog dimers 35a-l at 5 μM concentrations have been studied and summarized in Table 2. A number of these analog dimers (35a, 35b, 35f, 35g, 35h) showed stronger reversing activity than verapamil.

In conclusion, the above results have clearly demonstrated that the flavonoid dimers linked by different spacer length are able to act as co-drugs for the chemotherapeutic treatment of cancer. An apigenin dimer with optimal spacer length is identified (9d) which displayed 6-50 RF increase of cytotoxicity of anticancer drugs in both breast and leukemia MDR cells in vitro and by dramatically enhancing their intracellular drug accumulation. Analogs of flavonoid dimers also show significant increase of cytotoxicity of anticancer drugs.

TABLE 2

Effects of analog dimers 35a to 35l on the cytotoxicity of taxol to LCC6MDR cells. The IC50 value was determined after exposure to a series of taxol concentration with 5 μM of the compound as described in the Material and Methods.
$IC_{50}$ of taxol to LCC6MDR in the presence of various synthetic flavonoid dimer analogs at 5 μM concentrations:

| Analog added | Mean $IC_{50}$ of taxol (nM) |
| --- | --- |
| None (control) | 128.2 |
| Verapamil (positive control) | 8.1 |
| 35a (all H) | 2.7 |
| 35b (7-F) | 3.1 |
| 35c (6-F) | 12.2 |
| 35d (6-Cl) | 32.8 |
| 35e (6-Br) | 20.9 |
| 35f (6,8-Di-Cl) | 3.4 |
| 35g (7-Me) | 2.4 |
| 35h (6-Me) | 3.3 |
| 35i (7-MeO) | 32.0 |
| 35j (6-MeO) | 37.7 |
| 35k (5-MeO) | 7.4 |
| 35l (6,7-Di-MeO) | 16.4 |

Reduction of Drug Resistance in Treating Parasitic Diseases by Flavonoid Dimers

Cell lines and Cell Culture. Promastigotes of *Leishmania enriettii* (LePentR50, Le wild type, LeMDR1 −/− and LeMDR1-overexpressed LeV160 mutants) and *Leishmania donovani* (LdAG83, Ld2001 and Ld39) were employed in this study. The former is a natural infective strain of guinea pig and the latter is a clinical strain, which may cause visceral leishmaniasis in human. Both strains were cultured in Schneider's *Drosophila* Medium (Invitrogen), pH 6.9 supplemented with 10% (v/v) heat inactivated fetal calf serum (Hyclone) with 4 mM glutamine (Sigma) and 25 μg/mL gentamicin solution (Invitrogen), at 27° C. for 4 days (Cloning and functional analysis of an extrachromosomally amplified multidrug resistance-like gene in *Leishmania enriettii*. Mol. Biochem. Parasitol 1993, 60, 195-208).

Promastigotes of LePentR50 (pentamidine-resistant, $IC_{50}$ of pentamidine=117 μg/mL), Ld2001 (sodium stibogluconate resistant, $IC_{50}$ of SSG=4.1 mg/mL) and Ld39 (sodium stibogluconate resistant, $IC_{50}$ of SSG=6.4 mg/mL) were cultured in the presence of 50 μg/mL pentamidine (Sigma) and 3.5 mg/mL sodium stibogluconate (SSG), respectively. No sodium stibogluconate was added to the *L. donovani* wild type (LdAG83, $IC_{50}$ of SSG=1.5 mg/mL). Promastigotes of LeV160 were culture in the presence of 160 μg/mL vinblastine. No pentamidine and vinblastine (Sigma) was added to the Le wild type and LeMDR1 −/− mutant.

Amastigotes of *L. donovani* was prepared by spinning down 50 mL 4-day-old promastigotes (late log phase), and transferred to an axenic medium containing M199 Medium (Gibco), 0.5% Trypto casein soya, 3 mM L-cysteine, 15 mM D-glucose, 5 mM L-glutamine, 4 mM NaHCO3, 25 mM HEPES, 0.01 mM bathocuproine-disulfonic acid and 0.023 mM Hemin. Cells were then incubated at 37° C. for 24 hr. Amastigotes became ovoid in shape and were ready for drug accumulation assay.

Cell Viability Assay

The viability of promastigotes was determined by the Cell Titer 96® Aqueous Assay (Promega) that employs a tetrazolium compound (MTS) and electron coupling reagent, phenazine methosulfate (PMS). Promastigotes were seeded into 96-well flat bottom microtiter plate at $1 \times 10^5$ cells per well in a final volume of 100 μL medium. To determine the cytotoxic effects of flavonoid dimers to the parasites, various concentrations of flavonoid dimers were added to the promastigotes. To determine the reversal effects of flavonoid dimers with different spacer lengths, various concentrations of antileishmanial drugs, one of pentamidine or SSG, vinblastine and puromycin was added to the wells with or without flavonoid dimers. The parasites were incubated at 27° C. for 72 hrs. Each concentration of antileishmanials with or without the flavonoid dimers was tested in triplicates in each experiment. A 2 mg/mL MTS and 0.92 mg/mL PMS were mixed at a ratio of 20:1 (MTS: PMS). After 72-hr incubation, 10 μL of MTS: PMS mixture was added into each well of microtiter plate. The plate was then incubated at 27° C. for 4 hrs for color development. After 4 hrs of incubation, the OD values were determined at 490 nm using automatic microtiter plate reader (Bio-Rad). The results were presented as % of survivors (OD value of each well with test compound is divided by untreated control well).

Pentamidine Accumulation Assay by HPLC

The effect of flavonoid dimers on accumulation of pentamidine was investigated. One mL of 4-day-old promastigotes (late log phase with a cell density of about $2 \times 10^8$ cells/mL) was incubated with 0.84 mM pentamidine and various concentrations of flavonoid dimer (9d) including 0, 15, 30 and 60 μM at 27° C. for 3 hr at dark. Each concentration of 9d was tested in triplicates, and repeated twice times in separate experiments. After 3 hrs of incubation, the parasites were washed three times with cold PBS, pH 7.4. The cell pellet was then dissolved in 350 μL 75% acetonitrile and lysed by repeated freeze-thaw cycles. After lysing, the lysed cell suspension was centrifuged at 14,000 g at 4° C. for 10 min. The supernatant was collected and ready for determining pentamidine concentration using HPLC (Agilent 1100 Series). The pentamidine pools were analyzed on Zorbax ODS C18 column (4.6 mm×25 cm, 5-micron) kept at 40° C. The mobile phase consisted of water (10 mM tetramethylammonium chloride (TMAC), 10 mM sodium heptanesulphonate (SHS), 4.2 mM phosphoric acid (PA)) for pump A and 75% acetonitrile (ACN) in water (10 mM TMAC, 10 mM SHS, 4.2 mM PA) for pump B. The column was equilibrated at 40° C. overnight before analyses. Using a flow rate of 1.0 mL/min and signal at 265 nm, analyses were made at 58% pump A and 42% pump B. The retention time of pentamidine is 3.2 min. Compound 9d would not be eluted out under these conditions. To generate a standard curve, a 200 μM stock solution of pentamidine isethionate salt were prepared by dissolving 2.5 mg pentamidine isethionate salt in 21 mL 75% ACN (10 mM TMAC, 10 mM SHS, 4.2 mM PA). Concentration of 100, 50, 25 and 13 μM were then made by serial dilution, allowing the generation of standard curve.

Total Antimony [Sb(III) and Sb(V)] Accumulation Assay Using ICP-MS

The effect of flavonoid dimers on accumulation of antimony sodium stibogluconate (SSG) was investigated. Amastigotes are more susceptible to SSG and therefore accumulate more SSG as compared to promastigotes. Therefore, amastigotes were chosen for studying the Sb accumulation assay. One mL of 4-day-old amastigotes ($2 \times 10^8$ cells/mL) was incubated with 0.05 mM SSG and different concentrations of flavonoid dimer (9d) including 0, 30 and 60 μM at 37° C. for 3 hr. Each concentration of 9d was tested in triplicates, and repeated twice times in separate experiments. After 3 hour incubation, the parasites were washed thrice with cold PBS, pH 7.4. The cell pellet was dissolved in 200 μL concentrated nitric acid for 24 hr at room temperature. The sample was diluted to 3 mL with distilled water, resulting in a final concentration of about 5 ppb of total Sb solution. It was then injected to ICP-MS (Perkin-Elmer) for quantitation. Antimony was measured at its m/z ratios of 121 and 123 with indium (In, m/z=115) as an internal standard. All chemicals used for the pretreatment of the samples were of at least analytical grade and the distilled water used directly as received without further purification.

Results

Pentamidine-Resistant *L. enriettii* (LePentR50) and SSG-Resistant *L. donovani* (Ld39 and Ld2001)

Figure 13A:
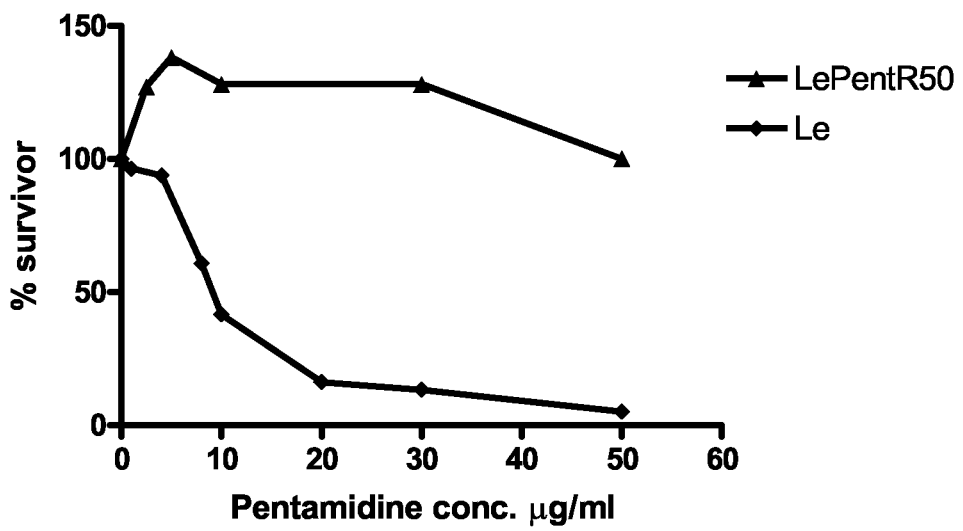
FIG. 13 shows the drug resistance of *Leishmania*: (A) pentamidine-resistant *L. enriettii* (LePentR50) and (B) sodium stibogluconate (SSG)-resistant *L. donovani* (Ld39 and Ld2001)
Figure 13B:
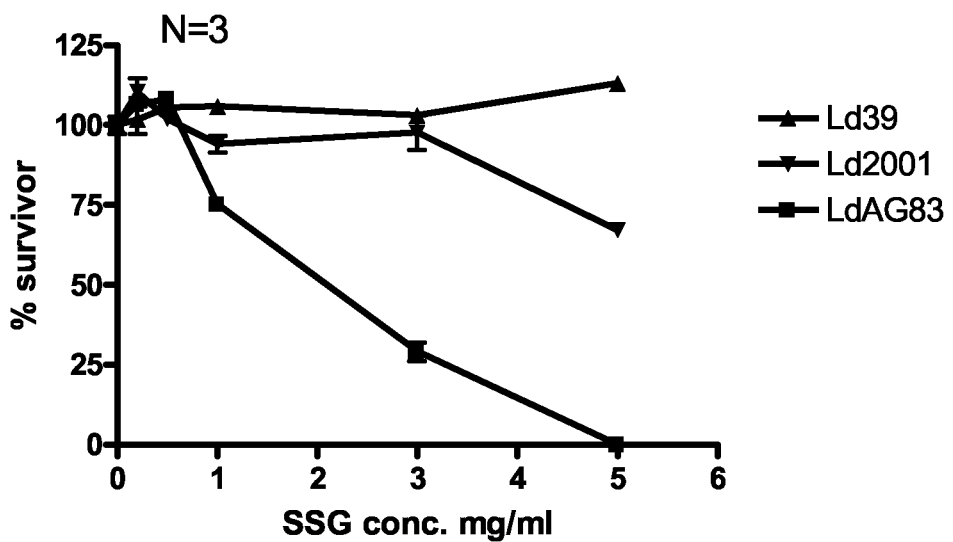

Three drug-resistant *Leishmania* cell lines, namely LePentR50 (pentamidine resistant *L. enriettii*), Ld39 and Ld2001 (SSG resistant *L. donovani*), have been used to study the drug resistance-modulating activity of the synthetic flavonoid dimers of this invention. LePentR50 is a pentamidine-resistant *L. enriettii* cell line obtained by step-wise selection in our laboratory (unpublished). It is maintained in the presence of 50 μg/ml pentamidine and has an $IC_{50}$ of about 117 μg/ml whereas the wild type *L. enriettii* (Le) has an $IC_{50}$ of about 8.7 μg/ml (FIG. 13A). Ld39 and Ld2001 are two *L. donovani* cell lines that are resistant to pentavalent antimonials sodium stibogluconate (SSG) (2). Ld39 and Ld2001 are maintained in the presence of 3.5 mg/ml SSG and have an $IC_{50}$ of 6.1 and 4.1 mg/ml respectively whereas the wild type *L. donovani* (LdAG83) has an $IC_{50}$ of about 2.4 mg/ml (FIG. 13B).

In Vitro Cytotoxicity of Synthetic Flavonoid Dimers to *Leishmania* Parasites

The cytotoxicity of the flavonoid dimers of this invention in each *Leishmania* cell line was measured by the MTS-based cell proliferation method. Table 3 summarizes the $IC_{50}$ value of each synthetic modulator to LePentR50, LdAG83 and L39. Pentamidine resistant LePentR50 were relatively resistant to some of the flavonoid dimers (9a to 9f, 10a and 10b), with $IC_{50}$ ranging from 40 μM to greater than 200 μM. The sensitivity of *L. donovani*, LdAG83 and Ld39, to synthetic flavonoid dimers was comparable to the *L. enriettii* except for 9c and 9d. It was found that both LdAG83 ($IC_{50}$ of 9c=8±0.3 μM and $IC_{50}$ of 9d=7±0.4 μM) and Ld39 ($IC_{50}$ of 9c=11±0.7 μM and $IC_{50}$ of 9d=10±0.9 μM) were more susceptible to 9c and 9d than LePentR50. The species difference between *L. enriettii* and *L. donovani* was limited to the apigenin dimers 9c and 9d only. These two species were equally sensitive to apigenin monomer and apigenin with 3 (10a) or 4 (10b) ethylene glycol units (Table 3). The hypersensitivity of *L. donovani*, both LdAG83 and Ld39, to 9c and 9d may mean that these two apigenin dimers may be useful as an anti *L. donovani* agent.

TABLE 3

The hypersensitivity of *L. donovani*, both LdAG83 and Ld39, to 9c and 9d may mean that these two apigenin dimers may be useful as an anti *L. donovani* agent.
Table 3. $IC_{50}$ of synthetic flavonoids for *Leishmania* parasites

| | $IC_{50}$(μM) | | |
|---|---|---|---|
| | LePentR50 | LdAG83 | Ld39 |
| 9a | >200[a] | 95 ± 3.2 | 117 ± 10 |
| 9b | >200[a] | >200[a] | >200[a] |
| 9c | >200[a] | 8 ± 0.3 | 11 ± 0.7 |
| 9d | >200[a] | 7 ± 0.4 | 10 ± 0.9 |
| 9e | 70 ± 3.0 | 30 ± 1.2 | 42 ± 2.3 |
| 9f | 40 ± 5.3 | 11 ± 2.0 | 13 ± 0.6 |
| 9h-1 | ND | 12 ± 0.2 | 14 ± 0.1 |
| 9i | ND | 10 ± 0.3 | 14 ± 0.1 |
| 9j | ND | >200[a] | >200[a] |
| 9k-1 | ND | 50 ± 7 | 60 ± 3 |
| 10a | >200[a] | >200[a] | >200[a] |
| 10b | >200[a] | >200[a] | >200[a] |
| Apigenin | 55 ± 2.6 | 32 ± 4.1 | 43 ± 5.9 |

The $IC_{50}$ values of each synthetic flavone were determined by MTS-based proliferation assay. Each $IC_{50}$ value was derived from at least two independent experiments with triplicates in each experiment.
[a]$IC_{50}$ values cannot be determined because these modulators did not have any cytotoxic effect at the highest concentration tested (200 μM).
ND: $IC_{50}$ values were not determined for these modulators but no cytotoxic effect was observed at 12 μM, which was twice the concentration used to study drug resistance modulating activity.

Effect of Synthetic Flavonoid Dimers on Modulating Pentamidine Resistance of LePentR50

Figure 14A:
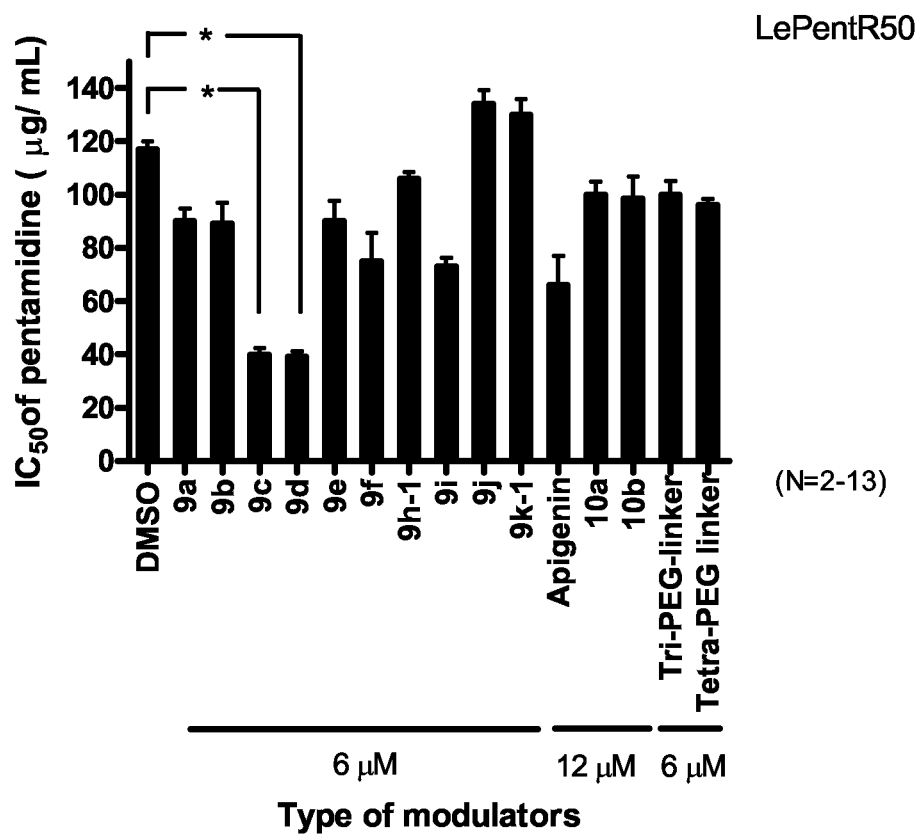
FIG. 14 shows the modulating activity of the flavonoid dimers of this invention with different length of ethyleneglycol units (from one to thirteen units) on the resistance of pentamidine-resistant *L. enriettii* LePentR50 (A), SSG resistance of SSG-resistant *L. donovani* Ld39 and Ld2001 (B and C) and wild-type *L. donovani* LdAG83 (D)

DMSO-treated LePentR50 has an $IC_{50}$ of pentamidine of about 117.0±3.0 μg/ml (FIG. 14A). 6 μM of compound 9c (n=3) ($IC_{50}$=40.0±2.7 μg/mL, P<0.01) and 9d (n=4) ($IC_{50}$=39.2±2.1 μg/mL, P<0.01) significantly reduced the $IC_{50}$ of LePentR50 by about 3 folds (FIG. 14A). Other flavonoid dimers with either shorter linker lengths (9a ($IC_{50}$=90±4.88 μg/mL) and 9b ($IC_{50}$=89.2±8.92 μg/mL)) or longer linker lengths (9e ($IC_{50}$=90±7.88 μg/mL), 9f ($IC_{50}$=75±10.99 μg/mL), 9h-1 ($IC_{50}$=106±2.7 μg/mL), 9i ($IC_{50}$=73±3.54 μg/mL), 9j ($IC_{50}$=134±5.4 μg/mL) and 9k-1 ($IC_{50}$=130±6.1 μg/mL)) gave less than half or no modulating activity (FIG. 14A). The "U" shaped relationship between the linker length and modulating activity of the flavonoid dimers may suggest that the targets of the apigenin moiety are separated by a relatively defined distance. The control compounds of apigenin monomer with three or four ethylene glycol units (10a and 10b) did not give any modulating activity even when used at double the concentration (12 μM) (FIG. 14A; $IC_{50}$=100.0±5.0 μg/ml and 98.5±8.5 μg/ml respectively). This may show that the modulating activity of 9c and 9d is indeed due to their dimeric nature. Simple molar increase in the number of apigenin moiety did not result in any significant modulating activity. As a control, the linkers with n=3 and 4 (Tri-PEG-linker and tetra-PEG linker) did not have any reversing effect (FIG. 14A).

Effect of Synthetic Flavonoid Dimers on Modulating SSG Resistance of Ld39 and Ld2001

Figure 14B:
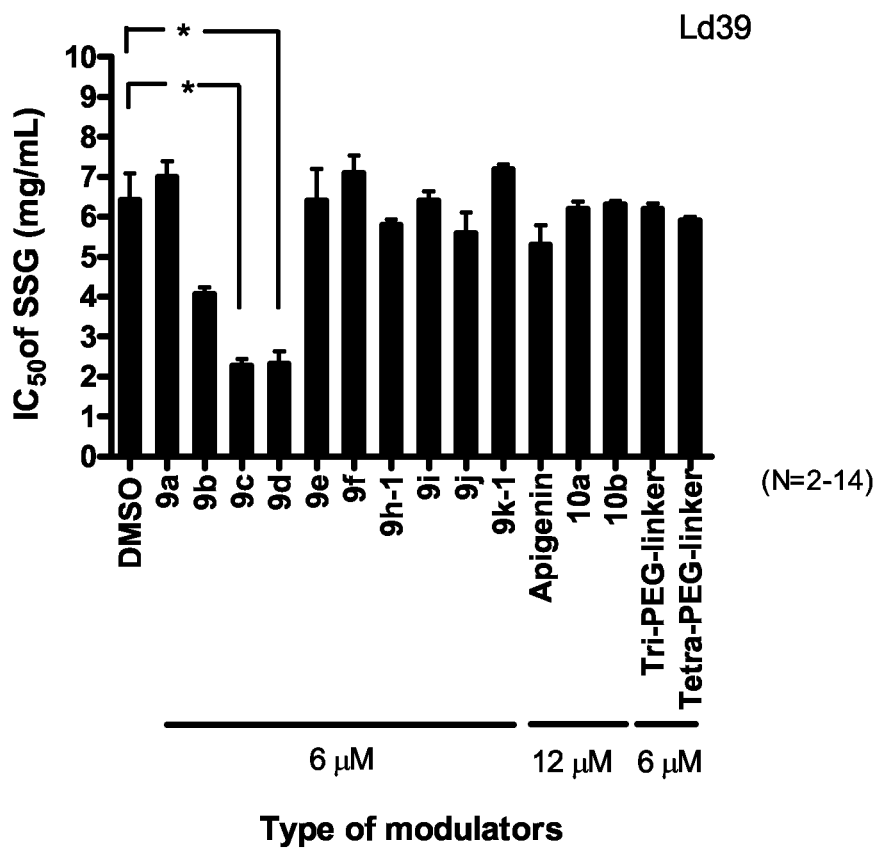
Figure 14C:
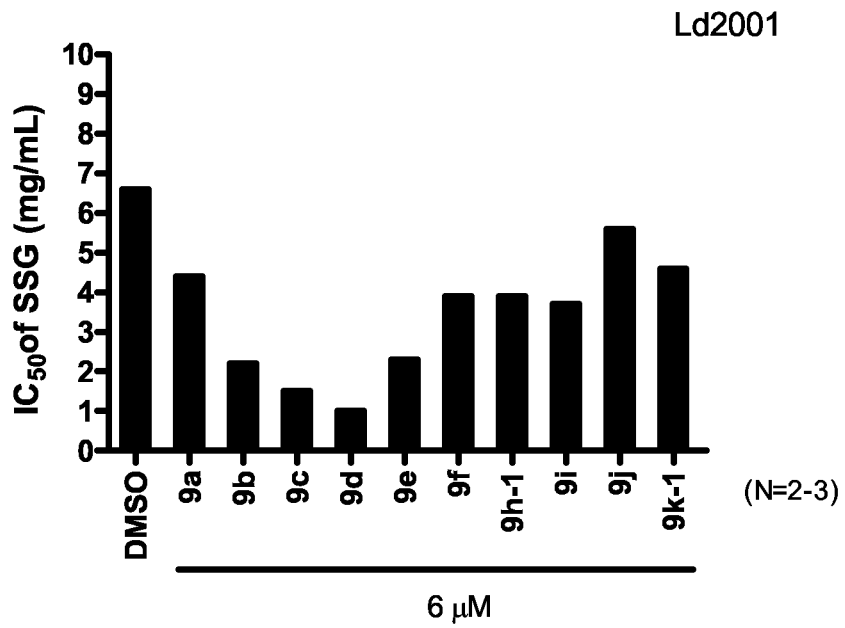
Figure 14D:
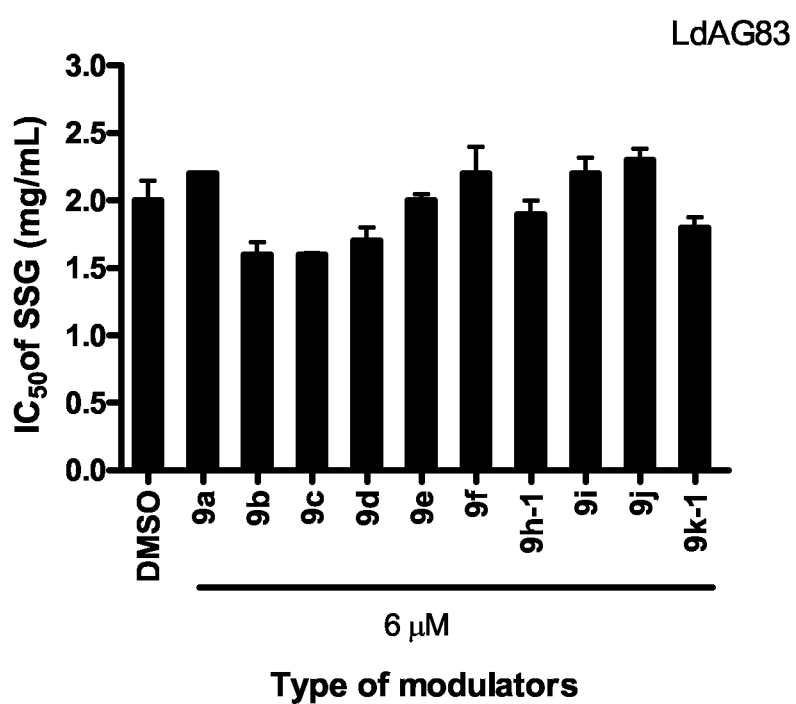
Figure 15A:
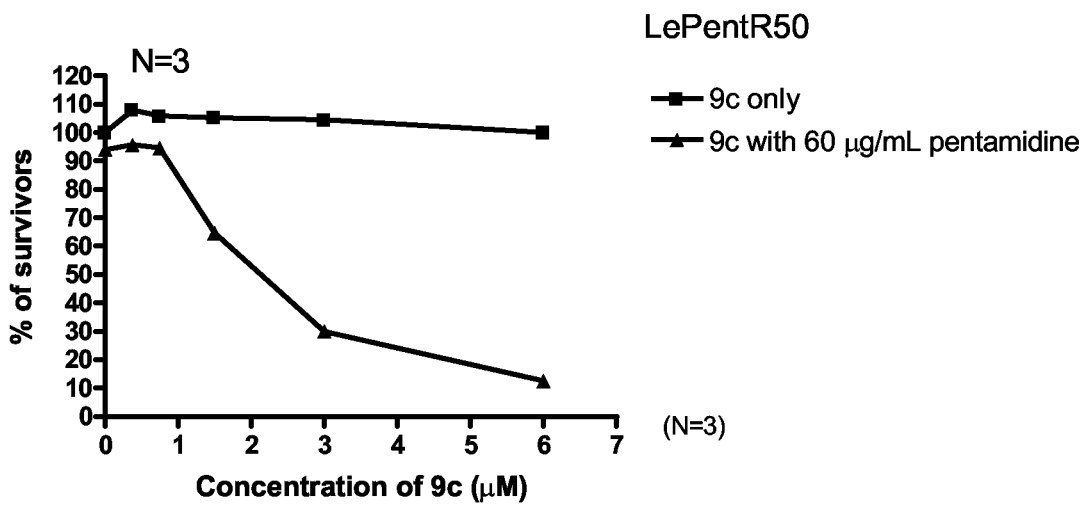
FIG. 15 shows the dose-dependent modulating activity of flavonoid dimers 9c and 9d on the pentamidine resistance of LePentR50.
Figure 15B:
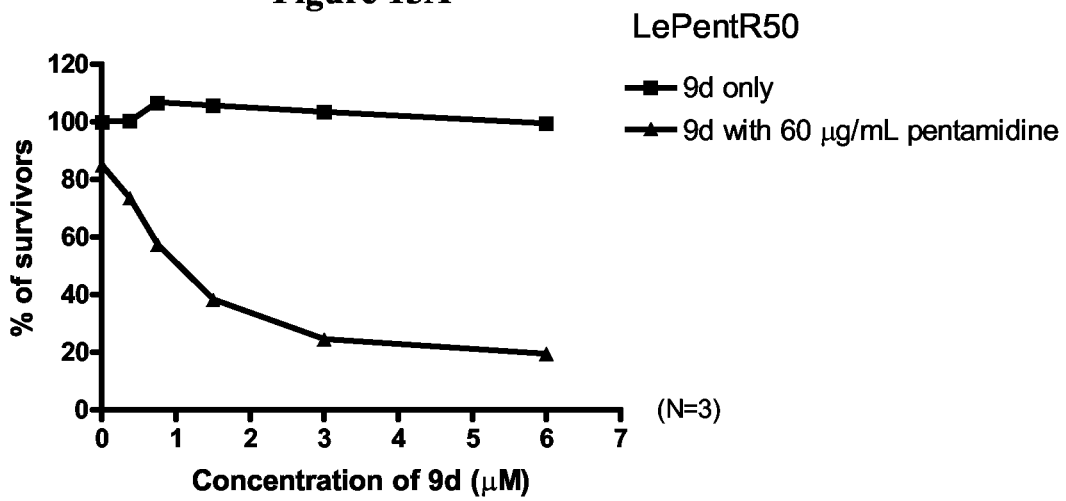
Figure 16:
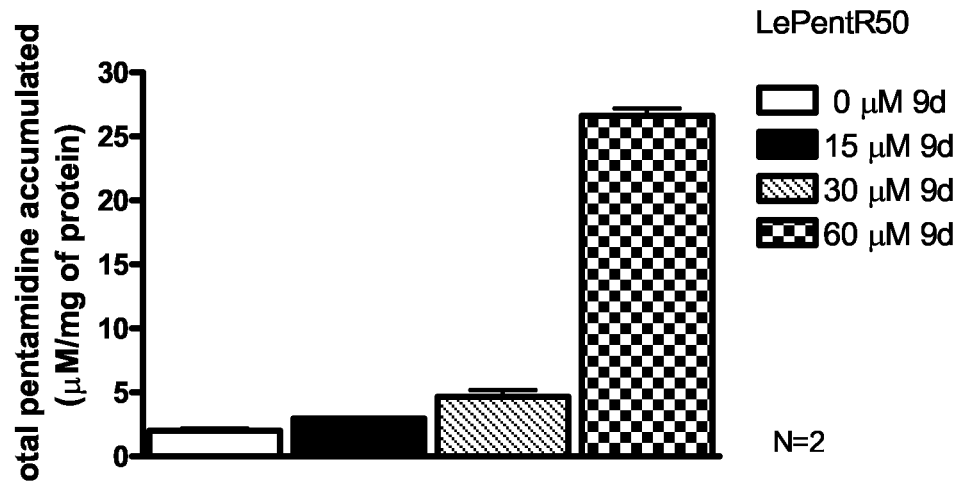
FIG. 16 shows the effect of flavonoid dimer 9d on pentamidine accumulation of LePentR50.
Figure 17A:
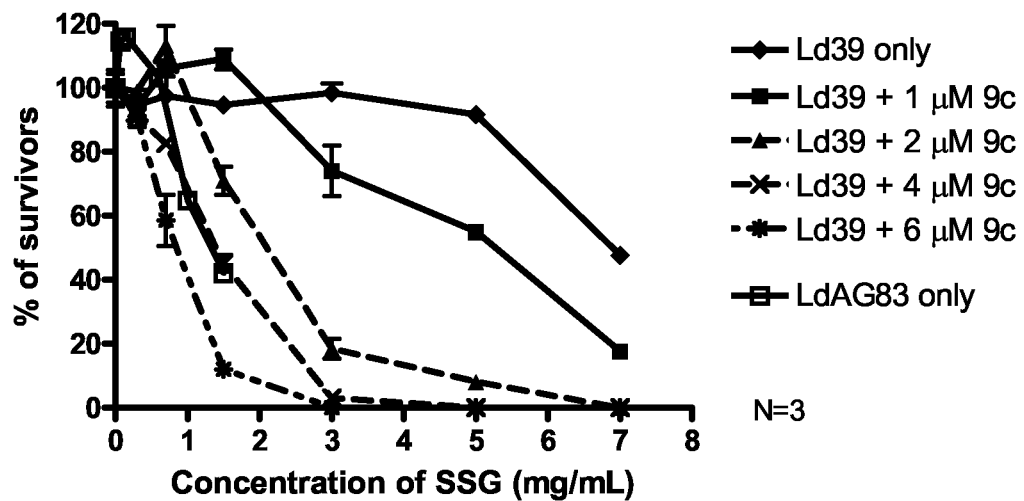
FIG. 17 shows the dose-dependent modulating activity of 9c (A) and 9d (B) on the SSG resistance of Ld39, 9d on LdAG83 (C) and the effect of 9d on the total antimony accumulation in LdAG83 and Ld2001 (D)
Figure 17B:
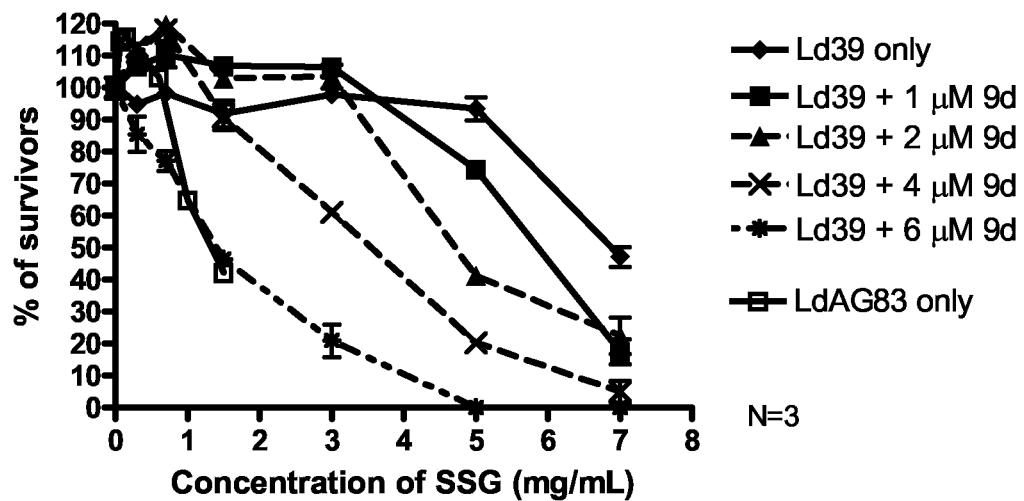
Figure 17C:
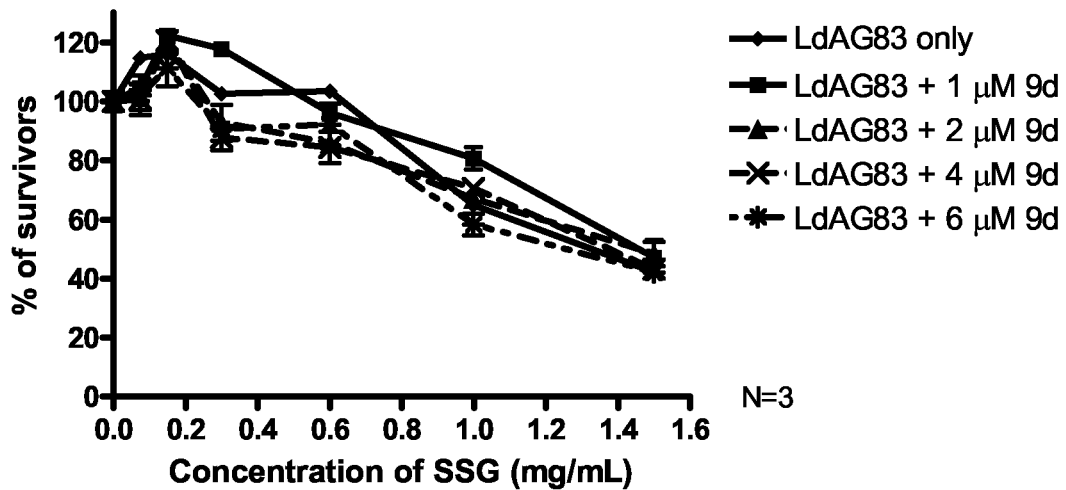
Figure 17D:
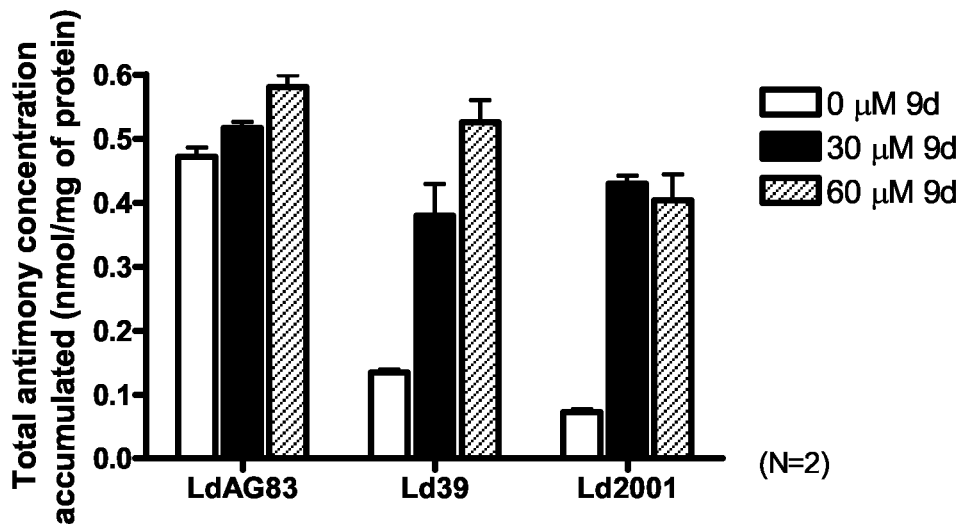
Figure 18A:
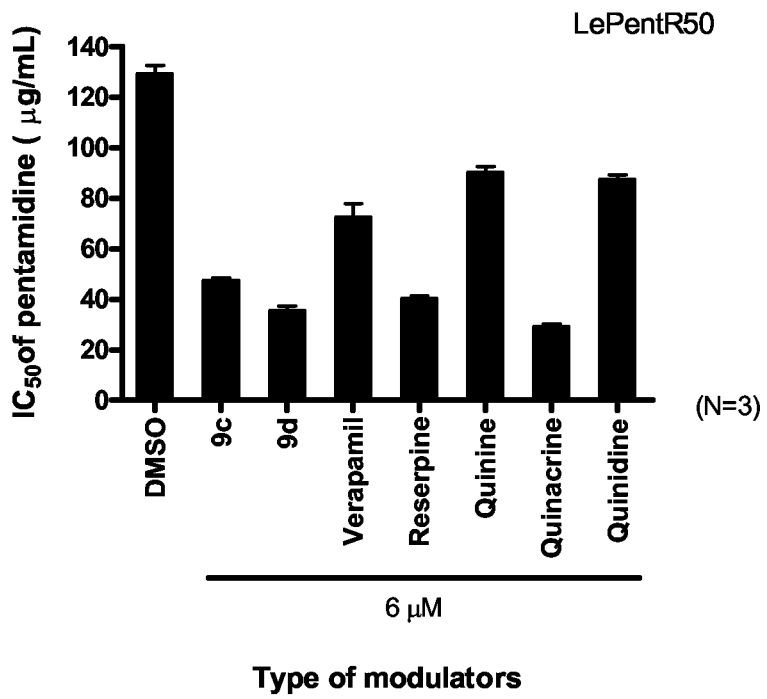
FIG. 18 shows the comparison of the modulating activity of 9c and 9d with other MDR modulators on the pentamidine resistance of LePentR50 (A) and SSG resistance of Ld39 (B).
Figure 18B:
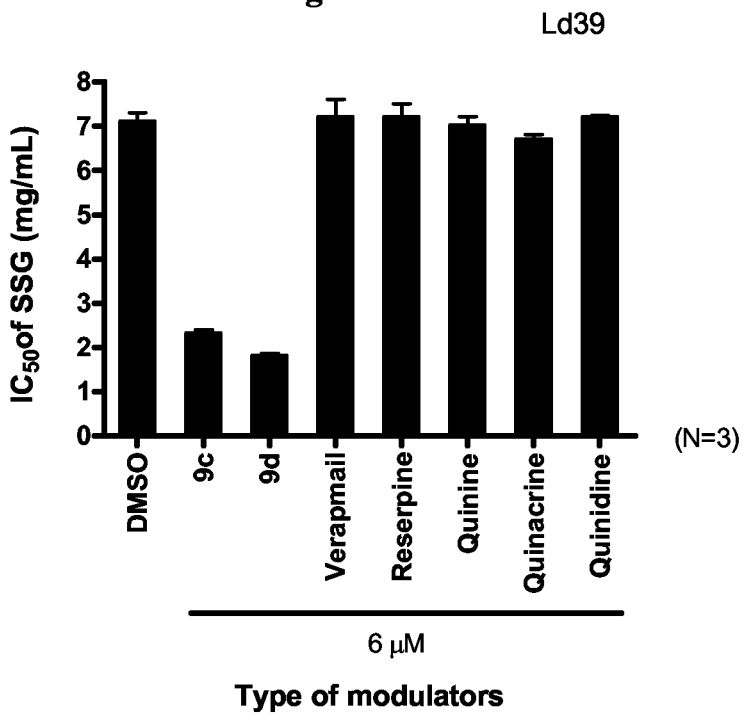

The effect of the flavonoid dimers of this invention on modulating SSG resistance of Ld39 and Ld2001 promastigotes has also been investigated. Among the flavonoid dimers (used at 6 μM), 9c and 9d were the most effective in modulating the SSG resistance of *L. donovani* Ld39 promastigotes. The $IC_{50}$ of SSG of Ld39 was reduced from 6.4±0.7 mg/ml (DMSO treated) to 2.3±0.2 mg/ml (9c treated) and 2.3±0.3 mg/ml (9d treated) (FIG. 14B). Similar to the pentamidine resistance in LePentR50, compounds with shorter linkers (9a and 9b) or longer linkers 9e to 9j) did not show substantial SSG resistance modulating activity (FIG. 14B). Apigenin, 10a and 10b, even when used at 12 μM, did not give any significant modulating activity either (FIG. 14B). The control linkers with n=3 (Tri-PEG-linker) or n=4 (Tetra-PEG-linker) did not give effect either (FIG. 14B).

Essentially a similar pattern was observed when the other SSG-resistant *L. donovani* Ld2001 was studied (FIG. 14C). Compounds 9c and 9d were the most effective and can decrease the $IC_{50}$ of SSG of Ld2001 from 6.6 mg/ml (DMSO control) to 1.5 mg/ml (9c) and 1.0 mg/ml (9d) respectively (FIG. 14C).

However, all synthetic flavonoid modulators including 9c and 9d had no modulatory effect on SSG-sensitive wild type *L. donovani* LdAG83. $IC_{50}$ values remained almost the same with or without any modulators (FIG. 14D). This may suggest that 9c and 9d specifically target a protein that is uniquely or sufficiently present in SSG-resistant parasite but absent or rarely expressed in SSG-sensitive parasite.

Synthetic Flavonoid Dimers 9c and 9d Show a Dose-Dependent Modulating Activity on Pentamidine Resistance and Accumulation in LePentR50

The dosage effect of the two most effective modulators according to the results above, namely 9c (containing 3 ethylene glycol units) and 9d (containing 4 ethylene glycol units) on modulating pentamidine resistance of LePentR50. When treated with 60 μg/ml pentamidine alone, the survival of LePentR50 was only slightly decreased (94.0±2.3% of untreated). Co-treatment of 60 μg/ml pentamidine with increasing concentrations of 9c, however, resulted in a gradual decrease in the survival of LePentR50, suggesting that 9c can modulate the pentamidine resistance of LePentR50 in a dose-dependent manner (FIG. 15A). The $EC_{50}$ for 9c (the effective concentration of 9c that results in 50% survival of LePentR50 at 60 μg/ml pentamidine) is about 1.85 μM. Similar observation was made for compound 9d (FIG. 15B). No toxicity was observed for 9d up to the concentration of 6 μM. The $EC_{50}$ for 9d is about 0.94 μM. Compound 9d is therefore about twice as effective as 9c in modulating the pentamidine resistance of LePentR50.

The effect of 9d on the pentamidine accumulation of LePentR50 has also been studied. Higher concentrations of 9d (15, 30 and 60 μM), together with a shorter incubation time (3 hours) is used to measure the pentamidine accumulation. Compound 9d can increase the pentamidine accumulation of LePentR50 in a dose-dependent manner (FIG. 16). The intracellular pentamidine concentration of LePentR50 was gradually increased from 2.0±0.2 to 2.95±0.01, 4.69±0.51 and 26.6±0.6 μM pentamidine/mg protein when the concentration of 9d was increased from 0 to 15, 30 and 60 μM respectively (FIG. 16). This shows that 9d is modulating the pentamidine resistance of LePentR40 by increasing the pentamidine accumulation. Incubation of LePentR50 with 60 μM of 9d for 3 hours did not result in any cytotoxicity (data not shown). Therefore, the dose-dependent increase in pentamidine accumulation is believed to be due to the modulatory effect of 9d, but not due to its cytotoxic effect on LePentR50.

Synthetic Flavonoid Dimers 9c and 9d Show a Dose-Dependent Modulating Activity on SSG Resistance and Accumulation in Ld39 Cells Similar to LePentR50, both 9c and 9d showed a dose-dependent modulating effect on the SSG resistance of Ld39 promastigotes (FIGS. 17A and 17B). 4 μM of 9c or 9d can reduce the SSG resistance level of Ld39 back to the level of the sensitive strain of LdAG83 (FIGS. 17A and 17B). The modulating effect of 9d is believed to be specific to a target protein present only on Ld39 because 9d did not have any modulating effect on the SSG sensitivity of LdAG83 even when used up to 6 μM (FIG. 17C).

The effect of 9d on the SSG accumulation of *L. donovani* amastigotes has been investigated. Axenic amastigotes were produced by adapting the parasites to 37° C. for 24 hours. Light microscopy showed that the cells have rounded up (data not shown).

In the SSG accumulation experiment, higher concentrations of 9d (30 and 60 μM) have been used, together with a shorter incubation time (3 hours) to measure the SSG accumulation. In the absence of 9d, the accumulation of SSG of Ld39 and Ld2001 was 28% and 15% of that of LdAG83 respectively (FIG. 17D). When treated with 30 μM 9d, the SSG accumulation of Ld39 and Ld2001 was increased to 74% and 83% of that of LdAG83 respectively (FIG. 17D). When the concentration of 9d was further increased to 60 μM, the SSG accumulation of Ld39 and Ld2001 was 90% and 69% of that of LdAG83 respectively (FIG. 17D). By contrast, accumulation of SSG in SSG-sensitive LdAG83 treated with 9d (30 μM or 60 μM) did not significantly differ from its accumulation in cells without any treatment, indicating that the dimer 9d may appear to specifically inhibit the function of the ABC transporters present only in SSG-resistant strain (FIG. 17D). Compound 9d did not have any cytotoxicity to *L. donovani* at 60 μM when treated for 3 hours (data not shown), confirming that the increase in SSG accumulation was due to the modulating effect of 9d, and not due to its cytotoxic effect.

Comparison of the Modulating Activity of 9c and 9d with Other Traditional MDR Modulators The modulating activity of 9c and 9d with verapamil, reserpine, quinine, quinacrine and quinidine has been compared. For LePentR50, the modulating activity of modulators of 9c ($IC_{50}$=47±1.2 μg/mL) and 9d ($IC_{50}$=35±2.3 μg/mL) was similar to that of reserpine ($IC_{50}$=40±1.3 μg/mL) and quinacrine ($IC_{50}$=28.7±1.3 μg/mL), with about 2.7-, 3.7-, 3.2- and 4.5-fold pentamidine sensitization, respectively (FIG. 18A). In contrast, only less than half-fold sensitization was demonstrated when using verapamil, quinine and quinidine (FIG. 18A). Regarding the modulating activity of SSG resistance in Ld39, only 9c and 9d were effective ($IC_{50}$=2.3±0.1 mg/mL and 1.8±0.05 mg/mL respectively), representing 3.1- and 3.9-fold SSG sensitization (FIG. 18B). None of the other traditional MDR chemosensitizers exhibited any modulating effect ($IC_{50}$=7.2±0.54, 7.2±0.3, 7.0±0.21, 6.7±0.11 and 7.2±0.04 mg/mL for verapamil, reserpine, quinine, quinacrine and quinidine, respectively) (FIG. 18B).

The Target of the Flavonoid Dimers of this Invention is not LeMDR1

It is possible that the flavonoid dimers of this invention would also bind to the ABC transporters via the two NBDs. The possibility of whether the ABC transporter, LeMDR1, in *L. enriettii* is the target of the synthetic flavonoid dimers or not has been investigated by studying the modulating effect of the synthetic flavonoid dimers on three *L. enriettii* cell lines, namely wild type Le, LeMDR1 knockout (LeMDR1 −/−) and LeMDR1 overexpressed (LeV160). It was found that pentamidine resistance was inversely related to the copy number of LeMDR1. The IC$_{50}$ of pentamidine of LeMDR1 −/−, Le and LeV160 are 18.9±0.8, 12.0±0.8 and 9.0±0.1 μg/ml, respectively (Table 4). When the panel of synthetic flavonoid dimers was tested for their modulating activity on the pentamidine resistance of LeMDR1 −/−, it was found that 9c and 9d were effective in reducing the IC$_{50}$ of pentamidine to 5±0.3 μg/mL and 4.6±0.4 μg/mL respectively, representing 3.8-fold and 4.1-fold sensitization (Table 4). Compounds 9b (IC$_{50}$=9.4±0.4 μg/mL) and 9h-1 (IC$_{50}$=8.2±0.5 μg/mL) showed a 2.0- and 2.3-fold sensitization, respectively. However, 9a (IC$_{50}$=18±1.0 μg/mL), 9e (IC$_{50}$=12.5±0.1 μg/mL), 9f (IC$_{50}$=12.5±0.8 μg/mL), 9i (IC$_{50}$=13.8±0.7 μg/mL), 9j (IC$_{50}$=20.9±1.3 μg/mL) and 9k-1 (IC$_{50}$=20.9±3 μg/mL) gave less than half or little sensitization effect (Table 4). When all the flavonoid dimers were analyzed, a "U" shaped relationship was found between the ethylene glycol linker length and the pentamidine resistance modulating activity. This is similar to what we found in LePentR50 (FIG. 14A).

In Le wild type cells, 9d (IC$_{50}$=4±0.3 μg/mL) significantly reduced the IC$_{50}$ of pentamidine from 12.0±0.8 μg/mL to 4.0±0.8 μg/mL (about 3-fold decrease) (Table 4). In LeMDR1-overexpressed LeV160, 9c (IC$_{50}$=5.0±0.4 μg/mL) and 9d (IC$_{50}$=4.7±0.1 μg/mL) slightly decreased the IC$_{50}$ of pentamidine from 9.0±0.1 μg/mL to 5.0±0.4 and 4.7±0.1 μg/mL respectively (about 1.8-fold and 1.9-fold decrease) (Table 4). Compounds 9e (IC$_{50}$=7.5±0.3 μg/mL), 9f (IC$_{50}$=7.2±0.3 μg/mL) and 9l (IC$_{50}$=6.8±0.2 μg/mL), however, gave no sensitization effect.

The observation that the flavonoid dimers of this invention can modulate the pentamidine resistance irrespective of the copy number of LeMDR1 suggests that LeMDR1 is not the target for the synthetic flavonoid dimers, which was known to be responsible for vinblastine and puromycin resistance in *L. enriettii* (Sequence requirements of the ATP-binding site within the C-terminal nucleotide-binding domain of mouse P-glycoprotein: structure-activity relationships for flavonoid binding. *Biochemistry* 2001, 40, 10382-91). It was found that none of the flavonoid dimers have any significant modulating activity (Table 4), further suggesting that the synthetic flavonoid dimers are not targeting LeMDR1.

Discussion

Various ABC transporters in *Leishmania* have been implicated in mediating drug resistance (Chemosensitizers in drug transport mechanisms involved in protozoan resistance. *Curr. Drug Targets Infect Disord* 2005, 5, 411-31). These include Ldmdr1 in *L. donovani*, Lamdr1 and Lamdr2 in *L. amazonensis*, LtpgpA in *L. tarentolae*, Ltmdr1 in *L. tropica*, Lemdr1 in *L. enriettii*, LmepgpA in *L. mexicana*, LmpgpA in *L. major* and PEN$^r$ in *L. major*. Structurally, they can be grouped into the ABCB (Ldmdr1, Lamdr1, Lamdr2, Ltrmdr1, Lemdr1 and PEN$^r$) and ABCC type (LtpgpA, LmepgpA and LmpgpA). Both ABCB and ABCC transporters have two NBDs and therefore are potential targets of flavonoids.

Success in overcoming MDR has been limited by a lack of specificity and a low affinity of MDR modulators for the drug binding sites of ABC transporter.

It has been shown in the above results that the flavonoid dimers of this invention can inhibit it and reverse the pentamidine resistance in parasitic diseases, particularly those caused by the genus *Leishmania*. Compounds 9c or 9d with two apigenins connected by three or four ethylene glycol units exhibited the highest modulating activity of both pentamidine and SSG resistance, with about 3-fold decrease in IC$_{50}$. Other flavonoid dimers of this invention with longer or shorter linker lengths also showed a lower or no modulating activity. The apigenin monomers with the same number of ethylene glycols in the linker (10a and 10b) did not have any modulating activity, even when twice the concentration was used (12 μM). This demonstrates that the modulatory activity of the flavonoid dimers of this invention, particularly 9c and 9d, is not due to the doubled concentration of the flavonoid binding to the ABC transporters, but rather due to the chain length effect of the ethylene glycol units between the two apigenins. The chain length having the best performance in reversing pentamidine and SSG resistance is 3 to 4 ethylene glycol units. Treatment with 9c and 9d resulted in a dose-dependent increase in the accumulation of pentamidine and SSG. This result may indirectly suggest that an efflux transporter is mediating pentamidine and SSG resistance by lowering the drug accumulation.

In comparison with other traditional MDR modulators, 9c and 9d exhibited a pentamidine resistance reversal activity comparable to reserpine and quinacrine. In case of SSG resistance, 9c and 9d have significant modulating activity while none of the traditional MDR modulators work.

While the preferred embodiment of the present invention has been described in detail by the examples, it is apparent that modifications and adaptations of the present invention will occur to those skilled in the art. Furthermore, the embodiments of the present invention shall not be interpreted to be restricted by the examples or figures only. It is to be expressly understood, however, that such modifications and adaptations

TABLE 4

Effect of synthetic flavonoid dimers on pentamidine resistance of LeMDR1 mutants

| | IC$_{50}$ of pentamidine (μg/ml) | | | IC$_{50}$ of vinblastine (μg/ml) | IC$_{50}$ of puromycin (μg/ml) |
|---|---|---|---|---|---|
| | LeMDR1−/− | Le | LeV160 | LeV160 | LeV160 |
| No modulator | 18.9 ± 0.8 | 12.0 ± 0.8 | 9.0 ± 0.1 | 167.0 ± 3.6 | 16.0 ± 1.0 |
| 9a | 18.0 ± 1.0 | — | — | 170.0 ± 7.0 | — |
| 9b | 9.4 ± 0.4 | — | — | 160.0 ± 6.0 | — |
| 9c | 5.0 ± 0.3 | — | 5.0 ± 0.4 | 134.0 ± 6.0 | 13.0 ± 0.5 |
| 9d | 4.6 ± 0.4 | 4.0 ± 0.3 | 4.7 ± 0.1 | 140.0 ± 2.3 | 15.0 ± 0.6 |
| 9e | 12.5 ± 0.1 | — | 7.5 ± 0.3 | 170.0 ± 2.3 | 19.0 ± 0.4 |
| 9f | 12.5 ± 0.8 | — | 7.2 ± 0.3 | 165.0 ± 2.3 | 17.0 ± 1.0 |
| 9h-1 | 8.2 ± 0.5 | — | — | 160.0 ± 8.0 | — |
| 9i | 13.8 ± 0.7 | — | 6.8 ± 0.2 | 165.0 ± 2.3 | 19.0 ± 0.8 |
| 9j | 20.9 ± 1.3 | — | — | 170.0 ± 4.0 | — |
| 9k-1 | 20.9 + 3.0 | — | — | 150.0 ± 6.0 | — |

The IC$_{50}$ values for each drug were determined by MTS-based proliferation assay.
Each IC50 value was derived from at least three independent experiments with triplicates in each experiment.
—Not determined

The invention claimed is:

1. A compound of formula I:

flavonoid-linker-flavonoid      I wherein
the flavonoid is apigenin; and
the linker is a group having 3 or 4 ethylene glycol units.

2. The compound of claim 1, wherein the linker has 4 ethylene glycol units.

3. A method of synthesizing a compound of formula I:

flavonoid-linker-flavonoid      I wherein
the flavonoid is apigenin; and
the linker is a group having 3 or 4 ethylene glycol units; including the steps of:

a) reacting p-hydroxybenzaldehyde with a compound of formula II to form a compound of formula III

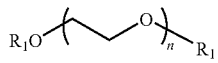
     II

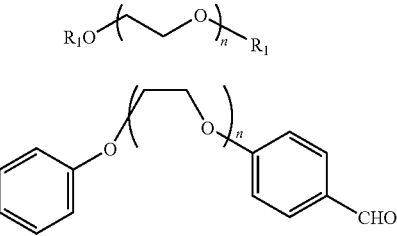
     III wherein $R_1$ is selected from —H, -tosylate, and -mesylate; and b) reacting the compound of formula III with a compound of formula IV

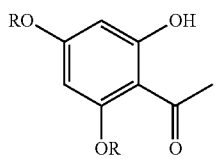
     IV to form the compound of formula I, wherein R is selected from the group consisting of —H, benzyl, and methoxymethyl.

4. A method of synthesizing a compound of formula I:

flavonoid-linker-flavonoid      I wherein
the flavonoid is apigenin; and
the linker is a group having 3 or 4 ethylene glycol units; including the steps of:

a) reacting p-hydroxybenzaldehyde with a compound of formula IV to form a compound of formula V

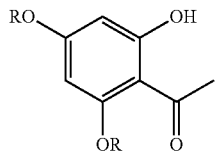
     IV

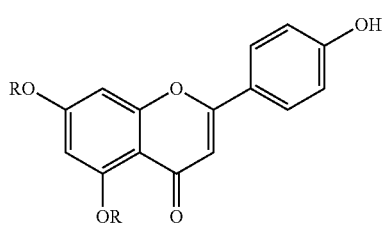
     V wherein R is selected from the group consisting of —H, benzyl and methoxymethyl; and b) reacting the compound of formula V with a compound of formula II to form the compound of formula I

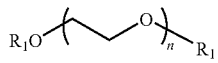
     II wherein $R_1$ is selected from —H, -tosylate, and -mesylate.

5. A method of reducing P-glycoprotein based multidrug resistance including the step of administering an effective amount of a compound of formula I:

flavonoid-linker-flavonoid      I wherein
the flavonoid is apigenin; and
the linker is a group having 3 or 4 ethylene glycol units.

6. The method of claim 5, wherein the linker has 4 ethylene glycol units.

7. The method of claim 5, wherein the compound of formula I has a concentration of 5 to 30 μM.

8. A method of reducing resistance of a drug in a parasitic disease including the step of administering an effective amount of a compound of formula I:

flavonoid-linker-flavonoid      I wherein
the flavonoid is apigenin; and
the linker is a group having 3 or 4 ethylene glycol units.

9. The method of claim 8, wherein the linker has 4 ethylene glycol units.

10. The method of claim 8, wherein the compound of formula I has a concentration of 4 to 60 μM.

11. The method of claim 8, wherein the parasitic disease is caused by genus *Leishmania*.

12. The method of claim 8, wherein the parasitic disease is caused by one of the parasites selected from the group consisting of *L. donovani, L. amazonensis, L. tarentolae, L. tropica, L. enriettii, L. mexicana*, and *L. major*.

13. The method of claim 8, wherein the drug is selected from the group consisting of sodium stibogluconate and pentamidine.

14. The method of claim 13, wherein the drug is in a concentration of 1 to 6.4 mg/mL.

15. A method of manufacturing a medicament for reducing P-glycoprotein based multidrug resistance, comprising providing an effective amount of the compound of claim 1.

16. A method of manufacturing a medicament for reducing resistance of a drug in a parasitic disease, comprising providing an effective amount of the compound of claim 1.

17. A medicament for reducing P-glycoprotein based multidrug resistance or for reducing resistance of a drug in a parasitic disease, said medicament including the compound of claim 1.

18. A medicament, comprising:
   a drug used to treat cancer, and
   the compound of claim 1.

* * * * *

UNITED STATES PATENT AND TRADEMARK OFFICE
CERTIFICATE OF CORRECTION

PATENT NO.       : 8,710,097 B2                                                          Page 1 of 1
APPLICATION NO.  : 12/301504
DATED            : April 29, 2014
INVENTOR(S)      : Chan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 726 days.

Signed and Sealed this

Twenty-ninth Day of September, 2015

Michelle K. Lee
*Director of the United States Patent and Trademark Office*